US011680231B2

(12) United States Patent
Oehlenschlaeger et al.

(10) Patent No.: US 11,680,231 B2
(45) Date of Patent: *Jun. 20, 2023

(54) DETERGENT COMPOSITIONS AND USES THEREOF

(71) Applicant: NOVOZYMES A/S, Bagsvaerd (DK)

(72) Inventors: Christian Berg Oehlenschlaeger, Valby (DK); Dorotea Raventos Segura, Rungsted (DK); Rebecca Munk Vejborg, Allerød (DK); Henrik Marcus Geertz-Hansen, Copenhagen (DK); Lilian Eva Tang Baltsen, Bagsvaerd (DK); Jesper Salomon, Holte (DK)

(73) Assignee: NOVOZYMES A/S, Bagsvaerd (DK)

( * ) Notice: Subject to any disclaimer, the term of this patent is extended or adjusted under 35 U.S.C. 154(b) by 261 days.

This patent is subject to a terminal disclaimer.

(21) Appl. No.: 16/815,281

(22) Filed: Mar. 11, 2020

(65) Prior Publication Data

US 2021/0284934 A1    Sep. 16, 2021

Related U.S. Application Data

(63) Continuation of application No. 16/094,740, filed as application No. PCT/EP2017/060265 on Apr. 28, 2017, now Pat. No. 10,626,354.

(30) Foreign Application Priority Data

Apr. 29, 2016 (DK) .......................... PA 2016 00262

(51) Int. Cl.
  *C12N 9/22* (2006.01)
  *C11D 3/386* (2006.01)

(52) U.S. Cl.
  CPC ...... *C11D 3/38636* (2013.01); *C11D 3/38663* (2013.01); *C12Y 302/01052* (2013.01)

(58) Field of Classification Search
  None
  See application file for complete search history.

(56) References Cited

U.S. PATENT DOCUMENTS

| | | | |
|---|---|---|---|
| 6,465,410 B1 | 10/2002 | Bettiol | |
| 6,468,955 B1 | 10/2002 | Smets | |
| 8,399,235 B2 | 3/2013 | Frank | |
| 8,821,862 B2 | 9/2014 | Madhyastha | |
| 10,626,354 B2* | 4/2020 | Ooehlenschlaeger | C12Y 302/01052 |
| 10,954,478 B2 | 3/2021 | Oehlenschlaeger et al. | |
| 11,414,652 B2* | 8/2022 | Vejborg | C12N 9/2402 |
| 2009/0155215 A1 | 6/2009 | Collins | |
| 2011/0196319 A1 | 8/2011 | Arscott, II | |
| 2012/0258089 A1 | 10/2012 | Madhyastha | |
| 2014/0073017 A1* | 3/2014 | Kaper | C12P 19/14 435/254.6 |
| 2019/0127663 A1 | 5/2019 | Oehlenschlaeger | |
| 2019/0161707 A1 | 5/2019 | Vejborg | |
| 2019/0169547 A1 | 6/2019 | Ooehlenschlaeger | |
| 2021/0155876 A1 | 5/2021 | Oehlenschlaeger et al. | |
| 2021/0284934 A1* | 9/2021 | Oehlenschlaeger | C11D 3/38636 |

FOREIGN PATENT DOCUMENTS

| | | |
|---|---|---|
| AU | 6559390 A | 5/1991 |
| WO | 98/50512 A1 | 11/1998 |
| WO | 99/57157 A1 | 11/1999 |
| WO | 2008/043175 A1 | 4/2008 |
| WO | 2009/121183 A1 | 10/2009 |
| WO | 2012/129515 A1 | 9/2012 |
| WO | 2015/196299 A1 | 12/2015 |

OTHER PUBLICATIONS

Andrew, 2016, Uniprot accession No. A0A0Q5CMZ8.
Andrew, 2016, Uniprot accession No. A0A0Q5KJC4.
Anonymous, 2013, NCBI No. WP_005560708.
Anonymous, 2013, NCBI No. WP_017886882.1.
Anonymous, 2013, NCBI No. WP_018652103.
Anonymous, 2015, NCBI No. WP_051596815.1.
Durkin et al, 2012, EBI Accession No. J4TU99.
Gillaspy et al, 2014, EBI Accession No. X2JMQ1.
Jackson et al, 2011, EBI Accession No. P86956.
Joubert et al, 2012, EBI Accession No. H2A0L6.
Kaplan et al, 2003, J Bacteriol 185(16), 4693-4698.
Kaplan et al, 2004, EBI Accession No. Q6GYA5.
Kaplan et al, 2009, International journal of artificial organs 32(9), 545-554.
Keeling et al, 2013, Uniprot accession No. U4URB2.
Krishnamurthi et al, 2008, Int Sys Evol Microbiol 58, 2287-2291.
Liu et al, 2010, Int Sys Evol Microbiol 60, 2940-2945.
Macinnes et al, 2012, EBI Accession No. K0G581.
Macinnes et al, 2015, EBI Accession No. A0A0A7MHS5.
McKinlay et al, 2016, Uniprot accession No. A6VMN2.
Ramasubbu et al, 2005, J Mol Biol 349(3), 475-486.
Tews et al, 1998, EBI Accession No. Q54468.
Wang et al, 2014, Uniprot accession No. A0A075LPR4.
Ward et al, 2016, Uniprot accession No. D7N318.
Weinstock et al, 2015, Uniprot accession No. E4HHI5.
Zhan et al, 2015, Uniprot accession No. D9PAB0.
Durkin et al., EBI Accession No. J4TU99 (2012).
Singh et al., Current Protein and Peptide Science, vol. 18, pp. 1-118 (2017).
Zhang et al., Structure, vol. 26, pp. 1474-1485 (2018).

* cited by examiner

Primary Examiner — Tekchand Saidha
(74) Attorney, Agent, or Firm — Elias Lambiris

(57) ABSTRACT

The present invention relates to polypeptides having hexosaminidase activity, and polynucleotides encoding the polypeptides. The invention also relates to nucleic acid constructs, vectors, and host cells comprising the polynucleotides as well as methods of producing and using the polypeptides.

21 Claims, 3 Drawing Sheets

Specification includes a Sequence Listing.

Figure 2

```
                        SEQUENCE LISTING

<160> NUMBER OF SEQ ID NOS: 24

<210> SEQ ID NO 1
<211> LENGTH: 1095
<212> TYPE: DNA
<213> ORGANISM: Terribacillus saccharophilus
<220> FEATURE:
<221> NAME/KEY: sig_peptide
<222> LOCATION: (1)..(123)
<220> FEATURE:
<221> NAME/KEY: CDS
<222> LOCATION: (1)..(1095)
<220> FEATURE:
<221> NAME/KEY: mat_peptide
<222> LOCATION: (124)..(1095)

<400> SEQUENCE: 1 atg gta tct cgc acg atg ctt ttc atc aag cgc gag aag ggc aag acg      48
Met Val Ser Arg Thr Met Leu Phe Ile Lys Arg Glu Lys Gly Lys Thr
    -40                 -35                 -30 gtt ctt atc aag ttc ctt tct atc acg aca gta tct atc ctt ctt ttc      96
Val Leu Ile Lys Phe Leu Ser Ile Thr Thr Val Ser Ile Leu Leu Phe
-25                 -20                 -15                 -10 ctt acg atg gcg aac act gcg caa gcg caa gac caa gag aag ggc atc     144
Leu Thr Met Ala Asn Thr Ala Gln Ala Gln Asp Gln Glu Lys Gly Ile
                 -5              -1   1               5 aca atc gac atc tct cgc aag tac tac agc atc aag acg ctt aag gcg     192
Thr Ile Asp Ile Ser Arg Lys Tyr Tyr Ser Ile Lys Thr Leu Lys Ala
            10                  15                  20 atc gtt gac gag atc tca gcg aat ggt ggc gac tac ctt caa ctt cac     240
Ile Val Asp Glu Ile Ser Ala Asn Gly Gly Asp Tyr Leu Gln Leu His
        25                  30                  35 ttc tct gac aac gag agc tac gcg atc gcg tct gag ttc ctt ggc caa     288
Phe Ser Asp Asn Glu Ser Tyr Ala Ile Ala Ser Glu Phe Leu Gly Gln
40                  45                  50                  55 aac tct gag aac cca aac tct gcg tac ctt aca aag aag gag ctt ctt     336
Asn Ser Glu Asn Pro Asn Ser Ala Tyr Leu Thr Lys Lys Glu Leu Leu
                60                  65                  70 tca ctt atc gcg tac tct aac gac cgc aac atc atg gtt atc ccg gac     384
Ser Leu Ile Ala Tyr Ser Asn Asp Arg Asn Ile Met Val Ile Pro Asp
            75                  80                  85 atc gac ctt cct gcg cac tca aag ggc tgg ctt aac atc atg aag gag     432
Ile Asp Leu Pro Ala His Ser Lys Gly Trp Leu Asn Ile Met Lys Glu
        90                  95                  100 aag gac tct ggc ctt tac aca gac atc gta act gac tac tca gaa gac     480
Lys Asp Ser Gly Leu Tyr Thr Asp Ile Val Thr Asp Tyr Ser Glu Asp
    105                 110                 115 act ctt gac tac cac aac aac gcg gtt gcg ctt tac acg gcg aac caa     528
Thr Leu Asp Tyr His Asn Asn Ala Val Ala Leu Tyr Thr Ala Asn Gln
```

```
ctt ctt gac gag gtt ctt gac ctt ttc tac caa cct aag ttt gct ggc      576
Leu Leu Asp Glu Val Leu Asp Leu Phe Tyr Gln Pro Lys Phe Ala Gly
            140                 145                 150 aag caa cgc atc gtt ctt ggt ggc gac gag gtt cct ggc tct ggt gcg      624
Lys Gln Arg Ile Val Leu Gly Gly Asp Glu Val Pro Gly Ser Gly Ala
            155                 160                 165 cac caa act gac ttc atc cgc ttc atg aac cag atc gcg aag aca gcg      672
His Gln Thr Asp Phe Ile Arg Phe Met Asn Gln Ile Ala Lys Thr Ala
            170                 175                 180 aag gcg tct aac tac gag cca caa atg tgg aac gac agc atc act cct      720
Lys Ala Ser Asn Tyr Glu Pro Gln Met Trp Asn Asp Ser Ile Thr Pro
            185                 190                 195 gag ggc atc caa aac ctt gac cgc tct ttc tct atc ctt tac tgg aag      768
Glu Gly Ile Gln Asn Leu Asp Arg Ser Phe Ser Ile Leu Tyr Trp Lys
200                 205                 210                 215 caa tca acg ctt tca aat ggt gcg caa tct ctt gac gta caa gac ttc      816
Gln Ser Thr Leu Ser Asn Gly Ala Gln Ser Leu Asp Val Gln Asp Phe
                220                 225                 230 gag gag aac ggc ctt tca gtt tac aac tac aac gct tac agc ctt tac      864
Glu Glu Asn Gly Leu Ser Val Tyr Asn Tyr Asn Ala Tyr Ser Leu Tyr
                235                 240                 245 ttc ctt cct agc act cgc ttc acg caa gag gac atc acg gag caa atc      912
Phe Leu Pro Ser Thr Arg Phe Thr Gln Glu Asp Ile Thr Glu Gln Ile
            250                 255                 260 gac tac atg aag tgg gcg tat gcg tac aac aag ttc ttc tac atc tct      960
Asp Tyr Met Lys Trp Ala Tyr Ala Tyr Asn Lys Phe Phe Tyr Ile Ser
            265                 270                 275 gac tac tac aag caa gta gac aca cca aac gta aag ggc tca tct ctt     1008
Asp Tyr Tyr Lys Gln Val Asp Thr Pro Asn Val Lys Gly Ser Ser Leu
280                 285                 290                 295 gta ttc tgg ggt gag cac gcg aac gac ctt tct caa gag ggc ctt ctt     1056
Val Phe Trp Gly Glu His Ala Asn Asp Leu Ser Gln Glu Gly Leu Leu
                300                 305                 310 aag caa gag aag cca ctt atc caa aac ttc ctt ggc ctt                 1095
Lys Gln Glu Lys Pro Leu Ile Gln Asn Phe Leu Gly Leu
            315                 320
```

<210> SEQ ID NO 2
<211> LENGTH: 365
<212> TYPE: PRT
<213> ORGANISM: Terribacillus saccharophilus

<400> SEQUENCE: 2

```
Met Val Ser Arg Thr Met Leu Phe Ile Lys Arg Glu Lys Gly Lys Thr
    -40                 -35                 -30

Val Leu Ile Lys Phe Leu Ser Ile Thr Thr Val Ser Ile Leu Leu Phe
-25                 -20                 -15                 -10

Leu Thr Met Ala Asn Thr Ala Gln Ala Gln Asp Gln Glu Lys Gly Ile
                -5                  -1  1                   5

Thr Ile Asp Ile Ser Arg Lys Tyr Tyr Ser Ile Lys Thr Leu Lys Ala
            10                  15                  20

Ile Val Asp Glu Ile Ser Ala Asn Gly Gly Asp Tyr Leu Gln Leu His
            25                  30                  35

Phe Ser Asp Asn Glu Ser Tyr Ala Ile Ala Ser Glu Phe Leu Gly Gln
40                  45                  50                  55

Asn Ser Glu Asn Pro Asn Ser Ala Tyr Leu Thr Lys Lys Glu Leu Leu
                60                  65                  70
```

-continued

```
Ser Leu Ile Ala Tyr Ser Asn Asp Arg Asn Ile Met Val Ile Pro Asp
         75                  80                  85

Ile Asp Leu Pro Ala His Ser Lys Gly Trp Leu Asn Ile Met Lys Glu
 90                  95                 100

Lys Asp Ser Gly Leu Tyr Thr Asp Ile Val Thr Asp Tyr Ser Glu Asp
    105                 110                 115

Thr Leu Asp Tyr His Asn Asn Ala Val Ala Leu Tyr Thr Ala Asn Gln
120                 125                 130                 135

Leu Leu Asp Glu Val Leu Asp Leu Phe Tyr Gln Pro Lys Phe Ala Gly
             140                 145                 150

Lys Gln Arg Ile Val Leu Gly Asp Glu Val Pro Gly Ser Gly Ala
            155                 160                 165

His Gln Thr Asp Phe Ile Arg Phe Met Asn Gln Ile Ala Lys Thr Ala
        170                 175                 180

Lys Ala Ser Asn Tyr Glu Pro Gln Met Trp Asn Asp Ser Ile Thr Pro
    185                 190                 195

Glu Gly Ile Gln Asn Leu Asp Arg Ser Phe Ser Ile Leu Tyr Trp Lys
200                 205                 210                 215

Gln Ser Thr Leu Ser Asn Gly Ala Gln Ser Leu Asp Val Gln Asp Phe
             220                 225                 230

Glu Glu Asn Gly Leu Ser Val Tyr Asn Tyr Asn Ala Tyr Ser Leu Tyr
        235                 240                 245

Phe Leu Pro Ser Thr Arg Phe Thr Gln Glu Asp Ile Thr Glu Gln Ile
    250                 255                 260

Asp Tyr Met Lys Trp Ala Tyr Ala Tyr Asn Lys Phe Phe Tyr Ile Ser
265                 270                 275

Asp Tyr Tyr Lys Gln Val Asp Thr Pro Asn Val Lys Gly Ser Ser Leu
280                 285                 290                 295

Val Phe Trp Gly Glu His Ala Asn Asp Leu Ser Gln Glu Gly Leu Leu
             300                 305                 310

Lys Gln Glu Lys Pro Leu Ile Gln Asn Phe Leu Gly Leu
        315                 320
```

```
<210> SEQ ID NO 3
<211> LENGTH: 1047
<212> TYPE: DNA
<213> ORGANISM: Terribacillus goriensis
<220> FEATURE:
<221> NAME/KEY: sig_peptide
<222> LOCATION: (1)..(75)
<220> FEATURE:
<221> NAME/KEY: CDS
<222> LOCATION: (1)..(1047)
<220> FEATURE:
<221> NAME/KEY: mat_peptide
<222> LOCATION: (76)..(1047)

<400> SEQUENCE: 3
```

```
atg ctt atc aag ttc ctt tct atc acg aca gtt tca atc ctt ctt ttc      48
Met Leu Ile Lys Phe Leu Ser Ile Thr Thr Val Ser Ile Leu Leu Phe
-25                 -20                 -15                 -10 ctt acg atg tct aac act gcg caa gcg caa gac caa gag aag ggc atc      96
Leu Thr Met Ser Asn Thr Ala Gln Ala Gln Asp Gln Glu Lys Gly Ile
             -5                  -1  1                   5 aca atc gac atc tct cgc aag tac tac tct atc gag aca ctt aag tct     144
Thr Ile Asp Ile Ser Arg Lys Tyr Tyr Ser Ile Glu Thr Leu Lys Ser
         10                  15                  20 atc atc gac gag atc tca gcg aat ggt ggc gac tac ctt caa ctt cat     192
Ile Ile Asp Glu Ile Ser Ala Asn Gly Gly Asp Tyr Leu Gln Leu His
```

|  |  |  |  |  |  |  |  |  |  |  |  |  |  |  |  |
|---|---|---|---|---|---|---|---|---|---|---|---|---|---|---|---|
|  |  | 25 |  |  |  | 30 |  |  |  | 35 |  |  |  |  |  |

```
ttc tct gac aac gag cgc tac gcg atc gcg tca gag ttc ctt ggc caa       240
Phe Ser Asp Asn Glu Arg Tyr Ala Ile Ala Ser Glu Phe Leu Gly Gln
 40                  45                  50                  55 aac ggc gag aac cca aac tct act tac ctt aca aag aag gag ctt ctt       288
Asn Gly Glu Asn Pro Asn Ser Thr Tyr Leu Thr Lys Lys Glu Leu Leu
                 60                  65                  70 tct ctt atc gcg tac tct aac gac cgc gac atc atg gta atc cca gac       336
Ser Leu Ile Ala Tyr Ser Asn Asp Arg Asp Ile Met Val Ile Pro Asp
         75                  80                  85 atc gac ctt cca gcg cat tct cgt ggc tgg ctt aac atc atg aag gag       384
Ile Asp Leu Pro Ala His Ser Arg Gly Trp Leu Asn Ile Met Lys Glu
     90                  95                 100 aag gac tca ggc ctt tac act gac atc gta acg gac tac tct gag gac       432
Lys Asp Ser Gly Leu Tyr Thr Asp Ile Val Thr Asp Tyr Ser Glu Asp
105                 110                 115 aca ctt gac tac cat aac aac gct gta gcg ctt tac aca gca aac caa       480
Thr Leu Asp Tyr His Asn Asn Ala Val Ala Leu Tyr Thr Ala Asn Gln
120                 125                 130                 135 ctt ctt gac gag gta ctt gac ctt ttc tac caa ccg aag ttt gct ggc       528
Leu Leu Asp Glu Val Leu Asp Leu Phe Tyr Gln Pro Lys Phe Ala Gly
                140                 145                 150 aag cag cgc atc gta ctt ggt ggc gac gag gtt cct ggc tct ggc gta       576
Lys Gln Arg Ile Val Leu Gly Gly Asp Glu Val Pro Gly Ser Gly Val
            155                 160                 165 cac cag act gac ttc atc cgc ttc atg aac caa atc gcg gag act gcg       624
His Gln Thr Asp Phe Ile Arg Phe Met Asn Gln Ile Ala Glu Thr Ala
        170                 175                 180 aag gct tct aac tac aag cca caa atg tgg aac gac tct atc aca cct       672
Lys Ala Ser Asn Tyr Lys Pro Gln Met Trp Asn Asp Ser Ile Thr Pro
    185                 190                 195 gag ggc atc caa aac ctt gac cgc tca ttc tct atc ctt tac tgg aag       720
Glu Gly Ile Gln Asn Leu Asp Arg Ser Phe Ser Ile Leu Tyr Trp Lys
200                 205                 210                 215 caa tct aca ctt agc aat ggt gcg caa ggc ctt gac gta caa gac ttc       768
Gln Ser Thr Leu Ser Asn Gly Ala Gln Gly Leu Asp Val Gln Asp Phe
                220                 225                 230 gag gag aac ggc ctt agc gtt tac aac tac aat gcg tac tca ctt tac       816
Glu Glu Asn Gly Leu Ser Val Tyr Asn Tyr Asn Ala Tyr Ser Leu Tyr
            235                 240                 245 ttc ctt cct gcg aca cgc ttc act caa gag gac atc act gag caa atc       864
Phe Leu Pro Ala Thr Arg Phe Thr Gln Glu Asp Ile Thr Glu Gln Ile
        250                 255                 260 gac tac atg aag tgg gcg tat gcg tac aac aag ttc ttc tac atc tct       912
Asp Tyr Met Lys Trp Ala Tyr Ala Tyr Asn Lys Phe Phe Tyr Ile Ser
    265                 270                 275 gac tac tac aag caa gta gac aca agc aac gtt aag ggc tct tct ctt       960
Asp Tyr Tyr Lys Gln Val Asp Thr Ser Asn Val Lys Gly Ser Ser Leu
280                 285                 290                 295 gta ttc tgg ggt gag cat gcg aac gac ctt agc caa gag ggc ctt ctt      1008
Val Phe Trp Gly Glu His Ala Asn Asp Leu Ser Gln Glu Gly Leu Leu
                300                 305                 310 aag caa gag aag cca ctt atc caa aac ttc ctt ggc ctt                  1047
Lys Gln Glu Lys Pro Leu Ile Gln Asn Phe Leu Gly Leu
            315                 320

<210> SEQ ID NO 4
<211> LENGTH: 349
<212> TYPE: PRT
<213> ORGANISM: Terribacillus goriensis
```

<400> SEQUENCE: 4

```
Met Leu Ile Lys Phe Leu Ser Ile Thr Thr Val Ser Ile Leu Leu Phe
-25                 -20                 -15                 -10

Leu Thr Met Ser Asn Thr Ala Gln Ala Gln Asp Gln Glu Lys Gly Ile
             -5                  -1   1                   5

Thr Ile Asp Ile Ser Arg Lys Tyr Tyr Ser Ile Glu Thr Leu Lys Ser
         10                  15                  20

Ile Ile Asp Glu Ile Ser Ala Asn Gly Gly Asp Tyr Leu Gln Leu His
             25                  30                  35

Phe Ser Asp Asn Glu Arg Tyr Ala Ile Ala Ser Glu Phe Leu Gly Gln
40                  45                  50                  55

Asn Gly Glu Asn Pro Asn Ser Thr Tyr Leu Thr Lys Lys Glu Leu Leu
                 60                  65                  70

Ser Leu Ile Ala Tyr Ser Asn Asp Arg Asp Ile Met Val Ile Pro Asp
             75                  80                  85

Ile Asp Leu Pro Ala His Ser Arg Gly Trp Leu Asn Ile Met Lys Glu
         90                  95                  100

Lys Asp Ser Gly Leu Tyr Thr Asp Ile Val Thr Asp Tyr Ser Glu Asp
105                 110                 115

Thr Leu Asp Tyr His Asn Asn Ala Val Ala Leu Tyr Thr Ala Asn Gln
120                 125                 130                 135

Leu Leu Asp Glu Val Leu Asp Leu Phe Tyr Gln Pro Lys Phe Ala Gly
                 140                 145                 150

Lys Gln Arg Ile Val Leu Gly Gly Asp Glu Val Pro Gly Ser Gly Val
             155                 160                 165

His Gln Thr Asp Phe Ile Arg Phe Met Asn Gln Ile Ala Glu Thr Ala
         170                 175                 180

Lys Ala Ser Asn Tyr Lys Pro Gln Met Trp Asn Asp Ser Ile Thr Pro
185                 190                 195

Glu Gly Ile Gln Asn Leu Asp Arg Ser Phe Ser Ile Leu Tyr Trp Lys
200                 205                 210                 215

Gln Ser Thr Leu Ser Asn Gly Ala Gln Gly Leu Asp Val Gln Asp Phe
                 220                 225                 230

Glu Glu Asn Gly Leu Ser Val Tyr Asn Tyr Asn Ala Tyr Ser Leu Tyr
             235                 240                 245

Phe Leu Pro Ala Thr Arg Phe Thr Gln Glu Asp Ile Thr Glu Gln Ile
         250                 255                 260

Asp Tyr Met Lys Trp Ala Tyr Ala Tyr Asn Lys Phe Phe Tyr Ile Ser
265                 270                 275

Asp Tyr Tyr Lys Gln Val Asp Thr Ser Asn Val Lys Gly Ser Ser Leu
280                 285                 290                 295

Val Phe Trp Gly Glu His Ala Asn Asp Leu Ser Gln Glu Gly Leu Leu
                 300                 305                 310

Lys Gln Glu Lys Pro Leu Ile Gly Asn Phe Leu Gly Leu
             315                 320
```

```
<210> SEQ ID NO 5
<211> LENGTH: 1047
<212> TYPE: DNA
<213> ORGANISM: Terribacillus saccharophilus
<220> FEATURE:
<221> NAME/KEY: sig_peptide
<222> LOCATION: (1)..(75)
<220> FEATURE:
<221> NAME/KEY: CDS
```

```
<222> LOCATION: (1)..(1047)
<220> FEATURE:
<221> NAME/KEY: mat_peptide
<222> LOCATION: (76)..(1047)

<400> SEQUENCE: 5 atg ctt atc aag ttc ctt tct atc act aca gtt tct atc ctt ctt ttc       48
Met Leu Ile Lys Phe Leu Ser Ile Thr Thr Val Ser Ile Leu Leu Phe
-25                 -20                 -15                 -10 ctt aca atg gcg aac act gcg caa gcg aag gac caa gag aag ggc atc       96
Leu Thr Met Ala Asn Thr Ala Gln Ala Lys Asp Gln Glu Lys Gly Ile
            -5                  -1  1                   5 act atc gac atc tca cgc aag tac tac tct atc ggc act ctt aaa gcg      144
Thr Ile Asp Ile Ser Arg Lys Tyr Tyr Ser Ile Gly Thr Leu Lys Ala
         10                  15                  20 atc gta gac gag atc aac gcg aat ggt ggc gac tac ctt caa ctt cac      192
Ile Val Asp Glu Ile Asn Ala Asn Gly Gly Asp Tyr Leu Gln Leu His
         25                  30                  35 ttc tct gac aac gag tca tac gcg atc gcg tca gag ttc ctt ggc caa      240
Phe Ser Asp Asn Glu Ser Tyr Ala Ile Ala Ser Glu Phe Leu Gly Gln
40                  45                  50                  55 aac agc gag aac cca aac agc act tac ctt aca aag aag gag ctt ctt      288
Asn Ser Glu Asn Pro Asn Ser Thr Tyr Leu Thr Lys Lys Glu Leu Leu
                60                  65                  70 tca ctt atc gcg tac agc aac gac cgc aac atc atg gta atc cca gac      336
Ser Leu Ile Ala Tyr Ser Asn Asp Arg Asn Ile Met Val Ile Pro Asp
             75                  80                  85 atc gac ctt cct gcg cac tca aag ggc tgg ctt aac gta atg aag gag      384
Ile Asp Leu Pro Ala His Ser Lys Gly Trp Leu Asn Val Met Lys Glu
         90                  95                 100 aag gac tct ggc ctt tac aca gac atc gtt aca gac tac agc gag gac      432
Lys Asp Ser Gly Leu Tyr Thr Asp Ile Val Thr Asp Tyr Ser Glu Asp
         105                 110                 115 aca ctt gac tac cac aac aat gct gct gcg ctt tac act gcg aac caa      480
Thr Leu Asp Tyr His Asn Asn Ala Ala Ala Leu Tyr Thr Ala Asn Gln
120                 125                 130                 135 ctt ctt gac gag gta ctt gac ctt ttc tac caa cca aag ttt gct ggc      528
Leu Leu Asp Glu Val Leu Asp Leu Phe Tyr Gln Pro Lys Phe Ala Gly
                140                 145                 150 aag caa cgc atc gtt ctt ggt ggc gac gag gta cca ggc tct ggt gcg      576
Lys Gln Arg Ile Val Leu Gly Gly Asp Glu Val Pro Gly Ser Gly Ala
                155                 160                 165 cac caa aca gac ttc atc cgc ttc atg aac caa atc gac gag act gcg      624
His Gln Thr Asp Phe Ile Arg Phe Met Asn Gln Ile Asp Glu Thr Ala
            170                 175                 180 aag gcg tca aac tac gag cca caa atg tgg aac gac tct atc aca cca      672
Lys Ala Ser Asn Tyr Glu Pro Gln Met Trp Asn Asp Ser Ile Thr Pro
185                 190                 195 gag ggc atc caa aac ctt gac cgc tca ttc agc atc ctt tac tgg aag      720
Glu Gly Ile Gln Asn Leu Asp Arg Ser Phe Ser Ile Leu Tyr Trp Lys
200                 205                 210                 215 caa tct act ctt agc tct ggt gcg caa ggc ctt gac gta caa aac ttc      768
Gln Ser Thr Leu Ser Ser Gly Ala Gln Gly Leu Asp Val Gln Asn Phe
                220                 225                 230 gag gag aag ggc ttc tct gtt tac aac tac aat gcg tac tct ctt tac      816
Glu Glu Lys Gly Phe Ser Val Tyr Asn Tyr Asn Ala Tyr Ser Leu Tyr
            235                 240                 245 ttc ctt cct tct aca cgc ttc act cag gag gac atc acg gag caa atc      864
Phe Leu Pro Ser Thr Arg Phe Thr Gln Glu Asp Ile Thr Glu Gln Ile
         250                 255                 260
```

| | | | | | | | | | | | | | | | |
|---|---|---|---|---|---|---|---|---|---|---|---|---|---|---|---|
|gac|tac|atg|aag|tgg|gcg|tat|gcg|tac|aac|aag|ttc|ttc|tac|atc|tca|
|Asp|Tyr|Met|Lys|Trp|Ala|Tyr|Ala|Tyr|Asn|Lys|Phe|Phe|Tyr|Ile|Ser|
| |265| | | |270| | | |275| | | | | | |

912

| | | | | | | | | | | | | | | | |
|---|---|---|---|---|---|---|---|---|---|---|---|---|---|---|---|
|gac|tac|tac|aag|caa|gta|gac|acg|agc|aac|gta|aag|ggc|agc|tca|ctt|
|Asp|Tyr|Tyr|Lys|Gln|Val|Asp|Thr|Ser|Asn|Val|Lys|Gly|Ser|Ser|Leu|
|280| | | | |285| | | | |290| | | | |295|

960

| | | | | | | | | | | | | | | | |
|---|---|---|---|---|---|---|---|---|---|---|---|---|---|---|---|
|gtt|ttc|tgg|ggt|gag|cac|gcg|aac|gac|ctt|tct|caa|gag|ggc|ctt|ctt|
|Val|Phe|Trp|Gly|Glu|His|Ala|Asn|Asp|Leu|Ser|Gln|Glu|Gly|Leu|Leu|
| | | | |300| | | | |305| | | | |310| |

1008

| | | | | | | | | | | |
|---|---|---|---|---|---|---|---|---|---|---|
|gag|caa|gag|aag|cca|ctt|atc|caa|aac|ttc|ctt|tct|ctt|
|Glu|Gln|Glu|Lys|Pro|Leu|Ile|Gln|Asn|Phe|Leu|Ser|Leu|
| | | |315| | | | |320| | | | |

1047

<210> SEQ ID NO 6
<211> LENGTH: 349
<212> TYPE: PRT
<213> ORGANISM: Terribacillus saccharophilus

<400> SEQUENCE: 6

Met Leu Ile Lys Phe Leu Ser Ile Thr Thr Val Ser Ile Leu Leu Phe
-25             -20                 -15                 -10

Leu Thr Met Ala Asn Thr Ala Gln Ala Lys Asp Gln Glu Lys Gly Ile
            -5              -1  1               5

Thr Ile Asp Ile Ser Arg Lys Tyr Tyr Ser Ile Gly Thr Leu Lys Ala
            10                  15                  20

Ile Val Asp Glu Ile Asn Ala Asn Gly Gly Asp Tyr Leu Gln Leu His
        25                  30                  35

Phe Ser Asp Asn Glu Ser Tyr Ala Ile Ala Ser Glu Phe Leu Gly Gln
40                  45                  50                  55

Asn Ser Glu Asn Pro Asn Ser Thr Tyr Leu Thr Lys Lys Glu Leu Leu
                60                  65                  70

Ser Leu Ile Ala Tyr Ser Asn Asp Arg Asn Ile Met Val Ile Pro Asp
            75                  80                  85

Ile Asp Leu Pro Ala His Ser Lys Gly Trp Leu Asn Val Met Lys Glu
        90                  95                  100

Lys Asp Ser Gly Leu Tyr Thr Asp Ile Val Thr Asp Tyr Ser Glu Asp
105                 110                 115

Thr Leu Asp Tyr His Asn Asn Ala Ala Ala Leu Tyr Thr Ala Asn Gln
120                 125                 130                 135

Leu Leu Asp Glu Val Leu Asp Leu Phe Tyr Gln Pro Lys Phe Ala Gly
                140                 145                 150

Lys Gln Arg Ile Val Leu Gly Gly Asp Glu Val Pro Gly Ser Gly Ala
            155                 160                 165

His Gln Thr Asp Phe Ile Arg Phe Met Asn Gln Ile Asp Glu Thr Ala
        170                 175                 180

Lys Ala Ser Asn Tyr Glu Pro Gln Met Trp Asn Asp Ser Ile Thr Pro
    185                 190                 195

Glu Gly Ile Gln Asn Leu Asp Arg Ser Phe Ser Ile Leu Tyr Trp Lys
200                 205                 210                 215

Gln Ser Thr Leu Ser Ser Gly Ala Gln Gly Leu Asp Val Gln Asn Phe
                220                 225                 230

Glu Glu Lys Gly Phe Ser Val Tyr Asn Tyr Asn Ala Tyr Ser Leu Tyr
            235                 240                 245

Phe Leu Pro Ser Thr Arg Phe Thr Gln Glu Asp Ile Thr Glu Gln Ile
        250                 255                 260

Asp Tyr Met Lys Trp Ala Tyr Ala Tyr Asn Lys Phe Phe Tyr Ile Ser

```
                    265                 270                 275
Asp Tyr Tyr Lys Gln Val Asp Thr Ser Asn Val Lys Gly Ser Ser Leu
280                 285                 290                 295

Val Phe Trp Gly Glu His Ala Asn Asp Leu Ser Gln Glu Gly Leu Leu
                300                 305                 310

Glu Gln Glu Lys Pro Leu Ile Gln Asn Phe Leu Ser Leu
            315                 320

<210> SEQ ID NO 7
<211> LENGTH: 324
<212> TYPE: PRT
<213> ORGANISM: Terribacillus saccharophilus

<400> SEQUENCE: 7

Gln Asp Gln Glu Lys Gly Ile Thr Ile Asp Ile Ser Arg Lys Tyr Tyr
1               5                   10                  15

Ser Ile Lys Thr Leu Lys Ala Ile Val Asp Glu Ile Ser Ala Asn Gly
            20                  25                  30

Gly Asp Tyr Leu Gln Leu His Phe Ser Asp Asn Glu Ser Tyr Ala Ile
        35                  40                  45

Ala Ser Glu Phe Leu Gly Gln Asn Ser Glu Asn Pro Asn Ser Ala Tyr
50                  55                  60

Leu Thr Lys Lys Glu Leu Leu Ser Leu Ile Ala Tyr Ser Asn Asp Arg
65                  70                  75                  80

Asn Ile Met Val Ile Pro Asp Ile Asp Leu Pro Ala His Ser Lys Gly
                85                  90                  95

Trp Leu Asn Ile Met Lys Glu Lys Asp Ser Gly Leu Tyr Thr Asp Ile
            100                 105                 110

Val Thr Asp Tyr Ser Glu Asp Thr Leu Asp Tyr His Asn Asn Ala Val
        115                 120                 125

Ala Leu Tyr Thr Ala Asn Gln Leu Leu Asp Glu Val Leu Asp Leu Phe
130                 135                 140

Tyr Gln Pro Lys Phe Ala Gly Lys Gln Arg Ile Val Leu Gly Gly Asp
145                 150                 155                 160

Glu Val Pro Gly Ser Gly Ala His Gln Thr Asp Phe Ile Arg Phe Met
                165                 170                 175

Asn Gln Ile Ala Lys Thr Ala Lys Ala Ser Asn Tyr Glu Pro Gln Met
            180                 185                 190

Trp Asn Asp Ser Ile Thr Pro Glu Gly Ile Gln Asn Leu Asp Arg Ser
        195                 200                 205

Phe Ser Ile Leu Tyr Trp Lys Gln Ser Thr Leu Ser Asn Gly Ala Gln
210                 215                 220

Ser Leu Asp Val Gln Asp Phe Glu Glu Asn Gly Leu Ser Val Tyr Asn
225                 230                 235                 240

Tyr Asn Ala Tyr Ser Leu Tyr Phe Leu Pro Ser Thr Arg Phe Thr Gln
                245                 250                 255

Glu Asp Ile Thr Glu Gln Ile Asp Tyr Met Lys Trp Ala Tyr Ala Tyr
            260                 265                 270

Asn Lys Phe Phe Tyr Ile Ser Asp Tyr Tyr Lys Gln Val Asp Thr Pro
        275                 280                 285

Asn Val Lys Gly Ser Ser Leu Val Phe Trp Gly Glu His Ala Asn Asp
290                 295                 300

Leu Ser Gln Glu Gly Leu Leu Lys Gln Glu Lys Pro Leu Ile Gln Asn
305                 310                 315                 320
```

Phe Leu Gly Leu

<210> SEQ ID NO 8
<211> LENGTH: 324
<212> TYPE: PRT
<213> ORGANISM: Terribacillus goriensis

<400> SEQUENCE: 8

Gln Asp Gln Glu Lys Gly Ile Thr Ile Asp Ile Ser Arg Lys Tyr Tyr
1               5                   10                  15

Ser Ile Glu Thr Leu Lys Ser Ile Ile Asp Glu Ile Ser Ala Asn Gly
                20                  25                  30

Gly Asp Tyr Leu Gln Leu His Phe Ser Asp Asn Glu Arg Tyr Ala Ile
            35                  40                  45

Ala Ser Glu Phe Leu Gly Gln Asn Gly Glu Asn Pro Asn Ser Thr Tyr
        50                  55                  60

Leu Thr Lys Lys Glu Leu Leu Ser Leu Ile Ala Tyr Ser Asn Asp Arg
65                  70                  75                  80

Asp Ile Met Val Ile Pro Asp Ile Asp Leu Pro Ala His Ser Arg Gly
                85                  90                  95

Trp Leu Asn Ile Met Lys Glu Lys Asp Ser Gly Leu Tyr Thr Asp Ile
            100                 105                 110

Val Thr Asp Tyr Ser Glu Asp Thr Leu Asp Tyr His Asn Asn Ala Val
        115                 120                 125

Ala Leu Tyr Thr Ala Asn Gln Leu Leu Asp Glu Val Leu Asp Leu Phe
    130                 135                 140

Tyr Gln Pro Lys Phe Ala Gly Lys Gln Arg Ile Val Leu Gly Gly Asp
145                 150                 155                 160

Glu Val Pro Gly Ser Gly Val His Gln Thr Asp Phe Ile Arg Phe Met
                165                 170                 175

Asn Gln Ile Ala Glu Thr Ala Lys Ala Ser Asn Tyr Lys Pro Gln Met
            180                 185                 190

Trp Asn Asp Ser Ile Thr Pro Glu Gly Ile Gln Asn Leu Asp Arg Ser
        195                 200                 205

Phe Ser Ile Leu Tyr Trp Lys Gln Ser Thr Leu Ser Asn Gly Ala Gln
    210                 215                 220

Gly Leu Asp Val Gln Asp Phe Glu Glu Asn Gly Leu Ser Val Tyr Asn
225                 230                 235                 240

Tyr Asn Ala Tyr Ser Leu Tyr Phe Leu Pro Ala Thr Arg Phe Thr Gln
                245                 250                 255

Glu Asp Ile Thr Glu Gln Ile Asp Tyr Met Lys Trp Ala Tyr Ala Tyr
            260                 265                 270

Asn Lys Phe Phe Tyr Ile Ser Asp Tyr Tyr Lys Gln Val Asp Thr Ser
        275                 280                 285

Asn Val Lys Gly Ser Ser Leu Val Phe Trp Gly Glu His Ala Asn Asp
    290                 295                 300

Leu Ser Gln Glu Gly Leu Leu Lys Gln Glu Lys Pro Leu Ile Gln Asn
305                 310                 315                 320

Phe Leu Gly Leu

<210> SEQ ID NO 9
<211> LENGTH: 324
<212> TYPE: PRT
<213> ORGANISM: Terribacillus saccharophilus

<400> SEQUENCE: 9

-continued

```
Lys Asp Gln Glu Lys Gly Ile Thr Ile Asp Ile Ser Arg Lys Tyr Tyr
1               5                   10                  15

Ser Ile Gly Thr Leu Lys Ala Ile Val Asp Glu Ile Asn Ala Asn Gly
            20                  25                  30

Gly Asp Tyr Leu Gln Leu His Phe Ser Asp Asn Glu Ser Tyr Ala Ile
        35                  40                  45

Ala Ser Glu Phe Leu Gly Gln Asn Ser Glu Asn Pro Asn Ser Thr Tyr
50                  55                  60

Leu Thr Lys Lys Glu Leu Leu Ser Leu Ile Ala Tyr Ser Asn Asp Arg
65                  70                  75                  80

Asn Ile Met Val Ile Pro Asp Ile Asp Leu Pro Ala His Ser Lys Gly
                85                  90                  95

Trp Leu Asn Val Met Lys Glu Lys Asp Ser Gly Leu Tyr Thr Asp Ile
            100                 105                 110

Val Thr Asp Tyr Ser Glu Asp Thr Leu Asp Tyr His Asn Asn Ala Ala
        115                 120                 125

Ala Leu Tyr Thr Ala Asn Gln Leu Leu Asp Glu Val Leu Asp Leu Phe
130                 135                 140

Tyr Gln Pro Lys Phe Ala Gly Lys Gln Arg Ile Val Leu Gly Gly Asp
145                 150                 155                 160

Glu Val Pro Gly Ser Gly Ala His Gln Thr Asp Phe Ile Arg Phe Met
                165                 170                 175

Asn Gln Ile Asp Glu Thr Ala Lys Ala Ser Asn Tyr Glu Pro Gln Met
            180                 185                 190

Trp Asn Asp Ser Ile Thr Pro Glu Gly Ile Gln Asn Leu Asp Arg Ser
        195                 200                 205

Phe Ser Ile Leu Tyr Trp Lys Gln Ser Thr Leu Ser Ser Gly Ala Gln
210                 215                 220

Gly Leu Asp Val Gln Asn Phe Glu Glu Lys Gly Phe Ser Val Tyr Asn
225                 230                 235                 240

Tyr Asn Ala Tyr Ser Leu Tyr Phe Leu Pro Ser Thr Arg Phe Thr Gln
                245                 250                 255

Glu Asp Ile Thr Glu Gln Ile Asp Tyr Met Lys Trp Ala Tyr Ala Tyr
            260                 265                 270

Asn Lys Phe Phe Tyr Ile Ser Asp Tyr Tyr Lys Gln Val Asp Thr Ser
        275                 280                 285

Asn Val Lys Gly Ser Ser Leu Val Phe Trp Gly Glu His Ala Asn Asp
290                 295                 300

Leu Ser Gln Glu Gly Leu Leu Glu Gln Glu Lys Pro Leu Ile Gln Asn
305                 310                 315                 320

Phe Leu Ser Leu

<210> SEQ ID NO 10
<211> LENGTH: 324
<212> TYPE: PRT
<213> ORGANISM: Terribacillus saccharophilus

<400> SEQUENCE: 10

Gln Asp Gln Glu Lys Gly Ile Thr Ile Asp Ile Ser Arg Lys His Tyr
1               5                   10                  15

Thr Val Glu Thr Leu Lys Ser Leu Val Asp Glu Ile Ser Tyr Asn Gly
            20                  25                  30

Gly Asn Tyr Val Gln Leu His Phe Ser Asp Asn Glu Asn Tyr Ala Ile
        35                  40                  45
```

Ala Ser Glu Tyr Leu Gly Gln Ser Ser Glu Asn Thr Asn Asn Thr Tyr
            50                  55                  60

Leu Thr Lys Asn Glu Leu Ser Leu Ile Ala Tyr Ser Asn Asp Lys
 65                  70                  75                  80

Asp Ile Leu Val Ile Pro Asp Ile Asp Leu Pro Ala His Ser Lys Gly
                    85                  90                  95

Trp Leu Glu Leu Ile Lys Lys Lys Asp Val Lys Leu Tyr Asn Asp Ile
                100                 105                 110

Val Thr Asp Tyr Ser Glu Glu Thr Leu Asp Tyr Tyr Asp Asn Arg Val
            115                 120                 125

Ala Leu Asp Thr Val Asn Gln Leu Leu Asp Glu Val Leu Asp Leu Phe
            130                 135                 140

Tyr Gln Pro Lys Phe Glu Gly Lys Gln Arg Ile Val Leu Gly Gly Asp
145                 150                 155                 160

Glu Val Ser Gly Ser Glu Val His Gln Leu Asp Phe Ile Asp Phe Met
                165                 170                 175

Asn Gln Ile Ala Ser Thr Val Lys Glu Ser Lys Tyr Glu Pro Gln Met
                180                 185                 190

Trp Asn Asp Ser Ile Thr Ser Glu Gly Ile Ala Asn Leu Asp Asp Ser
                195                 200                 205

Phe Ser Ile Leu Tyr Trp Gln Gln Ser Thr Leu Ser Ser Gly Glu Glu
210                 215                 220

Ser Leu Asn Val Glu Asp Phe Glu Asn Trp Gly Phe Ser Val Tyr Asn
225                 230                 235                 240

Tyr Asn Ala Tyr Ser Leu Tyr Phe Leu Pro Ser Asn Gly Phe Thr Gln
                245                 250                 255

Glu Asp Ile Asn Glu Gln Met Asp Tyr Met Asn Trp Ala Tyr Ala His
                260                 265                 270

Asn Lys Phe Phe Tyr Ile Ser Asp Tyr His Ala Val Glu Thr Ser
                275                 280                 285

Asn Val Lys Gly Ser Ser Leu Thr Phe Trp Gly Glu His Ala Thr Asp
            290                 295                 300

Leu Ser Gln Lys Lys Leu Leu Lys Gln Glu Leu Pro Leu Ile Arg His
305                 310                 315                 320

Tyr Leu Asn Leu

<210> SEQ ID NO 11
<211> LENGTH: 324
<212> TYPE: PRT
<213> ORGANISM: Terribacillus saccharophilus

<400> SEQUENCE: 11

Lys Asp Gln Glu Lys Gly Ile Ser Ile Asp Ile Ser Arg Lys Tyr Tyr
 1               5                  10                  15

Ser Ile Gly Thr Leu Lys Ala Ile Ile Asp Glu Ile Ser Ala Asn Gly
                20                  25                  30

Gly Asp Tyr Leu Gln Leu His Phe Ser Asp Asn Glu Ser Tyr Ala Ile
            35                  40                  45

Ala Ser Asp Tyr Leu Gly Gln Ile Ser Asp Thr Pro Asn Asn Thr Tyr
            50                  55                  60

Leu Thr Lys Asn Asp Leu Leu Ser Leu Ile Ala Tyr Ser Asn Asp Arg
 65                  70                  75                  80

Asn Ile Leu Ile Ile Pro Asp Met Asp Leu Pro Ala His Ser Arg Gly
                    85                  90                  95

```
Trp Leu Glu Leu Met Lys Val Lys Asp Arg Glu Leu Tyr Thr Asp Ile
            100                 105                 110
Val Thr Asp Tyr Ser Asn Glu Thr Leu Asp Tyr His Asn Asn Thr Asp
        115                 120                 125
Ala Leu Asn Thr Ala Asn Gln Leu Leu Asn Glu Ile Leu Glu Leu Phe
130                 135                 140
Tyr Gln Pro Lys Phe Ala Gly Lys Gln Arg Ile Val Leu Gly Gly Asp
145                 150                 155                 160
Glu Val Pro Gly Ser Glu Ile His Gln Leu Asp Phe Ile Arg Phe Ile
                165                 170                 175
Asn Gln Ile Ala Ser Thr Ala Lys Ala Ser Asn Tyr Ala Pro Gln Met
            180                 185                 190
Trp Asn Asp Ser Ile Thr Ala Glu Gly Ile Gln Asn Leu Asp Lys Ser
        195                 200                 205
Phe Ser Ile Leu Tyr Trp Lys Gln Ser Thr Leu Ser Asn Gly Ala Gln
210                 215                 220
Ser Leu Glu Val Gln Asp Phe Glu Asp Trp Asp Phe Pro Val Tyr Asn
225                 230                 235                 240
Tyr Asn Ala Tyr Ser Leu Tyr Phe Leu Pro Ser Ile Arg Phe Thr Asp
                245                 250                 255
Glu Asp Ile Thr Glu Gln Met Asn Tyr Met Lys Trp Ala Tyr Ala Tyr
            260                 265                 270
Asn Lys Phe Phe Tyr Ile Ser Asp Tyr Tyr Lys Ser Val Asp Ala Ser
        275                 280                 285
Asn Val Lys Gly Ser Ser Leu Thr Phe Trp Gly Glu His Ala Thr Asp
290                 295                 300
Leu Ser Gln Glu Glu Leu Leu Glu Gln Glu Leu Pro Leu Ile Lys Lys
305                 310                 315                 320
Phe Leu Ser Leu

<210> SEQ ID NO 12
<211> LENGTH: 1047
<212> TYPE: DNA
<213> ORGANISM: Terribacillus saccharophilus
<220> FEATURE:
<221> NAME/KEY: CDS
<222> LOCATION: (1)..(1044)
<220> FEATURE:
<221> NAME/KEY: sig_peptide
<222> LOCATION: (1)..(72)
<220> FEATURE:
<221> NAME/KEY: mat_peptide
<222> LOCATION: (73)..(1044)

<400> SEQUENCE: 12 ttg ttt aaa att ctt tcc att aca gca ctt ggt atg att cta ttt ctg       48
Leu Phe Lys Ile Leu Ser Ile Thr Ala Leu Gly Met Ile Leu Phe Leu
                -20                 -15                 -10 act atg tcg aat aca gtt caa gcc cag gat caa gaa aaa gga att aca       96
Thr Met Ser Asn Thr Val Gln Ala Gln Asp Gln Glu Lys Gly Ile Thr
            -5                  -1  1               5 atc gat att tcg agg aaa cac tat act gtt gaa aca ctg aaa agc ctt      144
Ile Asp Ile Ser Arg Lys His Tyr Thr Val Glu Thr Leu Lys Ser Leu
        10                  15                  20 gta gat gaa ata agc tat aat ggc ggg aac tac gta cag ctg cat ttt      192
Val Asp Glu Ile Ser Tyr Asn Gly Gly Asn Tyr Val Gln Leu His Phe
25                  30                  35                  40 tcc gat aat gag aat tat gct ata gct tct gaa tat ctt ggt cag agc      240
```

```
                Ser Asp Asn Glu Asn Tyr Ala Ile Ala Ser Glu Tyr Leu Gly Gln Ser
                                45                  50                  55 agt gag aat acc aat aat aca tat ttg acg aaa aat gaa ctt cta tca        288
Ser Glu Asn Thr Asn Asn Thr Tyr Leu Thr Lys Asn Glu Leu Leu Ser
            60                  65                  70 tta ata gca tat agt aat gat aaa gat ata ctg gtc att cct gat att        336
Leu Ile Ala Tyr Ser Asn Asp Lys Asp Ile Leu Val Ile Pro Asp Ile
            75                  80                  85 gat ctg ccg gcg cac tcc aag ggg tgg ctg gaa tta atc aaa aag aaa        384
Asp Leu Pro Ala His Ser Lys Gly Trp Leu Glu Leu Ile Lys Lys Lys
    90                  95                 100 gat gtg aag tta tat aat gac atc gta acg gat tac agc gaa gag aca        432
Asp Val Lys Leu Tyr Asn Asp Ile Val Thr Asp Tyr Ser Glu Glu Thr
105                 110                 115                 120 ctg gat tat tat gat aat aga gtc gca ttg gat act gtg aat cag ctg        480
Leu Asp Tyr Tyr Asp Asn Arg Val Ala Leu Asp Thr Val Asn Gln Leu
                125                 130                 135 ttg gat gaa gtg ctt gat ttg ttt tat cag cca aaa ttc gaa gga aaa        528
Leu Asp Glu Val Leu Asp Leu Phe Tyr Gln Pro Lys Phe Glu Gly Lys
            140                 145                 150 caa aga ata gtg ctt ggc ggg gat gaa gta tcg gga agt gaa gtg cat        576
Gln Arg Ile Val Leu Gly Gly Asp Glu Val Ser Gly Ser Glu Val His
            155                 160                 165 cag ttg gat ttt att gat ttt atg aat cag att gcc agt aca gtc aaa        624
Gln Leu Asp Phe Ile Asp Phe Met Asn Gln Ile Ala Ser Thr Val Lys
    170                 175                 180 gaa agc aaa tat gaa ccg caa atg tgg aat gac agc atc acg tca gaa        672
Glu Ser Lys Tyr Glu Pro Gln Met Trp Asn Asp Ser Ile Thr Ser Glu
185                 190                 195                 200 gga ata gcg aac ttg gac gat agc ttt tcc atc ctc tat tgg cag caa        720
Gly Ile Ala Asn Leu Asp Asp Ser Phe Ser Ile Leu Tyr Trp Gln Gln
                205                 210                 215 agt aca ctt tcc agc gga gaa gaa agc ttg aat gtg gag gac ttt gaa        768
Ser Thr Leu Ser Ser Gly Glu Glu Ser Leu Asn Val Glu Asp Phe Glu
            220                 225                 230 aac tgg ggt ttc tcc gta tat aac tat aat gca tat tct ttg tac ttc        816
Asn Trp Gly Phe Ser Val Tyr Asn Tyr Asn Ala Tyr Ser Leu Tyr Phe
            235                 240                 245 tta cca tca aac ggg ttt aca cag gaa gat atc aat gag cag atg gat        864
Leu Pro Ser Asn Gly Phe Thr Gln Glu Asp Ile Asn Glu Gln Met Asp
    250                 255                 260 tat atg aat tgg gct tat gcg cat aat aaa ttt ttc tat att tca gat        912
Tyr Met Asn Trp Ala Tyr Ala His Asn Lys Phe Phe Tyr Ile Ser Asp
265                 270                 275                 280 tac tat cat gcg gtg gaa act tct aat gta aaa ggt tca agt ctg acc        960
Tyr Tyr His Ala Val Glu Thr Ser Asn Val Lys Gly Ser Ser Leu Thr
                285                 290                 295 ttt tgg ggc gaa cat gca act gac ttg agc caa aag aaa tta tta aag       1008
Phe Trp Gly Glu His Ala Thr Asp Leu Ser Gln Lys Lys Leu Leu Lys
            300                 305                 310 caa gag ctg cct ttg ata aga cat tat ctg aac ttg taa                   1047
Gln Glu Leu Pro Leu Ile Arg His Tyr Leu Asn Leu
            315                 320

<210> SEQ ID NO 13
<211> LENGTH: 348
<212> TYPE: PRT
<213> ORGANISM: Terribacillus saccharophilus

<400> SEQUENCE: 13
```

```
Leu Phe Lys Ile Leu Ser Ile Thr Ala Leu Gly Met Ile Leu Phe Leu
            -20                 -15                 -10

Thr Met Ser Asn Thr Val Gln Ala Gln Asp Gln Glu Lys Gly Ile Thr
         -5              -1   1                   5

Ile Asp Ile Ser Arg Lys His Tyr Thr Val Glu Thr Leu Lys Ser Leu
     10              15                  20

Val Asp Glu Ile Ser Tyr Asn Gly Gly Asn Tyr Val Gln Leu His Phe
 25              30                  35                      40

Ser Asp Asn Glu Asn Tyr Ala Ile Ala Ser Glu Tyr Leu Gly Gln Ser
             45                  50                  55

Ser Glu Asn Thr Asn Asn Thr Tyr Leu Thr Lys Asn Glu Leu Leu Ser
         60                  65                  70

Leu Ile Ala Tyr Ser Asn Asp Lys Asp Ile Leu Val Ile Pro Asp Ile
             75                  80                  85

Asp Leu Pro Ala His Ser Lys Gly Trp Leu Glu Leu Ile Lys Lys Lys
 90              95                  100

Asp Val Lys Leu Tyr Asn Asp Ile Val Thr Asp Tyr Ser Glu Glu Thr
105             110                 115                     120

Leu Asp Tyr Tyr Asp Asn Arg Val Ala Leu Asp Thr Val Asn Gln Leu
             125                 130                 135

Leu Asp Glu Val Leu Asp Leu Phe Tyr Gln Pro Lys Phe Glu Gly Lys
             140                 145                 150

Gln Arg Ile Val Leu Gly Gly Asp Glu Val Ser Gly Ser Glu Val His
             155                 160                 165

Gln Leu Asp Phe Ile Asp Phe Met Asn Gln Ile Ala Ser Thr Val Lys
170                 175                 180

Glu Ser Lys Tyr Glu Pro Gln Met Trp Asn Asp Ser Ile Thr Ser Glu
185                 190                 195                 200

Gly Ile Ala Asn Leu Asp Asp Ser Phe Ser Ile Leu Tyr Trp Gln Gln
             205                 210                 215

Ser Thr Leu Ser Ser Gly Glu Glu Ser Leu Asn Val Glu Asp Phe Glu
             220                 225                 230

Asn Trp Gly Phe Ser Val Tyr Asn Tyr Asn Ala Tyr Ser Leu Tyr Phe
             235                 240                 245

Leu Pro Ser Asn Gly Phe Thr Gln Glu Asp Ile Asn Glu Gln Met Asp
250                 255                 260

Tyr Met Asn Trp Ala Tyr Ala His Asn Lys Phe Tyr Ile Ser Asp
265                 270                 275                 280

Tyr Tyr His Ala Val Glu Thr Ser Asn Val Lys Gly Ser Ser Leu Thr
             285                 290                 295

Phe Trp Gly Glu His Ala Thr Asp Leu Ser Gln Lys Lys Leu Leu Lys
             300                 305                 310

Gln Glu Leu Pro Leu Ile Arg His Tyr Leu Asn Leu
             315                 320

<210> SEQ ID NO 14
<211> LENGTH: 1047
<212> TYPE: DNA
<213> ORGANISM: Terribacillus saccharophilus
<220> FEATURE:
<221> NAME/KEY: CDS
<222> LOCATION: (1)..(1044)
<220> FEATURE:
<221> NAME/KEY: sig_peptide
<222> LOCATION: (1)..(72)
<220> FEATURE:
<221> NAME/KEY: mat_peptide
```

<222> LOCATION: (73)..(1044)

<400> SEQUENCE: 14

| | | | | | | | | | | | | | | | | |
|---|---|---|---|---|---|---|---|---|---|---|---|---|---|---|---|---|
| ttg | att | aaa | ttt | ctt | tct | att | aca | aca | gtt | agt | ata | ctc | tta | ttt | cta | 48 |
| Leu | Ile | Lys | Phe | Leu | Ser | Ile | Thr | Thr | Val | Ser | Ile | Leu | Leu | Phe | Leu | |
| | -20 | | | | | | -15 | | | | | -10 | | | | |

| | | | | | | | | | | | | | | | | |
|---|---|---|---|---|---|---|---|---|---|---|---|---|---|---|---|---|
| act | atg | gcg | aat | aca | gta | cat | gca | aag | gat | caa | gag | aaa | ggg | att | tca | 96 |
| Thr | Met | Ala | Asn | Thr | Val | His | Ala | Lys | Asp | Gln | Glu | Lys | Gly | Ile | Ser | |
| | | -5 | | | | | -1 | 1 | | | | 5 | | | | |

| | | | | | | | | | | | | | | | | |
|---|---|---|---|---|---|---|---|---|---|---|---|---|---|---|---|---|
| atc | gat | att | tcg | aga | aaa | tat | tat | tct | atc | gga | aca | tta | aaa | gca | att | 144 |
| Ile | Asp | Ile | Ser | Arg | Lys | Tyr | Tyr | Ser | Ile | Gly | Thr | Leu | Lys | Ala | Ile | |
| | | 10 | | | | | 15 | | | | | 20 | | | | |

| | | | | | | | | | | | | | | | | |
|---|---|---|---|---|---|---|---|---|---|---|---|---|---|---|---|---|
| ata | gat | gaa | ata | agt | gca | aat | ggc | gga | gac | tac | tta | cag | ctg | cat | ttt | 192 |
| Ile | Asp | Glu | Ile | Ser | Ala | Asn | Gly | Gly | Asp | Tyr | Leu | Gln | Leu | His | Phe | |
| 25 | | | | | 30 | | | | | 35 | | | | | 40 | |

| | | | | | | | | | | | | | | | | |
|---|---|---|---|---|---|---|---|---|---|---|---|---|---|---|---|---|
| tca | gat | aat | gag | agc | tat | gca | att | gct | tct | gac | tat | ctt | ggt | cag | atc | 240 |
| Ser | Asp | Asn | Glu | Ser | Tyr | Ala | Ile | Ala | Ser | Asp | Tyr | Leu | Gly | Gln | Ile | |
| | | | | 45 | | | | | 50 | | | | | 55 | | |

| | | | | | | | | | | | | | | | | |
|---|---|---|---|---|---|---|---|---|---|---|---|---|---|---|---|---|
| agt | gat | act | cct | aac | aat | aca | tac | tta | acg | aaa | aat | gat | ctt | tta | tca | 288 |
| Ser | Asp | Thr | Pro | Asn | Asn | Thr | Tyr | Leu | Thr | Lys | Asn | Asp | Leu | Leu | Ser | |
| | | | 60 | | | | | 65 | | | | | 70 | | | |

| | | | | | | | | | | | | | | | | |
|---|---|---|---|---|---|---|---|---|---|---|---|---|---|---|---|---|
| ctt | ata | gca | tat | agc | aat | gat | aga | aat | ata | ctg | atc | att | ccc | gat | atg | 336 |
| Leu | Ile | Ala | Tyr | Ser | Asn | Asp | Arg | Asn | Ile | Leu | Ile | Ile | Pro | Asp | Met | |
| | 75 | | | | | 80 | | | | | 85 | | | | | |

| | | | | | | | | | | | | | | | | |
|---|---|---|---|---|---|---|---|---|---|---|---|---|---|---|---|---|
| gat | cta | cct | gcg | cat | tcc | aga | ggc | tgg | ttg | gag | tta | atg | aaa | gtg | aaa | 384 |
| Asp | Leu | Pro | Ala | His | Ser | Arg | Gly | Trp | Leu | Glu | Leu | Met | Lys | Val | Lys | |
| | 90 | | | | | 95 | | | | | 100 | | | | | |

| | | | | | | | | | | | | | | | | |
|---|---|---|---|---|---|---|---|---|---|---|---|---|---|---|---|---|
| gat | aga | gaa | tta | tat | act | gac | att | gta | acg | gat | tac | agt | aac | gag | aca | 432 |
| Asp | Arg | Glu | Leu | Tyr | Thr | Asp | Ile | Val | Thr | Asp | Tyr | Ser | Asn | Glu | Thr | |
| 105 | | | | | 110 | | | | | 115 | | | | | 120 | |

| | | | | | | | | | | | | | | | | |
|---|---|---|---|---|---|---|---|---|---|---|---|---|---|---|---|---|
| ctt | gat | tat | cat | aat | aat | aca | gat | gct | cta | aat | act | gcg | aat | cag | ctg | 480 |
| Leu | Asp | Tyr | His | Asn | Asn | Thr | Asp | Ala | Leu | Asn | Thr | Ala | Asn | Gln | Leu | |
| | | | | 125 | | | | | 130 | | | | | 135 | | |

| | | | | | | | | | | | | | | | | |
|---|---|---|---|---|---|---|---|---|---|---|---|---|---|---|---|---|
| tta | aat | gaa | ata | ctt | gaa | cta | ttt | tat | cag | cca | aag | ttt | gcg | ggg | aag | 528 |
| Leu | Asn | Glu | Ile | Leu | Glu | Leu | Phe | Tyr | Gln | Pro | Lys | Phe | Ala | Gly | Lys | |
| | | | 140 | | | | | 145 | | | | | 150 | | | |

| | | | | | | | | | | | | | | | | |
|---|---|---|---|---|---|---|---|---|---|---|---|---|---|---|---|---|
| cag | agg | ata | gta | ctt | ggc | gga | gat | gaa | gtg | cca | ggg | agt | gag | att | cat | 576 |
| Gln | Arg | Ile | Val | Leu | Gly | Gly | Asp | Glu | Val | Pro | Gly | Ser | Glu | Ile | His | |
| | 155 | | | | | 160 | | | | | 165 | | | | | |

| | | | | | | | | | | | | | | | | |
|---|---|---|---|---|---|---|---|---|---|---|---|---|---|---|---|---|
| cag | ttg | gat | ttc | att | cgt | ttt | att | aat | caa | atc | gcc | tcc | act | gct | aaa | 624 |
| Gln | Leu | Asp | Phe | Ile | Arg | Phe | Ile | Asn | Gln | Ile | Ala | Ser | Thr | Ala | Lys | |
| | 170 | | | | | 175 | | | | | 180 | | | | | |

| | | | | | | | | | | | | | | | | |
|---|---|---|---|---|---|---|---|---|---|---|---|---|---|---|---|---|
| gct | agc | aac | tat | gca | cca | cag | atg | tgg | aat | gat | agc | att | act | gca | gaa | 672 |
| Ala | Ser | Asn | Tyr | Ala | Pro | Gln | Met | Trp | Asn | Asp | Ser | Ile | Thr | Ala | Glu | |
| 185 | | | | | 190 | | | | | 195 | | | | | 200 | |

| | | | | | | | | | | | | | | | | |
|---|---|---|---|---|---|---|---|---|---|---|---|---|---|---|---|---|
| gga | att | cag | aat | ctg | gat | aaa | agc | ttc | tct | att | ctt | tat | tgg | aag | caa | 720 |
| Gly | Ile | Gln | Asn | Leu | Asp | Lys | Ser | Phe | Ser | Ile | Leu | Tyr | Trp | Lys | Gln | |
| | | | | 205 | | | | | 210 | | | | | 215 | | |

| | | | | | | | | | | | | | | | | |
|---|---|---|---|---|---|---|---|---|---|---|---|---|---|---|---|---|
| agt | acg | ctt | tca | aac | ggt | gca | caa | agt | cta | gaa | gta | caa | gac | ttt | gaa | 768 |
| Ser | Thr | Leu | Ser | Asn | Gly | Ala | Gln | Ser | Leu | Glu | Val | Gln | Asp | Phe | Glu | |
| | | | 220 | | | | | 225 | | | | | 230 | | | |

| | | | | | | | | | | | | | | | | |
|---|---|---|---|---|---|---|---|---|---|---|---|---|---|---|---|---|
| gac | tgg | gat | ttt | ccc | gta | tat | aac | tat | aat | gca | tat | tct | tta | tat | ttc | 816 |
| Asp | Trp | Asp | Phe | Pro | Val | Tyr | Asn | Tyr | Asn | Ala | Tyr | Ser | Leu | Tyr | Phe | |
| | | 235 | | | | | 240 | | | | | 245 | | | | |

| | | | | | | | | | | | | | | | | |
|---|---|---|---|---|---|---|---|---|---|---|---|---|---|---|---|---|
| tta | cct | tcc | atc | cgt | ttt | acc | gat | gaa | gat | ata | aca | gag | cag | atg | aac | 864 |
| Leu | Pro | Ser | Ile | Arg | Phe | Thr | Asp | Glu | Asp | Ile | Thr | Glu | Gln | Met | Asn | |
| | 250 | | | | | 255 | | | | | 260 | | | | | |

| | | | | | | | | | | | | | | | | |
|---|---|---|---|---|---|---|---|---|---|---|---|---|---|---|---|---|
| tat | atg | aaa | tgg | gct | tat | gca | tat | aat | aaa | ttt | ttc | tat | att | tca | gat | 912 |
| Tyr | Met | Lys | Trp | Ala | Tyr | Ala | Tyr | Asn | Lys | Phe | Phe | Tyr | Ile | Ser | Asp | |
| 265 | | | | | 270 | | | | | 275 | | | | | 280 | |

```
tac tat aag tcg gtg gac gca tct aac gta aaa ggg tct agc ttg acc      960
Tyr Tyr Lys Ser Val Asp Ala Ser Asn Val Lys Gly Ser Ser Leu Thr
            285                 290                 295 ttt tgg ggt gaa cac gca act gac tta agc caa gag gaa ttg ctt gag     1008
Phe Trp Gly Glu His Ala Thr Asp Leu Ser Gln Glu Glu Leu Leu Glu
        300                 305                 310 caa gaa ctg cct tta ata aaa aaa ttc tta agc tta taa                 1047
Gln Glu Leu Pro Leu Ile Lys Lys Phe Leu Ser Leu
            315                 320
```

<210> SEQ ID NO 15
<211> LENGTH: 348
<212> TYPE: PRT
<213> ORGANISM: Terribacillus saccharophilus

<400> SEQUENCE: 15

```
Leu Ile Lys Phe Leu Ser Ile Thr Thr Val Ser Ile Leu Leu Phe Leu
            -20                 -15                 -10

Thr Met Ala Asn Thr Val His Ala Lys Asp Gln Glu Lys Gly Ile Ser
         -5              -1   1                   5

Ile Asp Ile Ser Arg Lys Tyr Tyr Ser Ile Gly Thr Leu Lys Ala Ile
     10                  15                  20

Ile Asp Glu Ile Ser Ala Asn Gly Gly Asp Tyr Leu Gln Leu His Phe
 25                  30                  35                  40

Ser Asp Asn Glu Ser Tyr Ala Ile Ala Ser Asp Tyr Leu Gly Gln Ile
                 45                  50                  55

Ser Asp Thr Pro Asn Asn Thr Tyr Leu Thr Lys Asn Asp Leu Leu Ser
             60                  65                  70

Leu Ile Ala Tyr Ser Asn Asp Arg Asn Ile Leu Ile Ile Pro Asp Met
         75                  80                  85

Asp Leu Pro Ala His Ser Arg Gly Trp Leu Glu Leu Met Lys Val Lys
     90                  95                 100

Asp Arg Glu Leu Tyr Thr Asp Ile Val Thr Asp Tyr Ser Asn Glu Thr
105                 110                 115                 120

Leu Asp Tyr His Asn Asn Thr Asp Ala Leu Asn Thr Ala Asn Gln Leu
                125                 130                 135

Leu Asn Glu Ile Leu Glu Leu Phe Tyr Gln Pro Lys Phe Ala Gly Lys
            140                 145                 150

Gln Arg Ile Val Leu Gly Gly Asp Glu Val Pro Gly Ser Glu Ile His
        155                 160                 165

Gln Leu Asp Phe Ile Arg Phe Ile Asn Gln Ile Ala Ser Thr Ala Lys
    170                 175                 180

Ala Ser Asn Tyr Ala Pro Gln Met Trp Asn Asp Ser Ile Thr Ala Glu
185                 190                 195                 200

Gly Ile Gln Asn Leu Asp Lys Ser Phe Ser Ile Leu Tyr Trp Lys Gln
                205                 210                 215

Ser Thr Leu Ser Asn Gly Ala Gln Ser Leu Glu Val Gln Asp Phe Glu
            220                 225                 230

Asp Trp Asp Phe Pro Val Tyr Asn Tyr Asn Ala Tyr Ser Leu Tyr Phe
        235                 240                 245

Leu Pro Ser Ile Arg Phe Thr Asp Glu Asp Ile Thr Glu Gln Met Asn
    250                 255                 260

Tyr Met Lys Trp Ala Tyr Ala Tyr Asn Lys Phe Phe Tyr Ile Ser Asp
265                 270                 275                 280

Tyr Tyr Lys Ser Val Asp Ala Ser Asn Val Lys Gly Ser Ser Leu Thr
```

```
                    285                 290                 295
Phe Trp Gly Glu His Ala Thr Asp Leu Ser Gln Glu Glu Leu Leu Glu
                300                 305                 310

Gln Glu Leu Pro Leu Ile Lys Lys Phe Leu Ser Leu
        315                 320
```

<210> SEQ ID NO 16
<211> LENGTH: 27
<212> TYPE: PRT
<213> ORGANISM: Artificial
<220> FEATURE:
<223> OTHER INFORMATION: Bacillus clausii signal peptide

<400> SEQUENCE: 16

```
Met Lys Lys Pro Leu Gly Lys Ile Val Ala Ser Thr Ala Leu Leu Ile
1               5                   10                  15

Ser Val Ala Phe Ser Ser Ser Ile Ala Ser Ala
                20                  25
```

<210> SEQ ID NO 17
<211> LENGTH: 8
<212> TYPE: PRT
<213> ORGANISM: Artificial
<220> FEATURE:
<223> OTHER INFORMATION: His-tag

<400> SEQUENCE: 17

```
His His His His His His Pro Arg
1               5
```

<210> SEQ ID NO 18
<211> LENGTH: 4
<212> TYPE: PRT
<213> ORGANISM: Artificial
<220> FEATURE:
<223> OTHER INFORMATION: Polypeptide motif in some hexosaminidases of
      the invention
<220> FEATURE:
<221> NAME/KEY: MISC_FEATURE
<222> LOCATION: (2)..(2)
<223> OTHER INFORMATION: Xaa = any natural amino acids

<400> SEQUENCE: 18

```
Gly Xaa Asp Glu
1
```

<210> SEQ ID NO 19
<211> LENGTH: 7
<212> TYPE: PRT
<213> ORGANISM: Artificial
<220> FEATURE:
<223> OTHER INFORMATION: Polypeptide motif in some hexosaminidases of
      the invention
<220> FEATURE:
<221> NAME/KEY: MISC_FEATURE
<222> LOCATION: (1)..(1)
<223> OTHER INFORMATION: Xaa = E (Glu) or Q (Gln)
<220> FEATURE:
<221> NAME/KEY: MISC_FEATURE
<222> LOCATION: (2)..(2)
<223> OTHER INFORMATION: Xaa = N (Asn) or R (Arg) or S (Ser) or H (His)
      or A (Ala)
<220> FEATURE:
<221> NAME/KEY: MISC_FEATURE
<222> LOCATION: (3)..(3)
<223> OTHER INFORMATION: Xaa = Y (Tyr) or V (Val) or F (Phe) or L (Leu)
<220> FEATURE:
<221> NAME/KEY: MISC_FEATURE
<222> LOCATION: (4)..(4)

```
<223> OTHER INFORMATION: Xaa = A(Ala) or G(Gly) or S (Ser) or T (Thr) or
      C (Cys)
<220> FEATURE:
<221> NAME/KEY: MISC_FEATURE
<222> LOCATION: (5)..(5)
<223> OTHER INFORMATION: Xaa = I (Ile) or V (Val) or L (Leu) or F (Phe)
<220> FEATURE:
<221> NAME/KEY: MISC_FEATURE
<222> LOCATION: (6)..(6)
<223> OTHER INFORMATION: Xaa = E (Glu) or A (Ala) or Q (Gln) or Y (Tyr)
      or N (Asn)
<220> FEATURE:
<221> NAME/KEY: MISC_FEATURE
<222> LOCATION: (7)..(7)
<223> OTHER INFORMATION: Xaa = S (Ser) or N (Asn)

<400> SEQUENCE: 19

Xaa Xaa Xaa Xaa Xaa Xaa Xaa
1               5

<210> SEQ ID NO 20
<211> LENGTH: 8
<212> TYPE: PRT
<213> ORGANISM: Artificial
<220> FEATURE:
<223> OTHER INFORMATION: Polypeptide motif in some hexosaminidases of
      the invention
<220> FEATURE:
<221> NAME/KEY: MISC_FEATURE
<222> LOCATION: (1)..(1)
<223> OTHER INFORMATION: Xaa = V (Val) or I (Ile) or M (Met)
<220> FEATURE:
<221> NAME/KEY: MISC_FEATURE
<222> LOCATION: (2)..(2)
<223> OTHER INFORMATION: Xaa = L (Leu) or I (Ile) or V (Val)
<220> FEATURE:
<221> NAME/KEY: MISC_FEATURE
<222> LOCATION: (4)..(4)
<223> OTHER INFORMATION: Xaa = G (Gly) or A (Ala) or V (Val)
<220> FEATURE:
<221> NAME/KEY: MISC_FEATURE
<222> LOCATION: (7)..(7)
<223> OTHER INFORMATION: Xaa = V (Val) or I (Ile)
<220> FEATURE:
<221> NAME/KEY: MISC_FEATURE
<222> LOCATION: (8)..(8)
<223> OTHER INFORMATION: Xaa = P (Pro) or S (Ser) or A (Ala)

<400> SEQUENCE: 20

Xaa Xaa Gly Xaa Asp Glu Xaa Xaa
1               5

<210> SEQ ID NO 21
<211> LENGTH: 6
<212> TYPE: PRT
<213> ORGANISM: Artificial
<220> FEATURE:
<223> OTHER INFORMATION: Polypeptide motif in some hexosaminidases of
      the invention
<220> FEATURE:
<221> NAME/KEY: MISC_FEATURE
<222> LOCATION: (4)..(4)
<223> OTHER INFORMATION: Xaa = S (Ser) or Q (Gln) or R (Arg)
<220> FEATURE:
<221> NAME/KEY: MISC_FEATURE
<222> LOCATION: (5)..(5)
<223> OTHER INFORMATION: Xaa = I (Ile) or V (Val) or L (Leu)
<220> FEATURE:
<221> NAME/KEY: MISC_FEATURE
<222> LOCATION: (6)..(6)
<223> OTHER INFORMATION: Xaa = T (Thr) or L (Leu) or V (Val) or M (Met)

<400> SEQUENCE: 21

Trp Asn Asp Xaa Xaa Xaa
```

-continued

```
<210> SEQ ID NO 22
<211> LENGTH: 4
<212> TYPE: PRT
<213> ORGANISM: Artificial
<220> FEATURE:
<223> OTHER INFORMATION: Polypeptide motif in some hexosaminidases of
      the invention

<400> SEQUENCE: 22

Gln Ser Thr Leu
1

<210> SEQ ID NO 23
<211> LENGTH: 5
<212> TYPE: PRT
<213> ORGANISM: Artificial
<220> FEATURE:
<223> OTHER INFORMATION: Polypeptide motif in some hexosaminidases of
      the invention

<400> SEQUENCE: 23

Asn Lys Phe Phe Tyr
1               5

<210> SEQ ID NO 24
<211> LENGTH: 5
<212> TYPE: PRT
<213> ORGANISM: Artificial
<220> FEATURE:
<223> OTHER INFORMATION: Polypeptide motif in some hexosaminidases of
      the invention
<220> FEATURE:
<221> NAME/KEY: MISC_FEATURE
<222> LOCATION: (4)..(4)
<223> OTHER INFORMATION: Xaa = D (Asp) or R (Arg)

<400> SEQUENCE: 24

Asn Leu Asp Xaa Ser
1               5
```

DETERGENT COMPOSITIONS AND USES THEREOF

CROSS-REFERENCE TO RELATED APPLICATIONS

This application is a continuation of U.S. application Ser. No. 16/094,740 filed on Oct. 18, 2018, now U.S. Pat. No. 10,626,354, which is a 35 U.S.C. 371 national application of international application no. PCT/EP2017/060265 filed Apr. 28, 2017, which claims priority or the benefit under 35 U.S.C. 119 of Danish application no. PA 2016 00262 filed Apr. 29, 2016. The content of each application is fully incorporated herein by reference.

REFERENCE TO A SEQUENCE LISTING

This application contains a Sequence Listing in computer readable form, which is incorporated herein by reference.

BACKGROUND OF THE INVENTION

Field of the Invention

The present invention relates to polypeptides having hexosaminidase activity, polynucleotides encoding the polypeptides and catalytic domains belonging to the Glycoside Hydrolase family 20 (GH20, www.cazy.org). The invention further relates to compositions comprising such polypeptides in particular cleaning compositions, use of polypeptides having hexosaminidase activity in cleaning processes and/or for deep cleaning, methods for deep cleaning. The invention further relates to nucleic acid constructs, vectors, and host cells comprising the polynucleotides as well as methods of producing and using the polypeptides and catalytic domains.

Description of the Related Art

Polypeptides having hexosaminidase activity include Dispersins such as Dispersin B (DspB), which are described as β-N-acetylglucosamininidases belonging to the Glycoside Hydrolase 20 family. WO04061117 A2 (Kane Biotech INC) describe use of compositions comprising DspB for reducing and preventing biofilm caused by poly-N-acetylglucosamine-producing bacteria and Kane et al. describes the use of compositions comprising dispersins for reducing biofilm on medical devises and for wound care. Biofilm may also be present on laundry items, such as fabrics, other hard surfaces, such as dish wash utensils, dish washers and washing machines where they may cause malodor, which is difficult to remove even after wash. The application WO9850512 (Procter and Gamble) disclose laundry or cleaning products comprising one or more hexosaminidase enzymes. The present invention provides suitable enzymes for use in detergents and for deep cleaning of items such as laundry and cleaning process.

SUMMARY OF THE INVENTION

The present invention provides polypeptides belonging to the *Terribacillus* clade of hexosaminidases from the Glycoside Hydrolase 20 family. The *Terribacillus* clade is shown in FIGS. 1 and 3. The polypeptides of the invention have hexosaminidase activity. The invention further provides detergent compositions comprising polypeptides having hexosaminidase activity and the use of polypeptides having hexosaminidase activity for cleaning processes. The polypeptides of the present invention having hexosaminidase activity have beneficial properties such as removal and/or reduction of biofilm related components such as EPS and/or PNAG in cleaning processes. Including laundry and dish wash. The polypeptides of the present invention belong to the *Terribacillus* clade, which are homologous sequences of a particular clade of the Glycoside Hydrolase 20 family. Accordingly, the present invention relates to polypeptides having hexosaminidase activity selected from the group consisting of:
  (a) a polypeptide having at least 80% sequence identity to the mature polypeptide of SEQ ID NO 2, 4, 6, 13 or 15;
  (b) a variant of the mature polypeptide of SEQ ID NO 2, 4, 6, 13 or 15 comprising a substitution, deletion, and/or insertion at one or more (e.g., several) positions; and
  (c) a fragment of the polypeptide of (a) or (b) that has hexosaminidase activity.

The present invention also relates to polypeptides comprising a catalytic domain belonging to the Glycoside Hydrolase family 20 (GH20, www.cazy.org) and having at least 60% sequence identity to amino acids 1 to 324 of SEQ ID NO 2; at least 60% sequence identity to amino acids 1 to 324 of SEQ ID NO 4, at least 60% sequence identity to amino acids 1 to 324 of SEQ ID NO 6, at least 60% sequence identity to amino acids 1 to 324 of SEQ ID NO 13 or at least 60% sequence identity to amino acids 1 to 324 of SEQ ID NO 15. The present invention also relates to cleaning methods using the polypeptides of the present invention and to the use in cleaning processes. The invention further relates to a method for cleaning or laundering an item comprising the steps of:
  a. exposing an item to a wash liquor comprising a polypeptide having hexosaminidase activity selected from the group consisting of the polypeptides of SEQ ID NO 7, 8, 9, 10 and 11 or a polypeptide having at least 60% sequence identity hereto or a detergent composition comprising the polypeptides;
  b. Completing at least one wash cycle; and
  c. Optionally rinsing the item,
  wherein the item is a textile.

In addition is claimed the use of a polypeptide having hexosaminidase activity selected from the group consisting of the polypeptides of SEQ ID NO 7, 8, 9, 10, 11 or a polypeptide having at least 60% sequence identity for deep cleaning of an item.

The invention further relates to a composition comprising at least 0.001 ppm polypeptide having hexosaminidase activity, wherein the polypeptide is selected from the group consisting of polypeptides having at least 60% sequence identity to the mature polypeptide shown in SEQ ID NO 7, 8, 9, 10 and 11; and at least one adjunct ingredient. The invention further relates to the use of a composition of the invention for deep-cleaning of an item, wherein the item is a textile.

The invention further relates to a method for laundering an item comprising: a) expose an item to a wash liquor comprising a polypeptide selected from the group consisting of polypeptides shown in SEQ ID NO 7, SEQ ID NO 8, SEQ ID NO 9, SEQ ID NO 10 and SEQ ID NO 11 or a polypeptide having at least 60% sequence identity hereto or expose of an item to a detergent composition according to the invention; b) completing at least one wash cycle; and optionally rinsing the item, wherein the item is a textile.

The invention further relates to the use of a polypeptide or a composition of the invention, (i) for preventing, reducing or removing stickiness of the item;
(ii) for pretreating stains on the item;
(iii) for preventing, reducing or removing redeposition of soil during a wash cycle;
(iv) for preventing, reducing or removing adherence of soil to the item;
(v) for maintaining or improving whiteness of the item;
(vi) for preventing, reducing or removal malodor from the item, wherein the item is a textile.

BRIEF DESCRIPTION OF THE FIGURES

FIG. 2 An alignment of the polypeptides of the invention
FIG. 3 A phylogenetic tree of the polypeptides of the invention

OVERVIEW OF SEQUENCES OF THE TERRIBACILLUS CLADE

Figure 1:
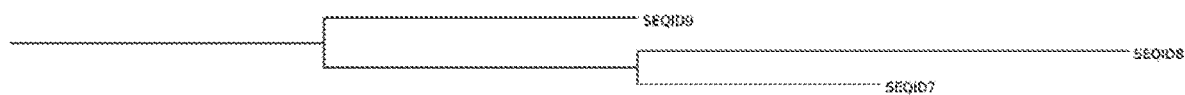
FIG. 1 Phylogenic tree showing the *Terribacillus* clade.

SEQ ID NO 1 is the DNA encoding the full-length polypeptide from *Terribacillus saccharophilus*
SEQ ID NO 2 is the polypeptide derived from SEQ ID NO 1
SEQ ID NO 3 is the DNA encoding the full-length polypeptide from *Terribacillus goriensis*
SEQ ID NO 4 is the polypeptide derived from SEQ ID NO 3
SEQ ID NO 5 is the DNA encoding the full-length polypeptide from *Terribacillus saccharophilus*
SEQ ID NO 6 is the polypeptide derived from SEQ ID NO 5
SEQ ID NO 7 is the mature polypeptide of SEQ ID NO 2
SEQ ID NO 8 is the mature polypeptide of SEQ ID NO 4
SEQ ID NO 9 is the mature polypeptide of SEQ ID NO 6
SEQ ID NO 10 is the mature polypeptide of SEQ ID NO 13
SEQ ID NO 11 is the mature polypeptide of SEQ ID NO 15
SEQ ID NO 12 is the DNA encoding the full-length polypeptide from *Terribacillus saccharophilus*
SEQ ID NO 13 is the polypeptide derived from SEQ ID NO 12
SEQ ID NO 14 is the DNA encoding the full-length polypeptide from *Terribacillus saccharophilus*
SEQ ID NO 15 is the polypeptide derived from SEQ ID NO 14
SEQ ID NO 16 is the *Bacillus clausii* secretion signal
SEQ ID NO 17 is a His-tag sequence
SEQ ID NO 18 is the polypeptide motif GXDE
SEQ ID NO 19 is the polypeptide motif [EQ][NRSHA][YVFL][AGSTC][IVLF][EAQYN][SN]
SEQ ID NO 20 is the polypeptide motif [VIM][LIV]G[GAV]DE[VI][PSA]
SEQ ID NO 21 is the polypeptide motif WND[SQR][IVL][TLVM]
SEQ ID NO 22 is the polypeptide motif QSTL
SEQ ID NO 23 is the polypeptide motif NKFFY
SEQ ID NO 24 is the polypeptide motif NLD[DR]S Definitions Dispersin: The term "dispersin" and the abbreviation "Dsp" means a polypeptide having hexosaminidase activity, EC 3.2.1.- that catalyzes the hydrolysis of β-1,6-glycosidic linkages of N-acetyl-glucosamine polymers (poly-N-acetyl-glucosamine) found e.g. in biofilm.

Hexosaminidase: The term "hexosaminidases" means a polypeptide having hexosaminidase activity (hexosaminidases), and includes EC 3.2.1.e.g. that catalyzes the hydrolysis of N-acetyl-D-hexosamine or N-acetyl-glucosamine polymers found e.g. in biofilm. The term includes dispersins and includes polypeptides having N-acetylglucosaminidase activity and β-N-acetylglucosamininidase activity. The term "polypeptide having hexosaminidase activity" may be used interchangeably with the term hexosaminidases and similar the term "polypeptide having β-N-acetylglucosaminidase activity" may be used interchangeably with the term β-N-acetylglucosamininidases. For the purposes of the present invention, hexosaminidase activity is determined according to the procedure described in Assay 1 or 2. In one aspect, the polypeptides of the present invention have at least 20%, e.g., at least 40%, at least 50%, at least 60%, at least 70%, at least 80%, at least 90%, at least 95%, or at least 100% of the hexosaminidase activity of the mature polypeptide of SEQ ID NO 2. In one aspect, the polypeptides of the present invention have at least 20%, e.g., at least 40%, at least 50%, at least 60%, at least 70%, at least 80%, at least 90%, at least 95%, or at least 100% of the hexosaminidase activity of the mature polypeptide of SEQ ID NO 4. In one aspect, the polypeptides of the present invention have at least 20%, e.g., at least 40%, at least 50%, at least 60%, at least 70%, at least 80%, at least 90%, at least 95%, or at least 100% of the hexosaminidase activity of the mature polypeptide of SEQ ID NO 6. In one aspect, the polypeptides of the present invention have at least 20%, e.g., at least 40%, at least 50%, at least 60%, at least 70%, at least 80%, at least 90%, at least 95%, or at least 100% of the hexosaminidase activity of the mature polypeptide of SEQ ID NO 13. In one aspect, the polypeptides of the present invention have at least 20%, e.g., at least 40%, at least 50%, at least 60%, at least 70%, at least 80%, at least 90%, at least 95%, or at least 100% of the hexosaminidase activity of the mature polypeptide of SEQ ID NO 15.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Biofilm: A biofilm may be produced by any group of microorganisms in which cells stick to each other or stick to a surface, such as a textile, dishware or hard surface or another kind of surface. These adherent cells are frequently embedded within a self-produced matrix of extracellular polymeric substance (EPS). Biofilm EPS is a polymeric conglomeration generally composed of extracellular DNA, proteins, and polysaccharides. Biofilms may form on living or non-living surfaces. The microbial cells growing in a biofilm are physiologically distinct from planktonic cells of the same organism, which, by contrast, are single-cells that may float or swim in a liquid medium. Bacteria living in a biofilm usually have significantly different properties from planktonic bacteria of the same species, as the dense and protected environment of the film allows them to cooperate and interact in various ways. One benefit of this environment for the microorganisms is increased resistance to detergents and antibiotics, as the dense extracellular matrix and the outer layer of cells protect the interior of the community. On laundry and hard surfaces biofilm producing bacteria can be found among the following species: *Acinetobacter* sp., *Aeromicrobium* sp., *Brevundimonas* sp., *Microbacterium* sp *Micrococcus luteus*, *Pseudomonas* sp., *Streptococcus* sp., *Streptococcus dysgalactiae*, *Staphylococcus epidermidis*, *Staphylococcus aureus*, *Staphylococcus pneumoniae*, *Stenotrophomonas* sp., *Enterobacter* sp., *Xanthomonas* sp., *Yersinia* sp., *Klebsiella* sp., *Burkholderia* sp., *Stenotrophomonas* sp., *Variovorax* sp., *Escherichia* sp., *Raistonia* sp., *Achromobacter* sp., *Luteibacter* sp., *Citrobacter* sp., *Xanthomonadaceae* sp., *Halomonas* sp., *Bordetella* sp., *Lysobacter* sp., *Serratia* sp., *Escherichia* sp., *Aggregatibacter* sp., *Listeria monocytogenes*, *Clostridium difficile*, *Mycobacterium* sp., *Neisseria gonorrheae*, *H. influenzae*, *Haemophilus ducreyi*, *Helicobacter pylori*, *Campylobacter jejuni* and *Enterococcus faecalis* as well as the fungi *Candida albicans*, *Aspergillus flavus*, *Fusarium solani*, and *Cryptococcus neoformans*. In one aspect, the biofilm component e.g. poly-N-acetylglucosamine comprising strain is *Brevundimonas* sp. In one aspect, the biofilm component e.g. poly-N-acetylglucosamine comprising strain is *Pseudomonas alcaliphila* or *Pseudomonas fluorescens*. In one aspect, the biofilm component e.g. poly-N-acetylglucosamine comprising strain is *Staphylococcus aureus*.

Catalytic domain: The term "catalytic domain" means the region of an enzyme containing the catalytic machinery of the enzyme.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Clade: a group of polypeptides clustered together based on homologous features traced to a common ancestor. Polypeptide clades can be visualized as phylogenetic trees and a clade is a group of polypeptides that consists of a common ancestor and all its lineal descendants (FIG. 1). The polypeptides of the invention e.g. all belong to the *Terribacillus* clade, which is illustrated as a phylogenetic tree in FIGS. 1 and 3. The *Terribacillus* clade or clade of *Terribacillus* is a group of enzymes all related to the same ancestor and share common properties. Polypeptides forming a group within the clade (a subclade) of the phylogenetic tree can also share common properties and are more closely related than other polypeptides in the clade.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Deep cleaning: By the term "deep cleaning" is meant reduction or removal of components of biofilm, such as EPS or parts hereof, polysaccharides, PNAG (poly-N-acetylglucosamine), proteins, DNA, soil or other components present in the biofilm.

Detergent adjunct ingredient: The detergent adjunct ingredient is different to the hexosaminidase of this invention. The precise nature of these additional adjunct components, and levels of incorporation thereof, will depend on the physical form of the composition and the nature of the operation for which it is to be used. Suitable adjunct materials include, but are not limited to the components described below such as surfactants, builders, flocculating aid, chelating agents, dye transfer inhibitors, enzymes, enzyme stabilizers, enzyme inhibitors, catalytic materials, bleach activators, hydrogen peroxide, sources of hydrogen peroxide, preformed peracids, polymeric agents, clay soil removal/anti-redeposition agents, brighteners, suds suppressors, dyes, perfumes, structure elasticizing agents, fabric softeners, carriers, hydrotropes, builders and co-builders, fabric huing agents, anti-foaming agents, dispersants, processing aids, and/or pigments.

Detergent Composition: The term "detergent composition" refers to compositions that find use in the removal of undesired compounds from items to be cleaned, such as textiles. The detergent composition may be used to e.g. clean textiles for both household cleaning and industrial cleaning. The terms encompass any materials/compounds selected for the cleaning composition desired and the form of the product (e.g., liquid, gel, powder, granulate, paste, or spray compositions) and includes, but is not limited to, detergent compositions (e.g., liquid and/or solid laundry detergents and fine fabric detergents; fabric fresheners; fabric softeners; and textile and laundry pre-spotters/pretreatment). In addition to containing the polypeptide of the invention, the composition may contain one or more additional enzymes (such as proteases, amylases, lipases, cutinases, cellulases, endoglucanases, xyloglucanases, pectinases, pectin lyases, xanthanases, peroxidases, haloperoxygenases, catalases and mannanases, or any mixture thereof), and/or detergent adjunct ingredients such as surfactants, builders, chelators or chelating agents, bleach system or bleach components, polymers, fabric conditioners, foam boosters, suds suppressors, dyes, perfume, tannish inhibitors, optical brighteners, bactericides, fungicides, soil suspending agents, anti-corrosion agents, enzyme inhibitors or stabilizers, enzyme activators, transferase(s), hydrolytic enzymes, oxido reductases, bluing agents and fluorescent dyes, antioxidants, and solubilizers.

Enzyme Detergency benefit: The term "enzyme detergency benefit" is defined herein as the advantageous effect an enzyme may add to a detergent compared to the same detergent without the enzyme. Important detergency benefits which can be provided by enzymes are stain removal with no or very little visible soils after washing and/or cleaning, prevention or reduction of redeposition of soils released in the washing process (an effect that also is termed anti-redeposition), restoring fully or partly the whiteness of textiles which originally were white but after repeated use and wash have obtained a greyish or yellowish appearance (an effect that also is termed whitening). Textile care benefits, which are not directly related to catalytic stain removal or prevention of redeposition of soils, are also important for enzyme detergency benefits. Examples of such textile care benefits are prevention or reduction of dye transfer from one fabric to another fabric or another part of the same fabric (an effect that is also termed dye transfer inhibition or anti-backstaining), removal of protruding or broken fibers from a fabric surface to decrease pilling tendencies or remove already existing pills or fuzz (an effect that also is termed anti-pilling), improvement of the fabric-softness, colour clarification of the fabric and removal of particulate soils which are trapped in the fibers of the fabric or garment. Enzymatic bleaching is a further enzyme detergency benefit where the catalytic activity generally is used to catalyze the formation of bleaching components such as hydrogen peroxide or other peroxides.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Fragment: The term "fragment" means a polypeptide or a catalytic domain having one or more (e.g., several) amino acids absent from the amino and/or carboxyl terminus of a mature polypeptide or domain; wherein the fragment has hexosaminidase activity. In one aspect, a fragment contains at least 300 amino acid residues (e.g., amino acids 1 to 300 of SEQ ID NO 2), at least 305 amino acid residues (e.g., amino acids 1 to 305 of SEQ ID NO 2), at least 310 amino acid residues (e.g., amino acids 1 to 310 of SEQ ID NO 2), at least 315 amino acid residues (e.g., amino acids 1 to 315 of SEQ ID NO 2), or at least 320 amino acid residues (e.g., amino acids 1 to 320 of SEQ ID NO 2). In one aspect, a fragment contains at least 300 amino acid residues (e.g., amino acids 1 to 300 of SEQ ID NO 4), at least 305 amino acid residues (e.g., amino acids 1 to 305 of SEQ ID NO 4), at least 310 amino acid residues (e.g., amino acids 1 to 310 of SEQ ID NO 4), at least 315 amino acid residues (e.g., amino acids 1 to 315 of SEQ ID NO 4), or at least 320 amino acid residues (e.g., amino acids 1 to 320 of SEQ ID NO 4). In one aspect, a fragment contains at least 300 amino acid residues (e.g., amino acids 1 to 300 of SEQ ID NO 6), at least 305 amino acid residues (e.g., amino acids 1 to 305 of SEQ ID NO 6), at least 310 amino acid residues (e.g., amino acids 1 to 310 of SEQ ID NO 6), at least 315 amino acid residues (e.g., amino acids 1 to 315 of SEQ ID NO 6), or at least 320 amino acid residues (e.g., amino acids 1 to 320 of SEQ ID NO 6). In one aspect, a fragment contains at least 300 amino acid residues (e.g., amino acids 1 to 300 of SEQ ID NO 13), at least 305 amino acid residues (e.g., amino acids 1 to 305 of SEQ ID NO 13), at least 310 amino acid residues (e.g., amino acids 1 to 310 of SEQ ID NO 13), at least 315 amino acid residues (e.g., amino acids 1 to 315 of SEQ ID NO 13), or at least 320 amino acid residues (e.g., amino acids 1 to 320 of SEQ ID NO 13). In one aspect, a fragment contains at least 300 amino acid residues (e.g., amino acids 1 to 300 of SEQ ID NO 15), at least 305 amino acid residues (e.g., amino acids 1 to 305 of SEQ ID NO 15), at least 310 amino acid residues (e.g., amino acids 1 to 310 of SEQ ID NO 15), at least 315 amino acid residues (e.g., amino acids 1 to 315 of SEQ ID NO 15), or at least 320 amino acid residues (e.g., amino acids 1 to 320 of SEQ ID NO 15).

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance). An isolated substance may be present in a fermentation broth sample; e.g. a host cell may be genetically modified to express the polypeptide of the invention. The fermentation broth from that host cell will comprise the isolated polypeptide.

Improved wash performance: The term "improved wash performance" is defined herein as an enzyme displaying an increased wash performance in a detergent composition relative to the wash performance of same detergent composition without the enzyme e.g. by increased stain removal or less re-deposition. The term "improved wash performance" includes wash performance in laundry.

Laundering: The term "laundering" relates to both household laundering and industrial laundering and means the process of treating textiles with a solution containing a cleaning or detergent composition of the present invention. The laundering process can for example be carried out using e.g. a household or an industrial washing machine or can be carried out by hand.

Malodor: By the term "malodor" is meant an odor which is not desired on clean items. The cleaned item should smell fresh and clean without malodors adhered to the item. One example of malodor is compounds with an unpleasant smell, which may be produced by microorganisms. Another example is unpleasant smells can be sweat or body odor adhered to an item which has been in contact with human or animal. Another example of malodor can be the odor from spices, which sticks to items for example curry or other exotic spices which smells strongly.

Mature polypeptide: The term "mature polypeptide" means a polypeptide in its final form following translation and any post-translational modifications, such as N-terminal processing, C-terminal truncation, glycosylation, phosphorylation, etc. In some aspects, the mature polypeptide is amino acids 1 to 324 of SEQ ID NO 2 and amino acids −41 to −1 of SEQ ID NO 2 are a signal peptide. In some aspects, the mature polypeptide is the amino acid sequence having SEQ ID NO 7. In some aspects, the mature polypeptide is amino acids 1 to 324 of SEQ ID NO 4 and amino acids −25 to −1 of SEQ ID NO 4 are a signal peptide. In some aspects, the mature polypeptide is the amino acid sequence having SEQ ID NO 8. In some aspects, the mature polypeptide is amino acids 1 to 324 of SEQ ID NO 6 and amino acids −25 to −1 of SEQ ID NO 6 are a signal peptide. In some aspects, the mature polypeptide is the amino acid sequence having SEQ ID NO 9. In some aspects, the mature polypeptide is amino acids 1 to 324 of SEQ ID NO 13 and amino acids −24 to −1 of SEQ ID NO 13 are a signal peptide. In some aspects, the mature polypeptide is the amino acid sequence having SEQ ID NO 10. In some aspects, the mature polypeptide is amino acids 1 to 324 of SEQ ID NO 15 and amino acids −24 to −1 of SEQ ID NO 15 are a signal peptide. In some aspects, the mature polypeptide is the amino acid sequence having SEQ ID NO 11.

It is known in the art that a host cell may produce a mixture of two of more different mature polypeptides (i.e., with a different C-terminal and/or N-terminal amino acid) expressed by the same polynucleotide. It is also known in the art that different host cells process polypeptides differently, and thus, one host cell expressing a polynucleotide may produce a different mature polypeptide (e.g., having a different C-terminal and/or N-terminal amino acid) as compared to another host cell expressing the same polynucleotide.

Mature polypeptide coding sequence: The term "mature polypeptide coding sequence" means a polynucleotide that encodes a mature polypeptide having hexosaminidase activity. In one aspect, the mature polypeptide coding sequence is nucleotides 124 to 1095 of SEQ ID NO 1 and nucleotides 1 to 123 of SEQ ID NO 1 encodes a signal peptide. In one aspect, the mature polypeptide coding sequence is nucleotides 76 to 1047 of SEQ ID NO 3 and nucleotides 1 to 75 of SEQ ID NO 3 encode a signal peptide. In one aspect, the mature polypeptide coding sequence is nucleotides 76 to 1047 of SEQ ID NO 5 and nucleotides 1 to 75 of SEQ ID NO 5 encode a signal peptide. In one aspect, the mature polypeptide coding sequence is nucleotides 73 to 1044 of SEQ ID NO 12 and nucleotides 1 to 72 of SEQ ID NO 12 encode a signal peptide. In one aspect, the mature polypeptide coding sequence is nucleotides 73 to 1044 of SEQ ID NO 14 and nucleotides 1 to 72 of SEQ ID NO 14 encode a signal peptide.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

$$(\text{Identical Residues} \times 100)/(\text{Length of Alignment} - \text{Total Number of Gaps in Alignment})$$

Stringency conditions: The term "very low stringency conditions" means for probes of at least 100 nucleotides in length, pre-hybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 45° C.

The term "low stringency conditions" means for probes of at least 100 nucleotides in length, pre-hybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

The term "medium stringency conditions" means for probes of at least 100 nucleotides in length, pre-hybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

The term "medium-high stringency conditions" means for probes of at least 100 nucleotides in length, pre-hybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 60° C.

The term "high stringency conditions" means for probes of at least 100 nucleotides in length, pre-hybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

The term "very high stringency conditions" means for probes of at least 100 nucleotides in length, pre-hybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.]

Variant: The term "variant" means a polypeptide having hexosaminidase activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position.

Nomenclature

For purposes of the present invention, the nomenclature [IV] or [I/V] means that the amino acid at this position may be isoleucine (Ile, I) or valine (Val, V). Likewise, the nomenclature [LVI] and [L/V/I] means that the amino acid at this position may be a leucine (Leu, L), valine (Val, V) or isoleucine (Ile, I), and so forth for other combinations as described herein. Unless otherwise limited further, the amino acid X is defined such that it may be any of the 20 natural amino acids.

DETAILED DESCRIPTION OF THE INVENTION

Various enzymes have been used in laundry many of which relate to removal of malodor. WO2014/087011 describes the use of a deoxyribonuclease (DNase) for reducing malodor from laundry and/or textile, WO9909143 describes the use of one or more oxidoreductases in combination with a mediator for the reduction of malodor and WO2012/112718 describe a method for inhibiting production of laundry malodor caused by bacteria by using various strains of Bacillus. The present invention relates to polypeptides and cleaning e.g. detergent compositions comprising polypeptides from the Terribacillus clade of GH20 family of polypeptides having hexosaminidase activity. Also claimed are laundering methods and the use of the polypeptides with hexosaminidase activity. The polypeptides from the Terribacillus clade of GH20 family with hexosaminidase activity are useful in reducing and preventing staining of items being washed. The inventors have surprisingly found that the polypeptides of the Terribacillus clade of GH20 family having hexosaminidase activity are useful for reduction of laundry associated organic matter e.g. EPS and or PNAG. WO200406117 describes compositions comprising dispersins e.g. DspB. The composition may include a detergent which may be anionic, cationic, or non-ionic. WO9850512 describes enzymes having hexosaminidase activity. The polypeptides of the present invention have hexosaminidase activity however, these do not belong to the DspB clade or to is related to any of the enzymes described in WO9850512. The polypeptides of the invention belong to the Terribacillus clade and are thus distinct from the DspB and from those disclosed in WO9850512. It was therefore surprising that the polypeptide of the invention could be used for prevention, reduction and/or removal of organic matter such as biofilm components e.g. polysaccharides e.g. PNAG (poly-N-acetylglucosamine) on hard surfaces as well as in laundry. There is no indication in the art of the use of hexosaminidases in cleaning processes such as laundry or in detergent compositions comprising e.g. builders and/or bleaches. To be useful in cleaning processes the enzymes need to perform its action in detergents under the conditions of cleaning processes such as laundry, which includes stability in the presence of detergent components such as surfactants, builders and bleach components. The components of a detergent may significantly effect on the performance of the enzymes such as the hexosaminidases. The present application surprisingly shows that polypeptides belonging to the Terribacillus clade are particularly stable in the present of surfactant linear alkylbenzenesulfonates (LAS) which is a very common surfactant in detergents. The polypeptides belonging to the Terribacillus are thus particularly useful for deep cleaning e.g. of textiles or washing machines.

An overview of the Terribacillus clade is provided in FIG. 1. The Terribacillus clade comprises homologous sequences. The polypeptides with hexosaminidase activity of the present invention having the mature amino acid sequences SEQ ID 7, 8 and 9 can be pairwise aligned using the Needleman-Wunsch algorithm (Needleman and Wunsch, 1970, J. Mol. Biol. 48: 443-453). The percent identities resulting from such alignments are shown in Table 1 below.

TABLE 1

| SEQ ID NO 11 | SEQ ID NO 10 | SEQ ID NO 7 | SEQ ID NO 9 | SEQ ID NO 8 | |
|---|---|---|---|---|---|
| 100 | 75.9 | 81.8 | 82.4 | 81.2 | SEQ ID NO 11 |
| 75.9 | 100 | 77.5 | 76.5 | 77.5 | SEQ ID NO 10 |
| 81.8 | 77.5 | 100 | 95.1 | 95.7 | SEQ ID NO 7 |
| 82.4 | 76.5 | 95.1 | 100 | 93.5 | SEQ ID NO 9 |
| 81.2 | 77.5 | 95.7 | 93.5 | 100 | SEQ ID NO 8 |

Table 1 shows that the polypeptides of the invention share close sequence relatedness. The polypeptides comprising the amino acids sequences of SEQ ID NO 7, SEQ ID NO 8, SEQ ID NO 9, SEQ ID NO 10 and SEQ ID NO 11 belongs to a subclade of the Dispersin clade. These polypeptides share more than 90% pairwise sequence identity and are closer related to each other compared to e.g. the DspB polypeptides which lies further away (not shown).

One aspect of the invention relates to a polypeptide comprising the amino acid sequence shown in SEQ ID NO 7 or is a polypeptide having at least 99.8% or 100% sequence identity hereto, wherein the polypeptide has hexosaminidase activity.

One aspect of the invention relates to a polypeptide comprising the amino acid sequence shown in SEQ ID NO 8 or is a polypeptide having at least 96%, such as at least 97%, such as at least 98%, such as at least 99% or 100% sequence identity hereto, wherein the polypeptide has hexosaminidase activity.

One aspect of the invention relates to a polypeptide comprising the amino acid sequence shown in SEQ ID NO 9 or is a polypeptide having at least 95%, such as at least 96%, such as at least 97%, such as at least 98%, such as at least 99% or 100% sequence identity hereto, wherein the polypeptide has hexosaminidase activity.

One aspect of the invention relates to a polypeptide comprising the amino acid sequence shown in SEQ ID NO 10 or is a polypeptide having at least 96%, such as at least 97%, such as at least 98%, such as at least 99% or 100% sequence identity hereto, wherein the polypeptide has hexosaminidase activity.

One aspect of the invention relates to a polypeptide comprising the amino acid sequence shown in SEQ ID NO 11 or is a polypeptide having at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99% or 100% sequence identity hereto, wherein the polypeptide has hexosaminidase activity.

The polypeptides of the invention all lies within the same clade, the Terribacillus clade, and all have common functional features including deep cleaning properties in the presence of detergents. The inventors have surprisingly found that the polypeptides of the Terribacillus clade comprising the mature polypeptides with SEQ ID NO 7, 8, 9, 10, 11 or polypeptides having at least 80% sequence identity hereto, share specific properties, more precisely the polypeptides comprised by this clade all have good deep cleaning effects with a broad range of surfactants such as LAS and are therefore particularly useful in detergents with surfactants, such as in detergent comprising anionic, non-ionic, cationic and/or amphoteric surfactants.

Figure 2:
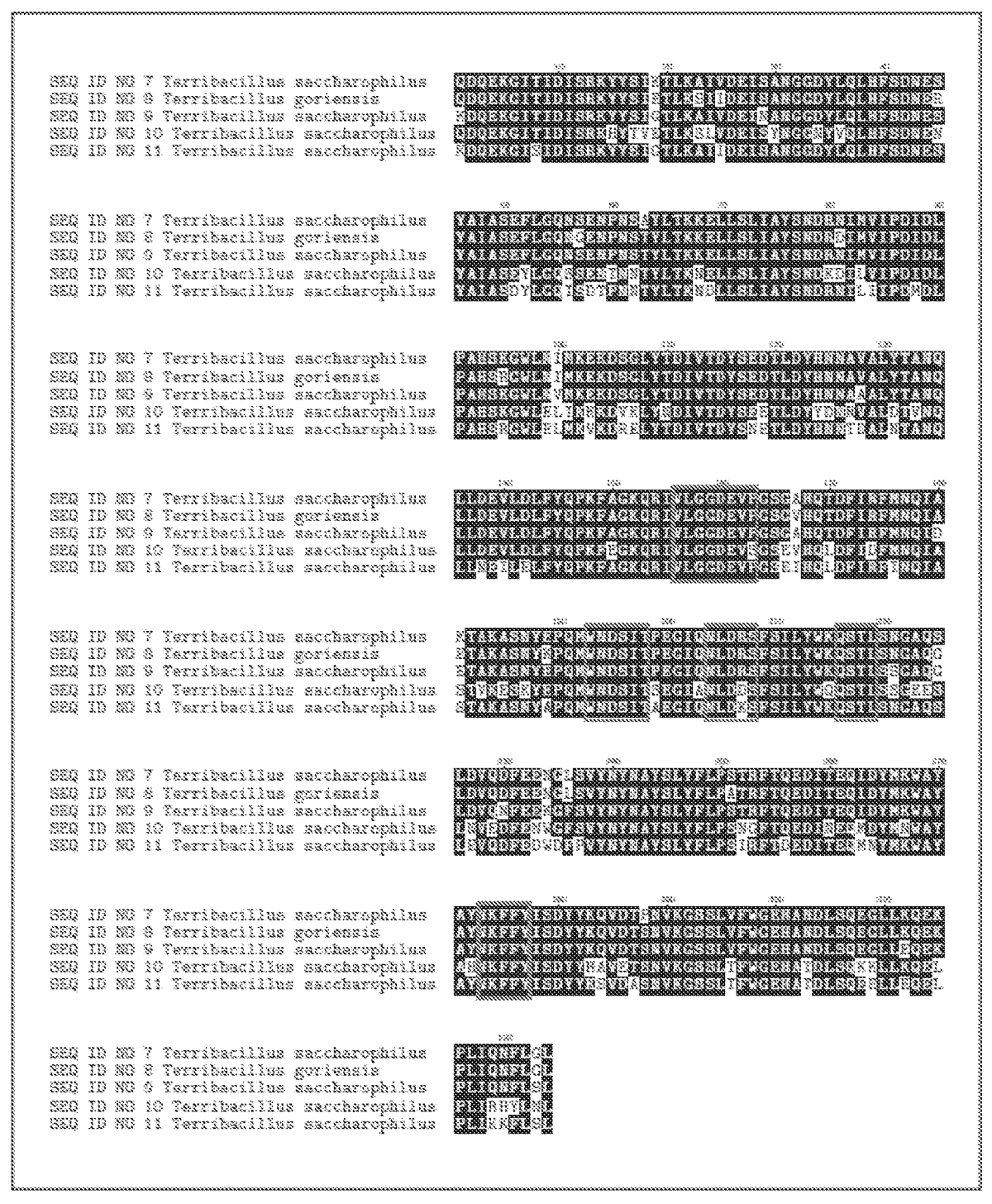

As already described the polypeptides of the invention having hexosaminidase activity may comprise the structural domains of Glyco_hydro_20 e.g. GH20. Polypeptides comprising a GH20 domain may comprise several motifs one example is GXDE (SEQ ID NO 18) situated in positions corresponding to positions 158 to 161 in *Terribacillus saccharophilus* (SEQ ID NO 9). Residues D and E are the key catalytic residues of GH20 (pos 160 and 161 in SEQ ID NO 9). The GH20 polypeptides can be separated into multiple distinct sub-clusters, or clades, examples of specific domains are listed below. A further domain, preferably shared by the polypeptides of the invention, was identified. This domain has not been described previously, the domain is termed IAS and polypeptides of this domain are in addition to having hexosaminidase activity e.g. PNAG activity, characterized by comprising certain motifs e.g. one or more of the [EQ][NRSHA][YVFL][AGSTC][IVLF][EAQYN][SN] (SEQ ID NO 19), corresponding to ESYAIAS at position 44 to 50 of SEQ ID NO 9. Another domain, preferably shared by the polypeptides of the invention, was identified. This domain has not been described previously. The domain is termed WND and polypeptides of this domain comprise GH20 domain, are of bacterial origin and are in addition to having PNAG activity, characterized by comprising certain motifs. The polypeptides of the domain may comprise the motif [VIM][LIV]G[GAV]DE[VI][PSA] (SEQ ID NO: 20), corresponding to pos 156 to 163 of SEQ ID NO 9, where G (corresponding to position 158 of SEQ ID NO 9) is fully conserved in *Terribacillus* clade and residues D and E are the key catalytic residues of GH20 (pos 160 and 161 in SEQ ID NO 9). Another motif which may be comprised by the polypeptides of the invention is WND[SQR][IVL][TLVM] (SEQ ID NO: 21), 193 to 198 in SEQ ID NO 9, where W (pos 193 in SEQ ID NO 9) is part of the active site pocket and putatively involved in binding of the N-acetyl group of the PNAG substrate. The polypeptides of the *Terribacillus* clade may be further subdivided in a clade termed QSTL, which comprises WND domain polypeptides of bacterial origin, having PNAG activity. The polypeptides of the clade comprise the motif example QSTL (SEQ ID NO: 22), corresponding to pos 216 to 219 of SEQ ID NO 9, where all four amino are fully conserved in QSTL clade and putatively involved in substrate binding. Another motif which may be comprised by the polypeptides of the QSTL clade is NKFFY (SEQ ID NO: 23), 273 to 277 in SEQ ID NO 9. A further motif which may be comprised by the polypeptides of the QSTL clade is NLD[DR]S (SEQ ID NO: 24), 204 to 208 in SEQ ID NO 9. In one aspect, the polypeptides of the invention comprise the GXDE (SEQ ID NO 18) motif. In one aspect, the polypeptides of the invention comprise the [EQ][NRSHA][YVFL][AGSTC][IVLF][EAQYN][SN] (SEQ ID NO 19) motif. In one aspect, the polypeptides of the invention comprise the motif [VIM][LIV]G[GAV]DE[VI][PSA] (SEQ ID NO: 20). In one aspect, the polypeptides of the invention comprise the motif WND[SQR][IVL][TLVM] (SEQ ID NO: 21). In one aspect, the polypeptides of the invention comprise the motif QSTL (SEQ ID NO 22). In one aspect, the polypeptides of the invention comprise the motif NKFFY (SEQ ID NO: 23). In one aspect, the polypeptides of the invention comprise the motif NLD[DR]S (SEQ ID NO: 24). An alignment of the polypeptides of the invention comprised in the QSTL clade is shown in FIG. 2.

Some aspect of the invention relates to a polypeptide comprising one or both motif(s) GXDE (SEQ ID NO 18) or [EQ][NRSHA][YVFL][AGSTC][IVLF][EAQYN][SN] (SEQ ID NO 19), wherein the polypeptide comprises an amino acid sequence selected from the polypeptides shown in SEQ ID NOS 7, 8, 9, 10 and 11 or polypeptides having at least 80% sequence identity hereto.

Some aspect of the invention relates to a polypeptide comprising one or both motif(s) [VIM][LIV]G[GAV]DE[VI][PSA] (SEQ ID NO 20) or WND[SQR][IVL][TLVM] (SEQ ID NO 21), wherein the polypeptide comprises an amino acid sequence selected from the polypeptides shown in SEQ ID NOS 7, 8, 9, 10 and 11 or polypeptides having at least 80% sequence identity hereto.

Some aspect of the invention relates to a polypeptide comprising one or more of the motif(s) QSTL (SEQ ID NO 22), NKFFY (SEQ ID NO: 23) or NLD[DR]S (SEQ ID NO: 24), wherein the polypeptide comprises an amino acid sequence selected from the polypeptides shown in SEQ ID NOS 7, 8, 9, 10 and 11 or polypeptides having at least 80% sequence identity hereto.

One aspect of the invention relates to a polypeptide comprising one or both motif(s) [VIM][LIV]G[GAV]DE[VI][PSA] (SEQ ID NO 20) or WND[SQR][IVL][TLVM] (SEQ ID NO 21), wherein the polypeptide comprises the amino acid sequence shown in SEQ ID NO 7 or is a polypeptide having at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99% or 100% sequence identity hereto, wherein the polypeptide has hexosaminidase activity.

One aspect of the invention relates to a polypeptide comprising one or both motif(s) [VIM][LIV]G[GAV]DE[VI][PSA] (SEQ ID NO 20) or WND[SQR][IVL][TLVM] (SEQ ID NO 21), wherein the polypeptide comprises the amino acid sequence shown in SEQ ID NO 8 or is a polypeptide having at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99% or 100% sequence identity hereto, wherein the polypeptide has hexosaminidase activity.

One aspect of the invention relates to a polypeptide comprising one or both motif(s) [VIM][LIV]G[GAV]DE[VI][PSA] (SEQ ID NO 20) or WND[SQR][IVL][TLVM] (SEQ ID NO 21), wherein the polypeptide comprises the amino acid sequence shown in SEQ ID NO 9 or is a polypeptide having at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99% or 100% sequence identity hereto, wherein the polypeptide has hexosaminidase activity.

One aspect of the invention relates to a polypeptide comprising one or both motif(s) [VIM][LIV]G[GAV]DE[VI][PSA] (SEQ ID NO 20) or WND[SQR][IVL][TLVM] (SEQ ID NO 21), wherein the polypeptide comprises the amino acid sequence shown in SEQ ID NO 10 or is a polypeptide having at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99% or 100% sequence identity hereto, wherein the polypeptide has hexosaminidase activity.

One aspect of the invention relates to a polypeptide comprising one or both motif(s) [VIM][LIV]G[GAV]DE[VI][PSA] (SEQ ID NO 20) or WND[SQR][IVL][TLVM] (SEQ ID NO 21), wherein the polypeptide comprises the amino acid sequence shown in SEQ ID NO 11 or is a polypeptide having at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99% or 100% sequence identity hereto, wherein the polypeptide has hexosaminidase activity.

One aspect of the invention relates to a polypeptide comprising one or more of the motif(s) QSTL (SEQ ID NO 22), NKFFY (SEQ ID NO: 23) or NLD[DR]S (SEQ ID NO: 24), wherein the polypeptide comprises the amino acid sequence shown in SEQ ID NO 7 or is a polypeptide having at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99% or 100% sequence identity hereto, wherein the polypeptide has hexosaminidase activity.

One aspect of the invention relates to a polypeptide comprising one or more of the motif(s) QSTL (SEQ ID NO 22), NKFFY (SEQ ID NO: 23) or NLD[DR]S (SEQ ID NO: 24), wherein the polypeptide comprises the amino acid sequence shown in SEQ ID NO 8 or is a polypeptide having at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99% or 100% sequence identity hereto, wherein the polypeptide has hexosaminidase activity.

One aspect of the invention relates to a polypeptide comprising one or more of the motif(s) QSTL (SEQ ID NO 22), NKFFY (SEQ ID NO: 23) or NLD[DR]S (SEQ ID NO: 24), wherein the polypeptide comprises the amino acid sequence shown in SEQ ID NO 9 or is a polypeptide having at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99% or 100% sequence identity hereto, wherein the polypeptide has hexosaminidase activity.

One aspect of the invention relates to a polypeptide comprising one or more of the motif(s) QSTL (SEQ ID NO 22), NKFFY (SEQ ID NO: 23) or NLD[DR]S (SEQ ID NO: 24), wherein the polypeptide comprises the amino acid sequence shown in SEQ ID NO 10 or is a polypeptide having at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99% or 100% sequence identity hereto, wherein the polypeptide has hexosaminidase activity.

One aspect of the invention relates to a polypeptide comprising one or more of the motif(s) QSTL (SEQ ID NO 22), NKFFY (SEQ ID NO: 23) or NLD[DR]S (SEQ ID NO: 24), wherein the polypeptide comprises the amino acid sequence shown in SEQ ID NO 11 or is a polypeptide having at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99% or 100% sequence identity hereto, wherein the polypeptide has hexosaminidase activity.

One aspect, relates to the use in a cleaning process of a polypeptide comprising the amino acid sequence shown in SEQ ID NO 7, SEQ ID NO 8, SEQ ID NO 9, SEQ ID NO 10, SEQ ID NO 11 or is a polypeptide having at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99% or 100% sequence identity hereto, wherein the polypeptide has hexosaminidase activity. Some aspects of the invention relate to cleaning e.g detergent compositions comprising a) one or more polypeptide selected from the group consisting of SEQ ID NO 7, SEQ ID NO 8, SEQ ID NO 9, SEQ ID NO 10 and SEQ ID NO 11, wherein the polypeptide has hexosaminidase activity and b) at least one surfactant, preferably at least one surfactant selected from the group consisting of anionic, nonionic and/or cationic surfactants.

On aspect of the invention relates to a composition comprising at least 0.001 ppm polypeptide having hexosaminidase activity, wherein the polypeptide is selected from the group consisting of polypeptides having at least 60% sequence identity to the mature polypeptide shown in SEQ ID NO 7, 8, 9, 10 and 11; and at least one adjunct ingredient.

The amount of polypeptide may be in the range of 0.00004-100 ppm, such as in the range of 0.00008-50 ppm, in the range of 0.00001-20, in the range of 0.0002-20 ppm, in the range of 0.0001-50 ppm, in the range of 0.0002-50, in the range of 0.0004-50, in the range of 0.0008-50, in the range of 0.001-50 ppm, 0.01-50 ppm, preferably 0.0001-50 ppm, more preferably 0.0002-20 ppm, more preferably 0.0002-10 ppm, more preferably 0.001-10 ppm, and most preferably 0.002-10 ppm. The hexosaminidase of the present invention may be in an amount corresponding to at least 0.00001 ppm, such as at least 0.00002 ppm, at least 0.0001 ppm, at least 0.0002 ppm, at least 0.0005 ppm, at least 0.001 ppm, at least 0.002 mg ppm, at least 0.005 ppm, at least 0.01 ppm or at least 0.02 ppm. The composition may comprise at least 0.00008%, preferably at least 0.0000.1%, 0.00002%, 0.000.1%, 0.0002%, 0.001%, 0.002%, 0.003%, 0.004%, 0.005%, 0.006%, 0.008%, 0.01%, 0.02%, 0.03%, 0.05%, 0.1%, 0.2%, 0.3%, 0.4%, 0.6%, 0.7%, 0.8%, 0.9% or 1.0% hexosaminidase.

Preferably, the polypeptide has N-acetylglucosaminidase activity and/or β-N-acetylglucosamininidase activity e.g. activity to PNAG. In one aspect, the polypeptide comprises one or more of the motif(s) GXDE (SEQ ID NO 18), [EQ][NRSHA][YVFL][AGSTC][IVLF][EAQYN][SN] (SEQ ID NO 19), [VIM][LIV]G[GAV]DE[VI][PSA] (SEQ ID NO: 20), WND[SQR][IVL][TLVM] (SEQ ID NO: 21), QSTL (SEQ ID NO 22), NKFFY (SEQ ID NO: 23), NLD[DR]S (SEQ ID NO: 24). In one aspect, the polypeptide has N-acetylglucosaminidase activity and/or β-N-acetylglucosamininidase activity e.g. activity to PNAG and comprises one or more of the motif(s) GXDE (SEQ ID NO 18), [EQ][NRSHA][YVFL][AGSTC][IVLF][EAQYN][SN] (SEQ ID NO 19), [VIM][LIV]G[GAV]DE[VI][PSA] (SEQ ID NO: 20), WND[SQR][IVL][TLVM] (SEQ ID NO: 21), QSTL (SEQ ID NO 22), NKFFY (SEQ ID NO: 23), NLD[DR]S (SEQ ID NO: 24). In one aspect, the polypeptide has at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO 7, SEQ ID NO 8, SEQ ID NO 9, SEQ ID NO 10 and SEQ ID NO 11.

In one aspect, the polypeptide has N-acetylglucosaminidase activity and/or β-N-acetylglucosamininidase activity e.g. activity to PNAG and comprises one or more of the motif(s) GXDE (SEQ ID NO 18), [EQ][NRSHA][YVFL][AGSTC][IVLF][EAQYN][SN] (SEQ ID NO 19), [VIM][LIV]G[GAV]DE[VI][PSA] (SEQ ID NO: 20), WND[SQR][IVL][TLVM] (SEQ ID NO: 21), QSTL (SEQ ID NO 22), NKFFY (SEQ ID NO: 23), NLD[DR]S (SEQ ID NO: 24), wherein the polypeptide has at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO 7, SEQ ID NO 8, SEQ ID NO 9, SEQ ID NO 10 and SEQ ID NO 11.

In one aspect, the polypeptide comprising or consisting of SEQ ID NO 7 or the mature polypeptide of SEQ ID NO 2, comprising or consisting of SEQ ID NO 8 or the mature polypeptide of SEQ ID NO 4, comprising or consisting of SEQ ID NO 9 or the mature polypeptide of SEQ ID NO 6, comprising or consisting of SEQ ID NO 10 or the mature polypeptide of SEQ ID NO 13 or comprising or consisting of SEQ ID NO 11 or the mature polypeptide of SEQ ID NO 15.

The composition is preferably a cleaning composition preferably a laundry or dish wash composition. Some aspect of the invention relates to a composition comprising a polypeptide of the invention and an adjunct ingredient, wherein the adjunct ingredient is selected from,
a) at least one builder,
b) at least one surfactant, and
at least one bleach component.

Some aspects of the invention relate to cleaning compositions e.g. detergent compositions comprising a) one or more polypeptide selected from the group consisting of SEQ ID NO 7, SEQ ID NO 8, SEQ ID NO 9, SEQ ID NO 10 and SEQ ID NO 11 or a polypeptide having at least 80% sequence identity hereto, wherein the polypeptide has hexosaminidase activity and b) at least one surfactant, preferably at least one surfactant selected from the group consisting of anionic, nonionic and/or cationic surfactants.

Some aspect of the invention relates to a detergent composition comprising:
a) at least 0.01 ppm of active enzyme polypeptide, wherein the enzyme polypeptide is selected from the group consisting of SEQ ID NO 7, SEQ ID NO 8 or SEQ ID NO 9 or polypeptides having at least 80% sequence identity hereto, wherein the polypeptide has hexosaminidase activity, and
b) from about 2 wt % to about 60 wt % surfactant or from about 5 wt % to about 60 wt % surfactant.

Some aspect of the invention relates to a detergent composition comprising:
a) at least 0.0001 ppm of active enzyme polypeptide, wherein the enzyme polypeptide is selected from the group consisting of SEQ ID NO 7, SEQ ID NO 8, SEQ ID NO 9, SEQ ID NO 10 and SEQ ID NO 11 or polypeptides having at least 80% sequence identity hereto, wherein the polypeptide has hexosaminidase activity, and
b) from about 2 wt % to about 60 wt % surfactant or from about 5 wt % to about 60 wt % surfactant from about 5 wt % to about 60 wt % surfactant.

The composition preferably comprises from about 2 wt % to about 60 wt %, from about 5 wt % to about 50 wt %, from about 5 wt % to about 40 wt %, from about 5 wt % to about 30 wt %, from about 5 wt % to about 20 wt %, from about 5 wt % to about 10 wt % anionic surfactants and/or nonionic surfactants. The surfactant may be selected among nonionic, anionic and/or amphoteric surfactants as described above, preferably anionic or nonionic surfactants but also amphoteric surfactants may be used. In general, bleach-stable surfactants are preferred. Preferred anionic surfactants are sulphate surfactants and in particular alkyl ether sulphates, especially C9-C15 alcohol ethersulfates, C12-C15 primary alcohol ethoxylate, C8-C16 ester sulphates and C10-C14 ester sulphates, such as mono dodecyl ester sulphates Non-limiting examples of anionic surfactants include sulfates and sulfonates, in particular, linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES, also known as alcohol ethoxysulfates or fatty alcohol ether sulfates), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or salt of fatty acids (soap), and combinations thereof. The anionic surfactants are preferably added to the detergent in the form of salts. Suitable cations in these salts are alkali metal ions, such as sodium, potassium and lithium and ammonium salts, for example (2-hydroxyethyl) ammonium, bis(2-hydroxyethyl) ammonium and tris(2-hydroxyethyl) ammonium salts. Non-limiting examples of nonionic surfactants include alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxyalkyl fatty acid amides, or N-acyl N-alkyl derivatives of glucosamine (glucamides, GA, or fatty acid glucamides, FAGA), as well as products available under the trade names SPAN and TWEEN, and combinations thereof. Commercially available nonionic surfactants includes Plurafac™ Lutensol™ and Pluronic™ range from BASF, Dehypon™ series from Cognis and Genapol™ series from Clariant.

In some aspect of the invention a detergent composition of the invention comprises:
a) at least 0.01 ppm of active enzyme polypeptide, wherein the enzyme polypeptide belongs to the *Terribacillus* clade and is selected from the group consisting of SEQ ID NO 7, SEQ ID NO 8, SEQ ID NO 9, SEQ ID NO 10 and SEQ ID NO 11 or polypeptides having at least 60% sequence identity hereto, wherein the polypeptide has hexosaminidase activity, b) from about 2 wt % to about 60 wt % of at least one surfactant In a preferred aspect of the invention the ratio of anionic/nonionic surfactant is above 1 i.e. the content of anionic surfactant is higher than the amount of nonionic surfactant. Thus, one aspect of the invention relates to a detergent composition comprising:

a) at least 0.01 ppm of active enzyme polypeptide, wherein the enzyme polypeptide belongs to the *Terribacillus* clade and is selected from the group consisting of SEQ ID NO 7, SEQ ID NO 8, SEQ ID NO 9, SEQ ID NO 10 and SEQ ID NO 11 or polypeptides having at least 60% sequence identity hereto, wherein the polypeptide has hexosaminidase activity, b) from about 5 wt % to about 50 wt % anionic surfactants, and c) from about 1 wt % to about 8 wt % nonionic surfactants.

The polypeptides of the invention may also be formulated in compositions e.g. liquid laundry composition optionally comprising a builder e.g. a liquid laundry compositions comprising:

a) at least 0.0001 ppm e.g. 0.01 ppm of active enzyme polypeptide, wherein the enzyme polypeptide belongs to the *Terribacillus* clade and is selected from the group consisting of SEQ ID NO 7, SEQ ID NO 8, SEQ ID NO 9, SEQ ID NO 10 and SEQ ID NO 11 or polypeptides having at least 60% sequence identity hereto, wherein the polypeptide has hexosaminidase activity, b) from about 2 wt % to about 60 wt % of at least one surfactant, and optionally c) from about 5 wt % to about 50 wt % of at least one builder such as carbonates, zeolites, phosphate builder, calcium sequestering builders or complexing agents.

The composition comprises at least one builder, wherein the builder is added in an amount from about 0 to about 65% wt %, from about 40 wt % to about 65 wt %, from about 20 wt % to about 65 wt %, from about 10 wt % to about 50 wt % or from about 5 wt % to about 50 wt % weight, wherein the builder is selected among phosphates, sodium citrate builders, sodium carbonate, sodium silicate, sodium and zeolites One aspect of the invention relates to a cleaning composition comprising:

a) at least 0.0001 ppm polypeptide, wherein the polypeptide belongs to the *Terribacillus* clade, comprises one or both motif(s) [VIM][LIV]G[GAV]DE[VI][PSA] (SEQ ID NO 20) or WND[SQR][IVL][TLVM] (SEQ ID NO 21), wherein the polypeptide is selected from the group consisting of SEQ ID NO 7, SEQ ID NO 8, SEQ ID NO 9, SEQ ID NO 10, SEQ ID NO 11 and polypeptides having at least 80% sequence identity hereto and wherein the polypeptide has hexosaminidase activity, and optionally b) from about 2 wt % to about 60 wt % of at least one surfactant, and optionally c) from about 5 wt % to about 50 wt % of at least one builder, and optionally d) from about 1 wt % to about 15 wt % of at least on bleach component.

The surfactant may be any of those described above.

The builder is preferably selected among phosphates, sodium citrate builders, sodium carbonate, sodium silicate, sodium aluminosilicate (zeolite). Suitable builders are alkali metal or ammonium phosphates, polyphosphates, phosphonates, polyphosphonates, carbonates, bicarbonates, borates, citrates, and polycarboxylates. Citrate builders, e.g., citric acid and soluble salts thereof (particularly sodium salt), are polycarboxylate builders. Citrates can be used in combination with zeolite, silicates like the BRITESIL types, and/or layered silicate builders. The builder is preferably added in an amount of about 0-65% by weight, such as about 5% to about 50% by weight. In the composition, the level of builder is typically about 40-65% by weight, particularly about 50-65% by weight, particularly from 20% to 50% by weight. The builder and/or co-builder may particularly be a chelating agent that forms water-soluble complexes with Ca and Mg. Any builder and/or co-builder known in the art for use in cleaning detergents may be utilized. Non-limiting examples of builders include zeolites, diphosphates (pyrophosphates), triphosphates such as sodium triphosphate (STP or STPP), carbonates such as sodium carbonate, soluble silicates such as sodium metasilicate, layered silicates (e.g., SKS-6 from Hoechst), and (carboxymethyl) inulin (CMI), and combinations thereof. Further non-limiting examples of builders include citrate, chelators such as am inocarboxylates, aminopolycarboxylates and phosphonates, and alkyl- or alkenylsuccinic acid. Additional specific examples include 2,2',2"-nitrilotriacetic acid (NTA), ethylenediaminetetraacetic acid (EDTA), diethylenetriaminepentaacetic acid (DTPA), iminodisuccinic acid (IDS), ethylenediamine-N,N'-disuccinic acid (EDDS), methylglycine-N,N-diacetic acid (MGDA), glutamic acid-N,N-diacetic acid (GLDA), 1-hydroxyethane-1,1-diphosphonic acid, N-(2-hydroxyethyl)iminodiacetic acid (EDG), aspartic acid-N-monoacetic acid (ASMA), aspartic acid-N,N-diacetic acid (ASDA), aspartic acid-N-monopropionic acid (ASMP), iminodisuccinic acid (IDA), N-(sulfomethyl)aspartic acid (SMAS), N-(2-sulfoethyl)-aspartic acid (SEAS), N-(sulfomethylglutamic acid (SMGL), N-(2-sulfoethyl)-glutamic acid (SEGL), N-methyliminodiacetic acid (MIDA), serine-N,N-diacetic acid (SEDA), isoserine-N,N-diacetic acid (ISDA), phenylalanine-N,N-diacetic acid (PHDA), anthranilic acid-N,N-diacetic acid (ANDA), sulfanilic acid-N,N-diacetic acid (SLDA), taurine-N,N-diacetic acid (TUDA) and N'-(2-hydroxyethyl)ethylenediamine-N,N,N'-triacetic acid (HEDTA), diethanolglycine (DEG), and combinations and salts thereof.

Phosphonates suitable for use herein include 1-hydroxyethane-1,1-diphosphonic acid (HEDP), ethylenediaminetetrakis (methylenephosphonic acid) (EDTMPA), diethylentriaminepentakis (methylenephosphonic acid) (DTMPA or DTPMPA or DTPMP), nitrilotris (methylenephosphonic acid) (ATMP or NTMP), 2-phosphonobutane-1,2,4-tricarboxylic acid (PBTC), hexamethylenediaminetetrakis (methylenephosphonic acid) (HDTMP)

The composition may also contain 0-50% by weight, such as about 5% to about 30%, of a detergent co-builder.

The composition may include a co-builder alone, or in combination with a builder, for example a zeolite builder. Non-limiting examples of co-builders include homopolymers of polyacrylates or copolymers thereof, such as poly (acrylic acid) (PAA) or copoly (acrylic acid/maleic acid) (PAA/PMA) or polyaspartic acid.

Further exemplary builders and/or co-builders are described in, e.g., WO 09/102854, U.S. Pat. No. 5,977,053

In one preferred embodiment, the builder is a non-phosphorus based builder such as citric acid and/or methylglycine-N, N-diacetic acid (MGDA) and/or glutamic-N, N-diacetic acid (GLDA) and/or salts thereof.

Some aspect of the invention relates a composition comprising at least one enzyme polypeptide, wherein the enzyme is selected from the group consisting of polypeptides having SEQ ID NO 7, SEQ ID NO 8, SEQ ID NO 9, SEQ ID NO 10 and SEQ ID NO 11 or polypeptides having at least 60% sequence identity hereto, wherein the polypeptide has hexosaminidase activity and a non-phosphate builder selected from citric acid, methyl glycine-N,N-diacetic acid (MGDA) and/or glutamic-N,N-diacetic acid (GLDA) and mixtures thereof.

In one aspect, the composition is detergent composition, such as a laundry composition, an automatic dish wash composition (ADW) comprising:
 a) at least 0.0001 ppm e.g. 0.01 ppm of active enzyme polypeptide, wherein the enzyme polypeptide is selected from the group consisting of SEQ ID NO 7, SEQ ID NO 8, SEQ ID NO 9, SEQ ID NO 10 and SEQ ID NO 11 or polypeptides having at least 60% sequence identity hereto, wherein the polypeptide has hexosaminidase activity, and
 b) 10-50 wt % builder selected from citric acid, methylglycine-N, N-diacetic acid (MGDA) and/or glutamic acid-N, N-diacetic acid (GLDA) and mixtures thereof, and optionally
 c) at least one bleach component.

The composition may contain 0-30% by weight, such as about 1% to about 20%, such as about 1% to about 10%, such as about 1% to about 5%, such as about 10% to about 30%, such as about 5% to about 10% or such as about 10% to about 20% by weight (wt %) of a bleaching system. Any bleaching system comprising components known in the art for use in cleaning detergents may be utilized. Suitable bleaching system components include sources of hydrogen peroxide; sources of peracids; and bleach catalysts or boosters.

Sources of Hydrogen Peroxide

Suitable sources of hydrogen peroxide are inorganic persalts, including alkali metal salts such as sodium percarbonate and sodium perborates (usually mono- or tetrahydrate), and hydrogen peroxide-urea (1/1).

Sources of Peracids

Peracids may be (a) incorporated directly as preformed peracids or (b) formed in situ in the wash liquor from hydrogen peroxide and a bleach activator (perhydrolysis) or (c) formed in situ in the wash liquor from hydrogen peroxide and a perhydrolase and a suitable substrate for the latter, e.g., an ester.

a) Suitable preformed peracids include, but are not limited to, peroxycarboxylic acids such as peroxybenzoic acid and its ring-substituted derivatives, peroxy-α-naphthoic acid, peroxyphthalic acid, peroxylauric acid, peroxystearic acid, ε-phthalimidoperoxycaproic acid [phthalimidoperoxyhexanoic acid (PAP)], and o-carboxybenzamidoperoxycaproic acid; aliphatic and aromatic diperoxydicarboxylic acids such as diperoxydodecanedioic acid, diperoxyazelaic acid, diperoxysebacic acid, diperoxybrassylic acid, 2-decyldiperoxybutanedioic acid, and diperoxyphthalic, -isophthalic and -terephthalic acids; perimidic acids; peroxymonosulfuric acid; peroxydisulfuric acid; peroxyphosphoric acid; peroxysilicic acid; and mixtures of said compounds. It is understood that the peracids mentioned may in some cases be best added as suitable salts, such as alkali metal salts (e.g., Oxone®) or alkaline earth-metal salts.

b) Suitable bleach activators include those belonging to the class of esters, amides, imides, nitriles or anhydrides and, where applicable, salts thereof. Suitable examples are tetraacetylethylenediamine (TAED), sodium 4-[(3,5,5-trimethylhexanoyl)oxy]benzene-1-sulfonate (ISONOBS), sodium 4-(dodecanoyloxy)benzene-1-sulfonate (LOBS), sodium 4-(decanoyloxy)benzene-1-sulfonate, 4-(decanoyloxy)benzoic acid (DOBA), sodium 4-(nonanoyloxy)benzene-1-sulfonate (NOBS), and/or those disclosed in WO98/17767. A family of bleach activators of interest was disclosed in EP624154 and particularly preferred in that family is acetyl triethyl citrate (ATC). ATC or a short chain triglyceride like triacetin has the advantage that they are environmentally friendly. Furthermore, acetyl triethyl citrate and triacetin have good hydrolytical stability in the product upon storage and are efficient bleach activators. Finally, ATC is multifunctional, as the citrate released in the perhydrolysis reaction may function as a builder.

Bleach Catalysts and Boosters

The bleaching system may also include a bleach catalyst or booster.

Some non-limiting examples of bleach catalysts that may be used in the compositions of the present invention include manganese oxalate, manganese acetate, manganese-collagen, cobalt-amine catalysts and manganese triazacyclononane (MnTACN) catalysts; particularly preferred are complexes of manganese with 1,4,7-trimethyl-1,4,7-triazacyclononane (Me3-TACN) or 1,2,4,7-tetramethyl-1,4,7-triazacyclononane (Me4-TACN), in particular Me3-TACN, such as the dinuclear manganese complex [(Me3-TACN)Mn(O)3Mn(Me3-TACN)](PF6)2, and [2,2',2"-nitrilotris(ethane-1,2-diylazanylylidene-κN-methanylylidene)triphenolato-κ3O]manganese(III). The bleach catalysts may also be other metal compounds, such as iron or cobalt complexes.

In some embodiments, where a source of a peracid is included, an organic bleach catalyst or bleach booster may be used having one of the following formulae:

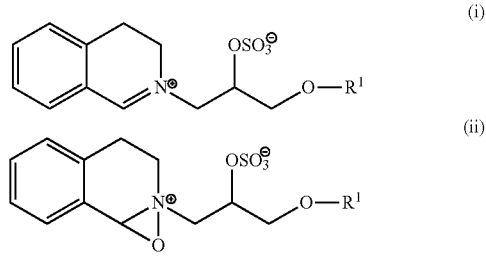

(iii) and mixtures thereof; wherein each R1 is independently a branched alkyl group containing from 9 to 24 carbons or linear alkyl group containing from 11 to 24 carbons, preferably each R1 is independently a branched alkyl group containing from 9 to 18 carbons or linear alkyl group containing from 11 to 18 carbons, more preferably each R1 is independently selected from the group consisting of 2-propylheptyl, 2-butyloctyl, 2-pentylnonyl, 2-hexyldecyl, dodecyl, tetradecyl, hexadecyl, octadecyl, isononyl, isodecyl, isotridecyl and isopentadecyl. Other exemplary bleaching systems are described, e.g. in WO2007/087258, WO2007/087244, WO2007/087259, EP1867708 (Vitamin K) and WO2007/087242. Suitable photobleaches may for example be sulfonated zinc or aluminium phthalocyanines.

The present invention relates to polypeptides of the *Terribacillus* clade having hexosaminidase activity, compositions e.g. detergent compositions comprising the polypeptides, and the use of detergent composition comprising the polypeptides of the invention for deep cleaning of an item such as a textile.

Accordingly, some aspects of the invention relate to cleaning composition e.g. detergent compositions comprising:

a) at least 0.0001 ppm e.g. 0.001 ppm polypeptide of the *Terribacillus* clade, optionally comprising one or more motif selected from the group consisting of GXDE (SEQ ID NO 18), [EQ][NRSHA][YVFL][AGSTC][IVLF][EAQYN][SN] (SEQ ID NO 19), [VIM][LIV]G[GAV]DE[VI][PSA] (SEQ ID NO: 20), WND[SQR][IVL][TLVM] (SEQ ID NO: 21), QSTL (SEQ ID NO 22), NKFFY (SEQ ID NO: 23), NLD[DR]S (SEQ ID NO: 24), wherein the enzyme polypeptide is selected from the group consisting of SEQ ID NO 7, SEQ ID NO 8, SEQ ID NO 9, SEQ ID NO 10, SEQ ID NO 11 and polypeptides having at least 60%, such as at least 70%, such as at least 80% or such as at least 90% sequence identity hereto, wherein the polypeptide has hexosaminidase activity, and optionally
b) from about 10 wt % to about 50 wt % builder preferably selected from citric acid, methylglycine-N, N-diacetic acid (MGDA) and/or glutamic acid-N, N-diacetic acid (GLDA) and mixtures thereof, and optionally
c) from about 5 wt % to about 50 wt % surfactant, preferably selected from anionic surfactants such as LAS, AOS, AEOS and/or nonionic surfactants such as AE or AEO, and optionally
d) at least one bleach component, preferably selected from percarbonates, persulphates and peracids.

Accordingly, some aspects of the invention relate to detergent compositions comprising:

a) at least 0.0001 ppm e.g. 0.001 ppm polypeptide of the *Terribacillus* clade, optionally comprising one or more motif selected from the group consisting of GXDE (SEQ ID NO 18), [EQ][NRSHA][YVFL][AGSTC][IVLF][EAQYN][SN] (SEQ ID NO 19), [VIM][LIV]G[GAV]DE[VI][PSA] (SEQ ID NO: 20), WND[SQR][IVL][TLVM] (SEQ ID NO: 21), QSTL (SEQ ID NO 22), NKFFY (SEQ ID NO: 23), NLD[DR]S (SEQ ID NO: 24), wherein the enzyme polypeptide is selected from the group consisting of SEQ ID NO 7, SEQ ID NO 8, SEQ ID NO 9, SEQ ID NO 10, SEQ ID NO 11 and polypeptides having at least 60%, such as at least 70%, such as at least 80% or such as at least 90% sequence identity hereto, wherein the polypeptide has hexosaminidase activity, and optionally
b) from about 10 wt % to about 50 wt % builder preferably selected from citric acid, methylglycine-N, N-diacetic acid (MGDA) and/or glutamic acid-N, N-diacetic acid (GLDA) and mixtures thereof, and optionally
c) from about 5 wt % to about 50 wt % surfactant, preferably selected from anionic surfactants such as LAS, AOS, AEOS and/or nonionic surfactants such as AE or AEO, and optionally
d) at least one bleach component, preferably selected from percarbonates, persulphates and peracids.

Accordingly, some aspects of the invention relate to detergent compositions comprising:

a) at least 0.0001 ppm e.g. 0.001 ppm of polypeptide of the *Terribacillus* clade, optionally comprising one or more motif selected from the group consisting of GXDE (SEQ ID NO 18), [EQ][NRSHA][YVFL][AGSTC][IVLF][EAQYN][SN] (SEQ ID NO 19), [VIM][LIV]G[GAV]DE[VI][PSA] (SEQ ID NO: 20), WND[SQR][IVL][TLVM] (SEQ ID NO: 21), QSTL (SEQ ID NO 22), NKFFY (SEQ ID NO: 23), NLD[DR]S (SEQ ID NO: 24), wherein the enzyme polypeptide is selected from the group consisting of SEQ ID NO 7, SEQ ID NO 8, SEQ ID NO 9, SEQ ID NO 10, SEQ ID NO 11 and polypeptides having at least 60%, such as at least 70%, such as at least 80% or such as at least 90% sequence identity hereto, wherein the polypeptide has hexosaminidase activity, and optionally
b) from about 10 wt % to about 50 wt % builder preferably selected from citric acid, methylglycine-N, N-diacetic acid (MGDA) and/or glutamic acid-N, N-diacetic acid (GLDA) and mixtures thereof, and optionally
c) from about 5 wt % to about 50 wt % surfactant, preferably selected from anionic surfactants such as LAS, AOS, AEOS and/or nonionic surfactants such as AE or AEO, and optionally
d) at least one bleach component, wherein the bleach is a peroxide and the bleach catalyst is a manganese compound, wherein, the oxygen bleach is preferably percarbonate and the manganese catalyst preferably 1,4,7-trimethyl-1,4,7-triazacyclononane or manganese (III) acetate tetrahydrate (MnTACN).

One aspect relates to the use of a composition of as described above for deep-cleaning of an item, such as a textile.

The polypeptides of the invention having hexosaminidase activity may be used for deep cleaning of items such as hard surfaces, textiles and/or fabric. In some aspects of the invention the polypeptides of the invention e.g. the polypeptides having at least at least 60%, such as at least 70%, such as at least 80% or such as at least 90% sequence identity the mature polypeptides of SEQ ID NO 2, SEQ ID NO 4, SEQ ID NO 6, SEQ ID NO 13 and SEQ ID NO 15 or to the mature polypeptide with SEQ ID NO 7, SEQ ID NO 8, SEQ ID NO 9, SEQ ID NO 10 and SEQ ID NO 11, have β-N-acetylglucosamininidase activity and in some aspects the hexosaminidase activity is β-N-acetylglucosamininidase activity and the polypeptide of the invention are β-N-acetylglucosamininidases.

One aspect of the invention relates to the use of a polypeptide of the *Terribacillus* clade, wherein the polypeptide has hexosaminidase activity, preferably N-acetylglucosaminidase activity and/or β-N-acetylglucosamininidase activity in a cleaning process, such as laundry and/or dish wash.

One aspect of the invention relates to the use of a polypeptide comprising one or more of the motif(s) GXDE (SEQ ID NO 18), [EQ][NRSHA][YVFL][AGSTC][IVLF][EAQYN][SN] (SEQ ID NO 19), [VIM][LIV]G[GAV]DE[VI][PSA] (SEQ ID NO: 20), WND[SQR][IVL][TLVM] (SEQ ID NO: 21), QSTL (SEQ ID NO 22), NKFFY (SEQ ID NO: 23), NLD[DR]S (SEQ ID NO: 24).

One aspect of the invention relates to the use of a polypeptide of the *Terribacillus* clade, wherein the polypeptide has hexosaminidase activity, preferably N-acetylglucosaminidase activity and/or β-N-acetylglucosamininidase activity in a cleaning process, such as laundry and/or dish wash wherein the polypeptide comprises one or more of the motif(s) GXDE (SEQ ID NO 18), [EQ][NRSHA][YVFL][AGSTC][IVLF][EAQYN][SN] (SEQ ID NO 19), [VIM][LIV]G[GAV]DE[VI][PSA] (SEQ ID NO: 20), WND[SQR][IVL][TLVM] (SEQ ID NO: 21), QSTL (SEQ ID NO 22), NKFFY (SEQ ID NO: 23), NLD[DR]S (SEQ ID NO: 24).

One aspect of the present invention relates to the use of a polypeptide of the *Terribacillus* clade e.g. comprising one or both of the motifs GXDE (SEQ ID NO 18), [EQ][NRSHA][YVFL][AGSTC][IVLF][EAQYN][SN] (SEQ ID NO 19), [VIM][LIV]G[GAV]DE[VI][PSA] (SEQ ID NO: 20), WND[SQR][IVL][TLVM] (SEQ ID NO: 21), QSTL (SEQ ID NO 22), NKFFY (SEQ ID NO: 23), NLD[DR]S (SEQ ID NO:

24), wherein the polypeptide has hexosaminidase activity and wherein the polypeptide is a polypeptide having at least 60% e.g. 80%, 85%, 90% or 95% sequence identity to the mature polypeptides shown in SEQ ID NO 7, SEQ ID NO 8, SEQ ID NO 9, SEQ ID NO 10 or SEQ ID NO 11 for deep cleaning of an item, wherein the item is a textile. In one aspect of the invention the polypeptide of the *Terribacillus* clade having hexosaminidase activity is used for preventing, reducing or removing the stickiness of an item. In one aspect of the invention the polypeptide of the *Terribacillus* clade having hexosaminidase activity can further be used for pre-treating stains on textile such as textile.

One aspect of the invention relates to the use of a polypeptide of the *Terribacillus* clade having hexosaminidase activity for preventing, reducing or removing re-deposition of soil during a wash cycle.

Further, one aspect of the invention relates to the use of a polypeptide of the *Terribacillus* clade having hexosaminidase activity for preventing, reducing or removing the adherence of soil to an item. In one embodiment, the item is textile. When the soil does not adhere to the item, the item appears cleaner. Thus, the invention further concerns the use of a polypeptide of the *Terribacillus* clade having hexosaminidase activity for maintaining or improving the whiteness of the item.

When items like T-shirts or sportswear are used, they are exposed to bacteria from the body of the user and from the rest of the environment in which they are used. This may cause malodor on the item even after the item is washed. The present invention therefore also concerns removal or reduction of malodor on textile. The malodor may be caused by bacteria producing compounds with an unpleasant smell. One example of such unpleasant smelling compounds is E-2-nonenal. The malodor can be present on newly washed textile which is still wet. Or the malodor can be present on newly washed textile, which has subsequently been dried. The malodor may also be present on textile, which has been stored for some time after wash. The present invention relates to reduction or removal of malodor such as E-2-nonenal from wet or dry textile.

One aspect of the invention relates to the use of a polypeptide of the *Terribacillus* clade e.g. comprising one or more motif(s) GXDE (SEQ ID NO 18), [EQ][NRSHA][YVFL][AGSTC][IVLF][EAQYN][SN] (SEQ ID NO 19), [VIM][LIV]G[GAV]DE[VI][PSA] (SEQ ID NO: 20), WND[SQR][IVL][TLVM] (SEQ ID NO: 21), QSTL (SEQ ID NO 22), NKFFY (SEQ ID NO: 23), NLD[DR]S (SEQ ID NO: 24), wherein the polypeptide has hexosaminidase activity, preferably N-acetylglucosaminidase activity and/or β-N-acetylglucosamininidase activity and wherein the polypeptide is a polypeptide having at 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptides shown in SEQ ID NO 7, SEQ ID NO 8, SEQ ID NO 9, SEQ ID NO 10 or SEQ ID NO 11, (i) for preventing, reducing or removing stickiness of the item;
(ii) for pretreating stains on the item;
(iii) for preventing, reducing or removing redeposition of soil during a wash cycle;
(iv) for preventing, reducing or removing adherence of soil to the item;
(v) for maintaining or improving of whiteness of the item;
(vi) for preventing, reducing or removal malodor from the item,
 wherein the item is a textile.

A cleaning e.g. detergent composition according to the invention may comprise at least one adjunct ingredient e.g. a detergent adjunct, the detergent adjunct ingredient may be surfactants and builders and/or chelators such as those described above. The adjunct ingredients may also be any of the following flocculating aid, dye transfer inhibitors, enzymes, enzyme stabilizers, enzyme inhibitors, catalytic materials, bleach activators, hydrogen peroxide, sources of hydrogen peroxide, preformed peracids, polymeric dispersing agents, clay soil removal/anti-redeposition agents, brighteners, suds suppressors, dyes, perfumes, structure elasticizing agents, fabric softeners, carriers, hydrotropes, builders and co-builders, fabric hueing agents, anti-foaming agents, dispersants, processing aids, and/or pigments.

In one embodiment, the detergent adjunct ingredient is a builder or a clay soil removal/anti-redeposition agent.

In one embodiment, detergent adjunct ingredient is an enzyme. The one or more enzymes may be selected from the group consisting of proteases, lipases, cutinases, amylases, carbohydrases, cellulases, pectinases, mannanases, arabinases, galactanases, xylanases and oxidases.

In addition to the polypeptides having hexosaminidase activity comprising the polypeptides of SEQ ID NO 7, SEQ ID NO 8, SEQ ID NO 9, SEQ ID NO 10, SEQ ID NO 11 or a polypeptide having hexosaminidase activity and having at least 60% sequence identity hereto the cleaning composition of the invention may further comprise cellulases. Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. Nos. 4,435,307, 5,648,263, 5,691,178, 5,776,757 and WO 89/09259. Especially suitable cellulases are the alkaline or neutral cellulases having color care benefits. Examples of such cellulases are cellulases described in EP 0 495 257, EP 0 531 372, WO 96/11262, WO 96/29397, WO 98/08940. Other examples are cellulase polypeptides such as those described in WO 94/07998, EP 0 531 315, U.S. Pat. Nos. 5,457,046, 5,686,593, 5,763,254, WO 95/24471, WO 98/12307 and PCT/DK98/00299. Example of cellulases exhibiting endo-beta-1,4-glucanase activity (EC 3.2.1.4) are those having described in WO02/099091. Other examples of cellulases include the family 45 cellulases described in WO96/29397, and especially polypeptides thereof having substitution, insertion and/or deletion at one or more of the positions corresponding to the following positions in SEQ ID NO 8 of WO 02/099091: 2, 4, 7, 8, 10, 13, 15, 19, 20, 21, 25, 26, 29, 32, 33, 34, 35, 37, 40, 42, 42a, 43, 44, 48, 53, 54, 55, 58, 59, 63, 64, 65, 66, 67, 70, 72, 76, 79, 80, 82, 84, 86, 88, 90, 91, 93, 95, 95d, 95h, 95j, 97, 100, 101, 102, 103, 113, 114, 117, 119, 121, 133, 136, 137, 138, 139, 140a, 141, 143a, 145, 146, 147, 150e, 150j, 151, 152, 153, 154, 155, 156, 157, 158, 159, 160c, 160e, 160k, 161, 162, 164, 165, 168, 170, 171, 172, 173, 175, 176, 178, 181, 183, 184, 185, 186, 188, 191, 192, 195, 196, 200, and/or 20, preferably selected among P19A, G20K, Q44K, N48E, Q119H or Q146R. Commercially available cellulases include Celluzyme™, Celluclean™ and Carezyme™ (Novozymes A/S), Clazinase™, and Puradax HA™ (Genencor International Inc.), and KAC-500 (B)™ (Kao Corporation).

In addition to the polypeptides having hexosaminidase activity comprising SEQ ID NO 7, SEQ ID NO 8, SEQ ID NO 9 SEQ ID NO 10, SEQ ID NO 11 or a polypeptide having hexosaminidase activity and having at least 60% sequence identity hereto the cleaning composition of the invention may further comprise proteases. Suitable proteases include those of bacterial, fungal, plant, viral or animal origin e.g. vegetable or microbial origin. Microbial origin is preferred. Chemically modified or protein engineered mutants are included. It may be an alkaline protease, such as a serine protease or a metalloprotease. A serine protease may for example be of the S1 family, such as trypsin, or the S8 family such as Subtilisin. A metalloproteases protease may for example be a thermolysin from e.g. family M4 or other metalloprotease such as those from M5, M7 or M8 families. The term "subtilases" refers to a sub-group of serine protease according to Siezen et al., Protein Engng. 4 (1991) 719-737 and Siezen et al. Protein Science 6 (1997) 501-523. Serine proteases are a subgroup of proteases characterized by having a serine in the active site, which forms a covalent adduct with the substrate. The subtilases may be divided into 6 sub-divisions, i.e. the Subtilisin family, the Thermitase family, the Proteinase K family, the Lantibiotic peptidase family, the Kexin family and the Pyrolysin family. Examples of subtilases are those derived from *Bacillus* such as *Bacillus lentus, B. alkalophilus, B. subtilis, B. amyloliquefaciens, Bacillus pumilus* and *Bacillus gibsonii* described in; U.S. Pat. No. 7,262,042 and WO09/021867, and *Subtilisin lentus, Subtilisin novo, Subtilisin carlsberg, Bacillus licheniformis, Subtilisin* BPN', *Subtilisin* 309, *Subtilisin* 147 and *Subtilisin* 168 described in WO89/06279 and protease PD138 described in (WO93/18140). Other useful proteases may be those described in WO92/175177, WO01/016285, WO02/026024 and WO02/016547. Examples of trypsin-like proteases are trypsin (e.g. of porcine or bovine origin) and the *Fusarium* protease described in WO89/06270, WO94/25583 and WO05/040372, and the chymotrypsin proteases derived from *Cellumonas* described in WO05/052161 and WO05/052146. A further preferred protease is the alkaline protease from *Bacillus lentus* DSM 5483, as described for example in WO95/23221, and variants thereof which are described in WO92/21760, WO95/23221, EP1921147 and EP1921148. Examples of metalloproteases are the neutral metalloprotease as described in WO07/044993 (Genencor Int.) such as those derived from *Bacillus amyloliquefaciens*.

Examples of useful proteases are the variants described in: WO92/19729, WO96/034946, WO98/20115, WO98/20116, WO99/011768, WO01/44452, WO03/006602, WO04/03186, WO04/041979, WO07/006305, WO11/036263, WO11/036264, especially the variants with substitutions in one or more of the following positions: 3, 4, 9, 15, 24, 27, 42, 55, 59, 60, 66, 74, 85, 96, 97, 98, 99, 100, 101, 102, 104, 116, 118, 121, 126, 127, 128, 154, 156, 157, 158, 161, 164, 176, 179, 182, 185, 188, 189, 193, 198, 199, 200, 203, 206, 211, 212, 216, 218, 226, 229, 230, 239, 246, 255, 256, 268 and 269 compared to SEQ ID NO 1 of WO2016/001449, wherein the positions correspond to the positions of the *Bacillus lentus* protease shown in SEQ ID NO 1 of WO2016/001449. More preferred subtilase variants may comprise any of the mutations: S3T, V4I, S9R, S9E, A15T, S24G, S24R, K27R, N42R, S55P, G59E, G59D, N60D, N60E, V66A, N74D, N85S, N85R, G96S, G96A, S97G, S97D, S97A, S97SD, S99E, S99D, S99G, S99M, S99N, S99R, S99H, S101A, V102I, V102Y, V102N, S104A, G116V, G116R, H118D, H118N, N120S, S126L, P127Q, S128A, S154D, A156E, G157D, G157P, S158E, Y161A, R164S, Q176E, N179E, S182E, Q185N, A188P, G189E, V193M, N198D, V199I, Y203W, S206G, L211Q, L211D, N212D, N212S, M216S, A226V, K229L, Q230H, Q239R, N246K, N255W, N255D, N255E, L256E, L256D T268A or R269H. The protease variants are preferably variants of the *Bacillus lentus* protease (Savinase®) shown in SEQ ID NO 1 of WO2016/001449 or the *Bacillus amylolichenifaciens* protease (BPN') shown in SEQ ID NO 2 of WO2016/001449. The protease variants preferably have at least 80% sequence identity to SEQ ID NO 1 or SEQ ID NO 2 of WO2016/001449.

A protease variant comprising a substitution at one or more positions corresponding to positions 171, 173, 175, 179, or 180 of SEQ ID NO 1 of WO2004/067737, wherein said protease variant has a sequence identity of at least 75% but less than 100% to SEQ ID NO 1 of WO2004/067737.

Suitable commercially available protease enzymes include those sold under the trade names Alcalase®, Duralase™, Durazym™, Relase®, Relase® Ultra, Savinase®, Savinase® Ultra, Primase®, Polarzyme®, Kannase®, Liquanase®, Liquanase® Ultra, Ovozyme®, Coronase®, Coronase® Ultra, Blaze®, Blaze Evity® 100T, Blaze Evity® 125T, Blaze Evity® 150T, Neutrase®, Everlase® and Esperase® (Novozymes A/S), those sold under the tradename Maxatase®, Maxacal®, Maxapem®, Purafect Ox®, Purafect OxP®, Puramax®, FN2®, FN3®, FN4®, Excellase®, Excellenz P1000™, Excellenz P1250™, Eraser®, Preferenz P100™, Purafect Prime®, Preferenz P110™, Effectenz P1000™, Purafect®™, Effectenz P1050™, Purafect Ox®™, Effectenz P2000™, Purafast®, Properase®, Opticlean® and Optimase® (Danisco/DuPont), Axapem™ (Gist-Brocases N.V.), BLAP (sequence shown in FIG. 29 of U.S. Pat. No. 5,352,604) and variants hereof (Henkel AG) and KAP (*Bacillus alkalophilus* Subtilisin) from Kao.

In addition to the polypeptides having hexosaminidase activity comprising the polypeptides of SEQ ID NO 7, SEQ ID NO 8, SEQ ID NO 9, SEQ ID NO 10, SEQ ID NO 11 or a polypeptide having hexosaminidase activity and having at least 60% sequence identity hereto the cleaning composition of the invention may further comprise lipases and cutinases which include those of bacterial or fungal origin. Chemically modified or protein engineered mutant enzymes are included. Examples include lipase from *Thermomyces*, e.g. from *T. lanuginosus* (previously named *Humicola lanuginosa*) as described in EP258068 and EP305216, cutinase from *Humicola*, e.g. *H. insolens* (WO96/13580), lipase from strains of *Pseudomonas* (some of these now renamed to *Burkholderia*), e.g. *P. alcaligenes* or *P. pseudoalcaligenes* (EP218272), *P. cepacia* (EP331376), *P.* sp. strain SD705 (WO95/06720 & WO96/27002), *P. wisconsinensis* (WO96/12012), GDSL-type *Streptomyces* lipases (WO10/065455), cutinase from *Magnaporthe grisea* (WO10/107560), cutinase from *Pseudomonas mendocina* (U.S. Pat. No. 5,389, 536), lipase from *Thermobifida fusca* (WO11/084412), *Geobacillus stearothermophilus* lipase (WO11/084417), lipase from *Bacillus subtilis* (WO11/084599), and lipase from *Streptomyces griseus* (WO11/150157) and *S. pristinaespiralis* (WO12/137147). Other examples are lipase polypeptides such as those described in EP407225, WO92/05249, WO94/01541, WO94/25578, WO95/14783, WO95/30744, WO95/35381, WO95/22615, WO96/00292, WO97/04079, WO97/07202, WO00/34450, WO00/60063, WO01/92502, WO07/87508 and WO09/109500. Preferred commercial lipase products include Lipolase™, Lipex™; Lipolex™ and Lipoclean™ (Novozymes A/S), Lumafast (originally from Genencor) and Lipomax (originally from Gist-Brocades).

Yet other examples are lipases sometimes referred to as acyltransferases or perhydrolases, e.g. acyltransferases with homology to *Candida antarctica* lipase A (WO10/111143), acyltransferase from *Mycobacterium smegmatis* (WO05/56782), perhydrolases from the CE 7 family (WO09/67279), and polypeptides of the *M. smegmatis* perhydrolase in particular the S54V variant used in the commercial product Gentle Power Bleach from Huntsman Textile Effects Pte Ltd (WO10/100028).

In addition to the polypeptides having hexosaminidase activity comprising SEQ ID NO 7, SEQ ID NO 8, SEQ ID NO 9, SEQ ID NO 10, SEQ ID NO 11 or a polypeptide having hexosaminidase activity and having at least 60% sequence identity hereto the cleaning composition of the invention may further comprise amylases which can be used together with a polypeptide of the invention. The amylase may be an alpha-amylase or a glucoamylase and may be of bacterial or fungal origin. Chemically modified or protein engineered mutants are included. Amylases include, for example, alpha-amylases obtained from *Bacillus*, e.g., a special strain of *Bacillus licheniformis*, described in more detail in GB 1,296,839. Suitable amylases include amylases having SEQ ID NO 3 in WO 95/10603 or polypeptides having 90% sequence identity to SEQ ID NO 3 thereof. Preferred polypeptides are described in WO 94/02597, WO 94/18314, WO 97/43424 and SEQ ID NO 4 of WO 99/019467, such as polypeptides with substitutions in one or more of the following positions: 15, 23, 105, 106, 124, 128, 133, 154, 156, 178, 179, 181, 188, 190, 197, 201, 202, 207, 208, 209, 211, 243, 264, 304, 305, 391, 408, and 444. Different suitable amylases include amylases having SEQ ID NO 6 in WO 02/010355 or polypeptides thereof having 90% sequence identity to SEQ ID NO 6. Preferred polypeptides of SEQ ID NO 6 are those having a deletion in positions 181 and 182 and a substitution in position 193. Other amylases which are suitable are hybrid alpha-amylase comprising residues 1-33 of the alpha-amylase derived from *B. amyloliquefaciens* shown in SEQ ID NO 6 of WO 2006/066594 and residues 36-483 of the *B. licheniformis* alpha-amylase shown in SEQ ID NO 4 of WO 2006/066594 or polypeptides having 90% sequence identity thereof. Preferred polypeptides of this hybrid alpha-amylase are those having a substitution, a deletion or an insertion in one of more of the following positions: G48, T49, G107, H156, A181, N190, M197, I201, A209 and Q264. Most preferred polypeptides of the hybrid alpha-amylase comprising residues 1-33 of the alpha-amylase derived from *B. amyloliquefaciens* shown in SEQ ID NO 6 of WO 2006/066594 and residues 36-483 of SEQ ID NO 4 are those having the substitutions:

M197T;

H156Y+A181T+N190F+A209V+Q264S; or

G48A+T49I+G107A+H156Y+A181T+N190F+I201F+A209V+Q264S.

Further amylases which are suitable are amylases having SEQ ID NO 6 in WO 99/019467 or polypeptides thereof having 90% sequence identity to SEQ ID NO 6. Preferred polypeptides of SEQ ID NO 6 are those having a substitution, a deletion or an insertion in one or more of the following positions: R181, G182, H183, G184, N195, I206, E212, E216 and K269. Particularly preferred amylases are those having deletion in positions R181 and G182, or positions H183 and G184. Additional amylases which can be used are those having SEQ ID NO 1, SEQ ID NO 3, SEQ ID NO 2 or SEQ ID NO 7 of WO 96/023873 or polypeptides thereof having 90% sequence identity to SEQ ID NO 1, SEQ ID NO 2, SEQ ID NO 3 or SEQ ID NO 7. Preferred polypeptides of SEQ ID NO 1, SEQ ID NO 2, SEQ ID NO 3 or SEQ ID NO 7 are those having a substitution, a deletion or an insertion in one or more of the following positions: 140, 181, 182, 183, 184, 195, 206, 212, 243, 260, 269, 304 and 476. More preferred polypeptides are those having a deletion in positions 181 and 182 or positions 183 and 184. Most preferred amylase polypeptides of SEQ ID NO 1, SEQ ID NO 2 or SEQ ID NO 7 are those having a deletion in positions 183 and 184 and a substitution in one or more of positions 140, 195, 206, 243, 260, 304 and 476. Other amylases which can be used are amylases having SEQ ID NO 2 of WO 08/153815, SEQ ID NO 10 in WO 01/66712 or polypeptides thereof having 90% sequence identity to SEQ ID NO 2 of WO 08/153815 or 90% sequence identity to SEQ ID NO 10 in WO 01/66712. Preferred polypeptides of SEQ ID NO 10 in WO 01/66712 are those having a substitution, a deletion or an insertion in one of more of the following positions: 176, 177, 178, 179, 190, 201, 207, 211 and 264.

Further suitable amylases are amylases having SEQ ID NO 2 of WO 09/061380 or polypeptides having 90% sequence identity to SEQ ID NO 2 thereof. Preferred polypeptides of SEQ ID NO 2 are those having a truncation of the C-terminus and/or a substitution, a deletion or an insertion in one of more of the following positions: Q87, Q98, S125, N128, T131, T165, K178, R180, S181, T182, G183, M201, F202, N225, S243, N272, S282, Y305, R309, D319, Q320, Q359, K444 and G475. More preferred polypeptides of SEQ ID NO 2 are those having the substitution in one of more of the following positions: Q87E,R, Q98R, S125A, N128C, T131I, T165I, K178L, T182G, M201L, F202Y, N225E,R, N272E,R, S243Q,A,E,D, Y305R, R309A, Q320R, Q359E, K444E and G475K and/or deletion in position R180 and/or S181 or of T182 and/or G183. Most preferred amylase polypeptides of SEQ ID NO 2 are those having the substitutions:

N128C+K178L+T182G+Y305R+G475K;

N128C+K178L+T182G+F202Y+Y305R+D319T+G475K;

S125A+N128C+K178L+T182G+Y305R+G475K; or

S125A+N128C+T131I+T165I+K178L+T182G+Y305R+G475K wherein the polypeptides are C-terminally truncated and optionally further comprises a substitution at position 243 and/or a deletion at position 180 and/or position 181.

Other suitable amylases are the alpha-amylase having SEQ ID NO 12 in WO01/66712 or a variant having at least 90% sequence identity to SEQ ID NO 12. Preferred amylase polypeptides are those having a substitution, a deletion or an insertion in one of more of the following positions of SEQ ID NO 12 in WO01/66712: R28, R118, N174; R181, G182, D183, G184, G186, W189, N195, M202, Y298, N299, K302, S303, N306, R310, N314; R320, H324, E345, Y396, R400, W439, R444, N445, K446, Q449, R458, N471, N484. Particular preferred amylases include polypeptides having a deletion of D183 and G184 and having the substitutions R118K, N195F, R320K and R458K, and a variant additionally having substitutions in one or more position selected from the group: M9, G149, G182, G186, M202, T257, Y295, N299, M323, E345 and A339, most preferred a variant that additionally has substitutions in all these positions.

Other examples are amylase polypeptides such as those described in WO2011/098531, WO2013/001078 and WO2013/001087.

Commercially available amylases are Duramyl™, Termamyl™, Fungamyl™, Stainzyme™, Stainzyme Plus™, Natalase™, Liquozyme X and BAN™ (from Novozymes A/S), and Rapidase™ Purastar™/Effectenz™, Powerase and Preferenz S100 (from Genencor International Inc./DuPont).

In addition to the polypeptides having hexosaminidase activity comprising the polypeptides of SEQ ID NO 7, SEQ ID NO 8, SEQ ID NO 9, or a polypeptide having hexosaminidase activity and having at least 60% sequence identity hereto the cleaning composition of the invention may further comprise peroxidases/oxidases including those of plant, bacterial or fungal origin. Chemically modified or protein engineered mutants are included. Examples of useful peroxidases include peroxidases from *Coprinus*, e.g., from *C. cinereus*, and polypeptides thereof as those described in WO 93/24618, WO 95/10602, and WO 98/15257. Commercially available peroxidases include Guardzyme™ (Novozymes A/S).

The cleaning composition enzyme(s) may be included in e.g. a detergent composition by adding separate additives containing one or more enzymes, or by adding a combined additive comprising these enzymes. A detergent additive of the invention, i.e., a separate additive or a combined additive, can be formulated, for example, as a granulate, liquid, slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The detergent compositions of the invention may also contain 0-10% by weight, such as 0.5-5%, 2-5%, 0.5-2% or 0.2-1% of a polymer. Any polymer known in the art for use in detergents may be utilized. The polymer may function as a co-builder as mentioned above, or may provide antiredeposition, fiber protection, soil release, dye transfer inhibition, grease cleaning and/or anti-foaming properties. Some polymers may have more than one of the above-mentioned properties and/or more than one of the below-mentioned motifs. Exemplary polymers include (carboxymethyl)cellulose (CMC), poly(vinyl alcohol) (PVA), poly(vinylpyrrolidone) (PVP), poly(ethyleneglycol) or poly(ethylene oxide) (PEG), ethoxylated poly(ethyleneimine), (carboxymethyl) inulin (CMI), and polycarboxylates such as PAA, PAA/PMA, polyaspartic acid, and lauryl methacrylate/acrylic acid copolymers, hydrophobically modified CMC (HM-CMC) and silicones, copolymers of terephthalic acid and oligomeric glycols, copolymers of poly(ethylene terephthalate) and poly(oxyethene terephthalate) (PET-POET), PVP, poly(vinylimidazole) (PVI), poly(vinylpyridine-N-oxide) (PVPO or PVPNO) and polyvinylpyrrolidone-vinylimidazole (PVPVI). Further exemplary polymers include sulfonated polycarboxylates, polyethylene oxide and polypropylene oxide (PEO-PPO) and diquaternium ethoxy sulfate. Other exemplary polymers are disclosed in, e.g., WO 2006/130575. Salts of the above-mentioned polymers are also contemplated.

The cleaning compositions of the present invention may also include fabric hueing agents such as dyes or pigments, which when formulated in detergent compositions can deposit onto a fabric when said fabric is contacted with a wash liquor comprising said detergent compositions and thus altering the tint of said fabric through absorption/reflection of visible light. Fluorescent whitening agents emit at least some visible light if subjected to ultraviolet light. In contrast, fabric hueing agents alter the tint of a surface as they absorb at least a portion of the visible light spectrum. Suitable fabric hueing agents include dyes and dye-clay conjugates, and may also include pigments. Suitable dyes include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof, for example as described in WO2005/03274, WO2005/03275, WO2005/03276 and EP1876226 (hereby incorporated by reference). The detergent composition preferably comprises from about 0.00003 wt % to about 0.2 wt %, from about 0.00008 wt % to about 0.05 wt %, or even from about 0.0001 wt % to about 0.04 wt % fabric hueing agent. The composition may comprise from 0.0001 wt % to 0.2 wt % fabric hueing agent, this may be especially preferred when the composition is in the form of a unit dose pouch. Suitable hueing agents are also disclosed in, e.g. WO 2007/087257 and WO2007/087243.

The composition may further contain 0-10% by weight, for example 0-5% by weight, such as about 0.5 to about 5%, or about 3% to about 5%, of a hydrotrope. Any hydrotrope known in the art for use in detergents may be utilized. Non-limiting examples of hydrotropes include sodium benzenesulfonate, sodium p-toluene sulfonate (STS), sodium xylene sulfonate (SXS), sodium cumene sulfonate (SCS), sodium cymene sulfonate, amine oxides, alcohols and polyglycolethers, sodium hydroxynaphthoate, sodium hydroxynaphthalene sulfonate, sodium ethylhexyl sulfate, and combinations thereof.

The cleaning compositions of the present invention can also contain dispersants. In particular, powdered detergents may comprise dispersants. Suitable water-soluble organic materials include the homo- or co-polymeric acids or their salts, in which the polycarboxylic acid comprises at least two carboxyl radicals separated from each other by not more than two carbon atoms. Suitable dispersants are for example described in Powdered Detergents, Surfactant science series volume 71, Marcel Dekker, Inc.

The cleaning composition may also include one or more dye transfer inhibiting agents. Suitable polymeric dye transfer inhibiting agents include, but are not limited to, polyvinylpyrrolidone polymers, polyamine-N-oxide polymers, copolymers of N-vinylpyrrolidone and N-vinylimidazole, polyvinyloxazolidones and polyvinylimidazoles or mixtures thereof. When present in a subject composition, the dye transfer inhibiting agents may be present at levels from about 0.0001% to about 10%, from about 0.01% to about 5% or even from about 0.1% to about 3% by weight of the composition.

The cleaning compositions may preferably also contain additional components that may tint articles being cleaned, such as fluorescent whitening agent or optical brighteners. Where present the brightener is preferably at a level of about 0.01% to about 0.5%. Any fluorescent whitening agent suitable for use in a laundry detergent composition may be used in a laundry composition. The most commonly used fluorescent whitening agents are those belonging to the classes of diaminostilbene-sulfonic acid derivatives, diarylpyrazoline derivatives and biphenyl-distyryl derivatives. Examples of the diaminostilbene-sulfonic acid derivative type of fluorescent whitening agents include the sodium salts of: 4,4'-bis[(4-anilino-6-diethanolamino-s-triazin-2-yl)amino]stilbene-2,2'-disulfonate, 4,4'-bis[(4,6-dianilino-s-triazin-2-yl)amino]stilbene-2,2'-disulfonate, 4,4'-bis{4-anilino-6-[methyl(2-hydroxyethyl)amino]-s-triazin-2-ylamino}stilbene-2,2'-disulfonate, 4,4'-bis(4-phenyl-1,2,3-triazol-2-yl)stilbene-2,2'-disulfonate and sodium 5-(2H-naphtho[1,2-d][1,2,3]triazol-2-yl)-2-[(E)-2-phenylvinyl]benzenesulfonate. Preferred fluorescent whitening agents are Tinopal DMS and Tinopal CBS available from BASF. Tinopal DMS is the disodium salt of 4,4'-bis[(4-anilino-6-morpholino-s-triazin-2-yl)amino]stilbene-2,2'-disulfonate. Tinopal CBS is the disodium salt of 2,2'-[biphenyl-4,4'-di (2,1-ethenediyl)]dibenzene-1-sulfonate. Also preferred is the commercially available Parawhite KX, supplied by Paramount Minerals and Chemicals, Mumbai, India. Other fluorescers suitable for use include the 1-3-diarylpyrazolines and the 7-alkylaminocoumarins.

Suitable fluorescent brightener levels include lower levels of from about 0.01, from 0.05, from about 0.1 or even from about 0.2 wt % to upper levels of 0.5 or even 0.75 wt %.

The cleaning composition may also include one or more soil-release polymers which aid the removal of soils from fabrics such as cotton and polyester-based fabrics, in particular the removal of hydrophobic soils from polyester-based fabrics. The soil release polymers may for example be nonionic or anionic terephthalate-based polymers, polyvinylcaprolactam and related copolymers, vinyl graft copolymers or polyester polyamides; see for example Chapter 7 in Powdered Detergents, Surfactant science series volume 71, Marcel Dekker, Inc. Another type of soil release polymers is amphiphilic alkoxylated grease cleaning polymers comprising a core structure and a plurality of alkoxylate groups attached to that core structure. The core structure may comprise a polyalkylenimine structure or a polyalkanolamine structure as described in detail in WO 2009/087523 (hereby incorporated by reference). Furthermore, random graft co-polymers are suitable soil-release polymers. Suitable graft co-polymers are described in more detail in WO 2007/138054, WO 2006/108856 and WO 2006/113314 (hereby incorporated by reference). Other soil-release polymers are substituted polysaccharide structures especially substituted cellulosic structures such as modified cellulose derivatives such as those described in EP 1867808 or WO 2003/040279 (both are hereby incorporated by reference). Suitable cellulosic polymers include cellulose, cellulose ethers, cellulose esters, cellulose amides and mixtures thereof. Suitable cellulosic polymers include anionically modified cellulose, nonionically modified cellulose, cationically modified cellulose, zwitterionically modified cellulose, and mixtures thereof.

The cleaning compositions may also include one or more anti-redeposition agents such as (carboxymethyl) cellulose (CMC), poly(vinyl alcohol) (PVA), homopolymers of acrylic acid, copolymers of acrylic acid and maleic acid, and ethoxylated polyethyleneimines. The cellulose based polymers described under soil-release polymers above may also function as anti-redeposition agents.

The cleaning composition may also contain one are more adjunct material. Suitable adjunct materials include, but are not limited to, anti-shrink agents, anti-wrinkling agents, bactericides, binders, carriers, dyes, enzyme stabilizers, fabric softeners, fillers, foam regulators, hydrotropes, perfumes, pigments, sod suppressors, solvents, and structurants for liquid detergents and/or structure elasticizing agents.

The cleaning composition may be in any convenient form, e.g., a bar, a homogenous tablet, a tablet having two or more layers, a pouch having one or more compartments, a regular or compact powder, a granule, a paste, a gel, or a regular, compact or concentrated liquid.

Pouches can be configured as single or multicompartments. It can be of any form, shape and material which is suitable for hold the composition, e.g. without allowing the release of the composition to release of the composition from the pouch prior to water contact. The pouch is made from water soluble film which encloses an inner volume. Said inner volume can be divided into compartments of the pouch. Preferred films are polymeric materials preferably polymers which are formed into a film or sheet. Preferred polymers, copolymers or derivates thereof are selected polyacrylates, and water soluble acrylate copolymers, methyl cellulose, carboxy methyl cellulose, sodium dextrin, ethyl cellulose, hydroxyethyl cellulose, hydroxypropyl methyl cellulose, malto dextrin, poly methacrylates, most preferably polyvinyl alcohol copolymers and, hydroxypropyl methyl cellulose (HPMC). Preferably the level of polymer in the film for example PVA is at least about 60%. Preferred average molecular weight will typically be about 20,000 to about 150,000. Films can also be of blended compositions comprising hydrolytically degradable and water soluble polymer blends such as polylactide and polyvinyl alcohol (known under the Trade reference M8630 as sold by Mono-Sol LLC, Indiana, USA) plus plasticisers like glycerol, ethylene glycerol, propylene glycol, sorbitol and mixtures thereof. The pouches can comprise a solid laundry cleaning composition or part components and/or a liquid cleaning composition or part components separated by the water-soluble film. The compartment for liquid components can be different in composition than compartments containing solids: US2009/0011970 A1.

Detergent ingredients can be separated physically from each other by compartments in water dissolvable pouches or in different layers of tablets. Thereby negative storage interaction between components can be avoided. Different dissolution profiles of each of the compartments can also give rise to delayed dissolution of selected components in the wash solution.

A liquid or gel detergent, which is not unit dosed, may be aqueous, typically containing at least 20% by weight and up to 95% water, such as up to about 70% water, up to about 65% water, up to about 55% water, up to about 45% water, up to about 35% water. Other types of liquids, including without limitation, alkanols, amines, diols, ethers and polyols may be included in an aqueous liquid or gel. An aqueous liquid or gel detergent may contain from 0-30% organic solvent.

The present invention is also directed to methods for using the polypeptides according to the invention or compositions thereof in laundering of textile and fabrics, such as house hold laundry washing and industrial laundry washing.

One aspect of the invention relates to a method for laundering an item comprising:
 a) expose of an item to a wash liquor comprising a polypeptide selected from the group consisting of polypeptides shown in SEQ ID NO 7, SEQ ID NO 8, SEQ ID NO 9, SEQ ID NO 10 and SEQ ID NO 11 or expose of an item to a detergent composition according to any of claims 1 to 14;

b) completing at least one wash cycle; and optionally rinsing the item, wherein the item is a textile.

The invention is also directed to methods for using the polypeptides according to the invention or compositions thereof in cleaning hard surfaces such as floors, tables, walls, roofs etc. as well as surfaces of hard objects such as cars (car wash) and dishes (dish wash).

The polypeptides of the present invention may be added to and thus become a component of a cleaning composition. One aspect of the invention relates to the use of a polypeptide having hexosaminidase activity optionally comprising one or more motif(s) selected from the group consisting of GXDE (SEQ ID NO 18), [EQ][NRSHA][YVFL][AGSTC][IVLF][EAQYN][SN] (SEQ ID NO 19), [VIM][LIV]G[GAV]DE[VI][PSA] (SEQ ID NO: 20), WND[SQR][IVL][TLVM] (SEQ ID NO: 21), QSTL (SEQ ID NO 22), NKFFY (SEQ ID NO: 23), NLD[DR]S (SEQ ID NO: 24), wherein the polypeptide is selected from the group consisting of SEQ ID NO 7, SEQ ID NO 8, SEQ ID NO 9, SEQ ID NO 10, SEQ ID NO 11 and polypeptides having at least 60% sequence identity hereto having hexosaminidase activity in a cleaning process such as laundering and/or hard surface cleaning.

Thus, one aspect of the invention relates to the use of the use of a polypeptide having hexosaminidase activity, optionally comprising one or more motif(s) selected from the group consisting of GXDE (SEQ ID NO 18), [EQ][NRSHA][YVFL][AGSTC][IVLF][EAQYN][SN] (SEQ ID NO 19), [VIM][LIV]G[GAV]DE[VI][PSA] (SEQ ID NO: 20), WND[SQR][IVL][TLVM] (SEQ ID NO: 21), QSTL (SEQ ID NO 22), NKFFY (SEQ ID NO: 23), NLD[DR]S (SEQ ID NO: 24), wherein the polypeptide is selected from the group consisting of SEQ ID NO 7, SEQ ID NO 8, SEQ ID NO 9, SEQ ID NO 10, SEQ ID NO 11 and polypeptides having at least 60% sequence identity in a cleaning process such as laundering and/or hard surface cleaning and wherein the polypeptide has improved deep cleaning properties, relative to a reference enzyme.

The cleaning process or the textile care process may for example be a laundry process, a dishwashing process or cleaning of hard surfaces such as bathroom tiles, floors, table tops, drains, sinks and washbasins. Laundry processes can for example be household laundering, but it may also be industrial laundering. Furthermore, the invention relates to a process for laundering of fabrics and/or garments where the process comprises treating fabrics with a washing solution containing a cleaning composition, and at least one polypeptide of the invention. The cleaning process or a textile care process can for example be carried out in a machine washing process or in a manual washing process. The washing solution can for example be an aqueous washing solution containing a detergent composition.

The polypeptides comprised in the *Terribacillus* clade are thus particularly useful in composition comprising surfactants such as detergent compositions and the polypeptides of the invention may preferably be used in cleaning processes such as laundry and dish wash.

In some aspects, the present invention relates to polypeptides of the clade of *Terribacillus* having a sequence identity to the mature polypeptide of SEQ ID NO 2 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have hexosaminidase activity. In one aspect, the polypeptides differ by up to 10 amino acids, e.g., 1, 2, 3, 4, 5, 6, 7, 8, 9, or 10, from the mature polypeptide shown in SEQ ID NO 7.

In some aspects, the present invention relates to polypeptides of the clade of *Terribacillus* having a sequence identity to the mature polypeptide of SEQ ID NO 4 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have hexosaminidase activity. In one aspect, the polypeptides differ by up to 10 amino acids, e.g., 1, 2, 3, 4, 5, 6, 7, 8, 9, or 10, from the mature polypeptide shown in SEQ ID NO 8.

In some aspects, the present invention relates to polypeptides of the clade of *Terribacillus* having a sequence identity to the mature polypeptide of SEQ ID NO 6 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have hexosaminidase activity. In one aspect, the polypeptides differ by up to 10 amino acids, e.g., 1, 2, 3, 4, 5, 6, 7, 8, 9, or 10, from the mature polypeptide shown in SEQ ID NO 9.

In some aspects, the present invention relates to polypeptides of the clade of *Terribacillus* having a sequence identity to the mature polypeptide of SEQ ID NO 13 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have hexosaminidase activity. In one aspect, the polypeptides differ by up to 10 amino acids, e.g., 1, 2, 3, 4, 5, 6, 7, 8, 9, or 10, from the mature polypeptide shown in SEQ ID NO 10.

In some aspects, the present invention relates to polypeptides of the clade of *Terribacillus* having a sequence identity to the mature polypeptide of SEQ ID NO 14 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have hexosaminidase activity. In one aspect, the polypeptides differ by up to 10 amino acids, e.g., 1, 2, 3, 4, 5, 6, 7, 8, 9, or 10, from the mature polypeptide shown in SEQ ID NO 11.

In an embodiment, the polypeptide has been isolated. A polypeptide of the present invention preferably comprises or consists of the amino acid sequence of SEQ ID NO 7 or an allelic variant thereof; or is a fragment thereof having hexosaminidase activity. In another aspect, the polypeptide comprises or consists of the mature polypeptide of SEQ ID NO 2. In another aspect, the polypeptide comprises or consists of amino acids 1 to 324 of SEQ ID NO 2.

In an embodiment, the polypeptide has been isolated. A polypeptide of the present invention preferably comprises or consists of the amino acid sequence of SEQ ID NO 8 or an allelic variant thereof; or is a fragment thereof having hexosaminidase activity. In another aspect, the polypeptide comprises or consists of the mature polypeptide of SEQ ID NO 4. In another aspect, the polypeptide comprises or consists of amino acids 1 to 324 of SEQ ID NO 4.

In an embodiment, the polypeptide has been isolated. A polypeptide of the present invention preferably comprises or consists of the amino acid sequence of SEQ ID NO 9 or an allelic variant thereof; or is a fragment thereof having hexosaminidase activity. In another aspect, the polypeptide comprises or consists of the mature polypeptide of SEQ ID NO 6. In another aspect, the polypeptide comprises or consists of amino acids 1 to 324 of SEQ ID NO 6.

In an embodiment, the polypeptide has been isolated. A polypeptide of the present invention preferably comprises or consists of the amino acid sequence of SEQ ID NO 10 or an allelic variant thereof; or is a fragment thereof having hexosaminidase activity. In another aspect, the polypeptide comprises or consists of the mature polypeptide of SEQ ID NO 13. In another aspect, the polypeptide comprises or consists of amino acids 1 to 324 of SEQ ID NO 13.

In an embodiment, the polypeptide has been isolated. A polypeptide of the present invention preferably comprises or consists of the amino acid sequence of SEQ ID NO 11 or an allelic variant thereof; or is a fragment thereof having hexosaminidase activity. In another aspect, the polypeptide comprises or consists of the mature polypeptide of SEQ ID NO 15. In another aspect, the polypeptide comprises or consists of amino acids 1 to 324 of SEQ ID NO 15.

In another embodiment, the present invention relates to a polypeptide having hexosaminidase activity encoded by a polynucleotide that hybridizes under very low stringency conditions, low stringency conditions, medium stringency conditions, medium-high stringency conditions, high stringency conditions, or very high stringency conditions with (i) the mature polypeptide coding sequence of SEQ ID NO 1, 3, 5, 12 or 14 or (ii) the full-length complement of (i) (Sambrook et al., 1989, *Molecular Cloning, A Laboratory Manual*, 2d edition, Cold Spring Harbor, New York). In an embodiment, the polypeptide has been isolated.

The polynucleotide of SEQ ID NO 1, SEQ ID NO 3, SEQ ID NO 5, SEQ ID NO 12 or SEQ ID NO 14 or a subsequence thereof, as well as the mature polypeptide of SEQ ID NO 2, SEQ ID NO 4, SEQ ID NO 6, SEQ ID NO 13, SEQ ID NO 15 or a fragment thereof may be used to design nucleic acid probes to identify and clone DNA encoding polypeptides having hexosaminidase activity from strains of different genera or species according to methods well known in the art. Such probes can be used for hybridization with the genomic DNA or cDNA of a cell of interest, following standard Southern blotting procedures, to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may be screened for DNA that hybridizes with the probes described above and encodes a polypeptide having hexosaminidase activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. To identify a clone or DNA that hybridizes with SEQ ID NO 1, 3, 5, 12 or 14 or a subsequence thereof, the carrier material is used in a Southern blot.

For purposes of the present invention, hybridization indicates that the polynucleotide hybridizes to a labeled nucleic acid probe corresponding to (i) SEQ ID NO 1, SEQ ID NO 3, SEQ ID NO 5, SEQ ID NO 12 or SEQ ID NO 14; (ii) the mature polypeptide coding sequence of SEQ ID NO 1, SEQ ID NO 3, SEQ ID NO 5, SEQ ID NO 12 or SEQ ID NO 14; (iii) the full-length complement thereof; or (iv) a subsequence thereof; under very low to very high stringency conditions. Molecules to which the nucleic acid probe hybridizes under these conditions can be detected using, for example, X-ray film or any other detection means known in the art.

In another embodiment, the present invention relates to a polypeptide having hexosaminidase activity encoded by a polynucleotide having a sequence identity to the mature polypeptide coding sequence of SEQ ID NO 1 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polypeptide has been isolated.

In another embodiment, the present invention relates to a polypeptide having hexosaminidase activity encoded by a polynucleotide having a sequence identity to the mature polypeptide coding sequence of SEQ ID NO 3 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polypeptide has been isolated.

In another embodiment, the present invention relates to a polypeptide having hexosaminidase activity encoded by a polynucleotide having a sequence identity to the mature polypeptide coding sequence of SEQ ID NO 5 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polypeptide has been isolated.

In another embodiment, the present invention relates to a polypeptide having hexosaminidase activity encoded by a polynucleotide having a sequence identity to the mature polypeptide coding sequence of SEQ ID NO 12 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polypeptide has been isolated.

In another embodiment, the present invention relates to a polypeptide having hexosaminidase activity encoded by a polynucleotide having a sequence identity to the mature polypeptide coding sequence of SEQ ID NO 14 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polypeptide has been isolated.

In another embodiment, the present invention relates to variants of the mature polypeptide of SEQ ID NO 2, SEQ ID NO 4, SEQ ID NO 6, SEQ ID NO 13 or SEQ ID NO 15 comprising a substitution, deletion, and/or insertion at one or more (e.g., several) positions. In an embodiment, the number of amino acid substitutions, deletions and/or insertions introduced into the mature polypeptide of SEQ ID NO 7, SEQ ID NO 8, SEQ ID NO 9, SEQ ID NO 10 or SEQ ID NO 11 is up to 10, e.g., 1, 2, 3, 4, 5, 6, 7, 8, 9, or 10. The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain. Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like. Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant molecules are tested for hexosaminidase activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide. The polypeptides of the invention are hexosaminidase e.g. dispersins belonging to the *Terribacillus* clade. *Terribacillus* dispersins are β-hexosaminidases that specifically hydrolyzes β-1,6-glycosidic linkages of N-acetylglucosamine polymers, which may be found e.g. in biofilm. Dispersin B which belongs to a different clade than the polypeptides (hexosaminidases) of the invention contains three highly conserved acidic residues: an aspartic acid at residue 183 (D183), a glutamic acid at residue 184 (E184), and a glutamic acid at residue 332 (E332). Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage Display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127). Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide. The polypeptide may be a hybrid polypeptide in which a region of one polypeptide is fused at the N-terminus or the C-terminus of a region of another polypeptide.

The polypeptide may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779). A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

Sources of Polypeptides Having Hexosaminidase Activity

A polypeptide having hexosaminidase activity of the present invention may be obtained from microorganisms of any genus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

In another aspect, the polypeptide is a *Terribacillus* polypeptide, e.g., a polypeptide obtained from *Terribacillus saccharophilus*. In a preferred aspect, the polypeptide is a polypeptide having at least 80% sequence identity to SEQ ID NO 7 and is obtained from *Terribacillus* preferably *Terribacillus saccharophilus*.

In another aspect, the polypeptide is a *Terribacillus* polypeptide, e.g., a polypeptide obtained from *Terribacillus goriensis*. In a preferred aspect, the polypeptide is a polypeptide having at least 80% sequence identity to SEQ ID NO 8 and is obtained from *Terribacillus* preferably *Terribacillus goriensis*.

In another aspect, the polypeptide is a *Terribacillus* polypeptide, e.g., a polypeptide obtained from *Terribacillus saccharophilus*. In a preferred aspect, the polypeptide is a polypeptide having at least 80% sequence identity to SEQ ID NO 9 and is obtained from *Terribacillus* preferably *Terribacillus saccharophilus*.

In another aspect, the polypeptide is a *Terribacillus* polypeptide, e.g., a polypeptide obtained from *Terribacillus saccharophilus*. In a preferred aspect, the polypeptide is a polypeptide having at least 80% sequence identity to SEQ ID NO 10 and is obtained from *Terribacillus* preferably *Terribacillus saccharophilus*.

In another aspect, the polypeptide is a *Terribacillus* polypeptide, e.g., a polypeptide obtained from *Terribacillus saccharophilus*. In a preferred aspect, the polypeptide is a polypeptide having at least 80% sequence identity to SEQ ID NO 11 and is obtained from *Terribacillus* preferably *Terribacillus saccharophilus*.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are known to those of ordinary skill in the art (see, e.g., Sambrook et al., 1989, supra).

Nucleic Acid Constructs

The present invention also relates to nucleic acid constructs comprising a polynucleotide of the present invention operably linked to one or more control sequences that direct the expression of the coding sequence in a suitable host cell under conditions compatible with the control sequences.

The polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including variant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and variant, truncated, and hybrid promoters thereof. Other promoters are described in U.S. Pat. No. 6,011,147.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* acetamidase, *Aspergillus nidulans* anthranilate synthase, *Aspergillus niger* glucoamylase, *Aspergillus niger* alpha-glucosidase,

*Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor. Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra. The control sequence may also be an mRNA stabilizer region downstream of a promoter and upstream of the coding sequence of a gene which increases expression of the gene. Examples of suitable mRNA stabilizer regions are obtained from a *Bacillus thuringiensis* cryIIIA gene (WO 94/25612) and a *Bacillus subtilis* SP82 gene (Hue et al., 1995, Journal of Bacteriology 177: 3465-3471). The control sequence may also be a leader, a nontranslated region of an mRNA that is important for translation by the host cell. The leader is operably linked to the 5'-terminus of the polynucleotide encoding the polypeptide. Any leader that is functional in the host cell may be used. Preferred leaders for filamentous fungal host cells are obtained from the genes for *Aspergillus oryzae* TAKA amylase and *Aspergillus nidulans* triose phosphate isomerase. Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP). The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used. Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease. Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCI B 11837 maltogenic amylase, *Bacillus licheniformis* Subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, Microbiological Reviews 57: 109-137. Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase. Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory sequences are those that cause expression of the gene to be turned on or off in response to a chemical or physical stimulus, including the presence of a regulatory compound. Regulatory sequences in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked to the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, adeA (phosphoribosylaminoimidazole-succinocarboxamide synthase), adeB (phosphoribosylaminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes.

The selectable marker may be a dual selectable marker system as described in WO 2010/039889. In one aspect, the dual selectable marker is an hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus altitudinis, Bacillus amyloliquefaciens, B. amyloliquefaciens* subsp. *plantarum, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus methylotrophicus, Bacillus pumilus, Bacillus safensis, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol. (Praha)* 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397) or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804), or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, Passmore, and Davenport, editors, *Soc. App. Bacteriol. Symposium Series* No. 9, 1980).

The yeast host cell may be a *Candida, Hansenula, Kluyveromyces, Pichia, Saccharomyces, Schizosaccharomyces*, or *Yarrowia* cell, such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phiebia, Piromyces, Pleurotus, Schizophyllum, Talaromyces, Thermoascus, Thielavia, Tolypocladium, Trametes*, or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phiebia radiata, Pleurotus eryngii, Thielavia terrestris, Trametes villosa, Trametes versicolor, Trichoderma harzianum, Trichoderma koningii Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known per se.

Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a polypeptide of the present invention, comprising (a) cultivating a cell, which in its wild-type form produces the polypeptide, under conditions conducive for production of the polypeptide; and optionally, (b) recovering the polypeptide. In one aspect, the cell is a *Terribacillus* cell. In another aspect, the cell is a *Terribacillus saccharophilus* cell. In one aspect, the cell is a *Terribacillus* cell. In another aspect, the cell is a *Terribacillus goriensis* cell.

The present invention also relates to methods of producing a polypeptide of the present invention, comprising (a) cultivating a recombinant host cell of the present invention under conditions conducive for production of the polypeptide; and optionally, (b) recovering the polypeptide.

The host cells are cultivated in a nutrient medium suitable for production of the polypeptide using methods known in the art. For example, the cells may be cultivated by shake flask cultivation, or small-scale or large-scale fermentation (including continuous, batch, fed-batch, or solid state fermentations) in laboratory or industrial fermentors in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides having hexosaminidase activity. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation. In one aspect, a fermentation broth comprising the polypeptide is recovered.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure polypeptides.

In an alternative aspect, the polypeptide is not recovered, but rather a host cell of the present invention expressing the polypeptide is used as a source of the polypeptide.

Formulation of Detergent Products

The cleaning composition may be in any convenient form, e.g., a bar, a homogenous tablet, a tablet having two or more layers, a pouch having one or more compartments, a regular or compact powder, a granule, a paste, a gel, or a regular, compact or concentrated liquid. Pouches can be configured as single or multicompartments. It can be of any form, shape and material which is suitable for hold the composition, e.g. without allowing the release of the composition to release of the composition from the pouch prior to water contact. The pouch is made from water soluble film which encloses an inner volume. Said inner volume can be divided into compartments of the pouch. Preferred films are polymeric materials preferably polymers which are formed into a film or sheet. Preferred polymers, copolymers or derivates thereof are selected polyacrylates, and water soluble acrylate copolymers, methyl cellulose, carboxy methyl cellulose, sodium dextrin, ethyl cellulose, hydroxyethyl cellulose, hydroxypropyl methyl cellulose, malto dextrin, poly methacrylates, most preferably polyvinyl alcohol copolymers and, hydroxypropyl methyl cellulose (HPMC). Preferably the level of polymer in the film for example PVA is at least about 60%. Preferred average molecular weight will typically be about 20,000 to about 150,000. Films can also be of blended compositions comprising hydrolytically degradable and water soluble polymer blends such as polylactide and polyvinyl alcohol (known under the Trade reference M8630 as sold by MonoSol LLC, Indiana, USA) plus plasticisers like glycerol, ethylene glycerol, propylene glycol, sorbitol and mixtures thereof. The pouches can comprise a solid laundry cleaning composition or part components and/or a liquid cleaning composition or part components separated by the water soluble film. The compartment for liquid components can be different in composition than compartments containing solids: US2009/0011970 A1.

Detergent ingredients can be separated physically from each other by compartments in water dissolvable pouches or in different layers of tablets. Thereby negative storage interaction between components can be avoided. Different dissolution profiles of each of the compartments can also give rise to delayed dissolution of selected components in the wash solution.

A liquid or gel detergent, which is not unit dosed, may be aqueous, typically containing at least 20% by weight and up to 95% water, such as up to about 70% water, up to about 65% water, up to about 55% water, up to about 45% water, up to about 35% water. Other types of liquids, including without limitation, alkanols, amines, diols, ethers and polyols may be included in an aqueous liquid or gel. An aqueous liquid or gel detergent may contain from 0-30% organic solvent.

A liquid or gel detergent may be non-aqueous.

Laundry Soap Bars

The polypeptides of the invention may be added to laundry soap bars and used for hand washing laundry, fabrics and/or textiles. The term laundry soap bar includes laundry bars, soap bars, combo bars, syndet bars and detergent bars. The types of bar usually differ in the type of surfactant they contain, and the term laundry soap bar includes those containing soaps from fatty acids and/or synthetic soaps. The laundry soap bar has a physical form which is solid and not a liquid, gel or a powder at room temperature. The term solid is defined as a physical form which does not significantly change over time, i.e. if a solid object (e.g. laundry soap bar) is placed inside a container, the solid object does not change to fill the container it is placed in. The bar is a solid typically in bar form but can be in other solid shapes such as round or oval. The laundry soap bar may contain one or more additional enzymes, protease inhibitors such as peptide aldehydes (or hydrosulfite adduct or hemiacetal adduct), boric acid, borate, borax and/or phenylboronic acid derivatives such as 4-formylphenylboronic acid, one or more soaps or synthetic surfactants, polyols such as glycerine, pH controlling compounds such as fatty acids, citric acid, acetic acid and/or formic acid, and/or a salt of a monovalent cation and an organic anion wherein the monovalent cation may be for example $Na^+$, $K^+$ or $NH_4^+$ and the organic anion may be for example formate, acetate, citrate or lactate such that the salt of a monovalent cation and an organic anion may be, for example, sodium formate. The laundry soap bar may also contain complexing agents like EDTA and HEDP, perfumes and/or different type of fillers, surfactants e.g. anionic synthetic surfactants, builders, polymeric soil release agents, detergent chelators, stabilizing agents, fillers, dyes, colorants, dye transfer inhibitors, alkoxylated polycarbonates, suds suppressers, structurants, binders, leaching agents, bleaching activators, clay soil removal agents, anti-redeposition agents, polymeric dispersing agents, brighteners, fabric softeners, perfumes and/or other compounds known in the art. The laundry soap bar may be processed in conventional laundry soap bar making equipment such as but not limited to: mixers, plodders, e.g a two stage vacuum plodder, extruders, cutters, logo-stampers, cooling tunnels and wrappers. The invention is not limited to preparing the laundry soap bars by any single method. The premix may be added to the soap at different stages of the process. For example, the premix containing a soap, hexosaminidase, optionally one or more additional enzymes, a protease inhibitor, and a salt of a monovalent cation and an organic anion may be prepared and the mixture is then plodded. The hexosaminidase and optional additional enzymes may be added at the same time as the protease inhibitor for example in liquid form. Besides the mixing step and the plodding step, the process may further comprise the steps of milling, extruding, cutting, stamping, cooling and/or wrapping.

Formulation of Enzyme in Co-Granule

The polypeptides of the invention may be formulated as a granule for example as a co-granule that combines one or more enzymes. Each enzyme will then be present in more granules securing a more uniform distribution of enzymes in the detergent. This also reduces the physical segregation of different enzymes due to different particle sizes. Methods for producing multi-enzyme co-granulates for the detergent industry are disclosed in the IP.com disclosure IPCOM000200739D. Another example of formulation of enzymes using co-granulates are disclosed in WO 2013/188331, which relates to a detergent composition comprising (a) a multi-enzyme co-granule; (b) less than 10 wt zeolite (anhydrous basis); and (c) less than 10 wt phosphate salt (anhydrous basis), wherein said enzyme co-granule comprises from 10 to 98 wt % moisture sink components and the composition additionally comprises from 20 to 80 wt % detergent moisture sink components. The multi-enzyme co-granule may comprise a hexosaminidase and one or more enzymes selected from the group consisting of lipases, cellulases, xyloglucanases, perhydrolases, peroxidases, lipoxygenases, laccases, hemicellulases, proteases, cellobiose dehydrogenases, xylanases, phospho lipases, esterases, cutinases, pectinases, mannanases, pectate lyases, keratinases, reductases, oxidases, phenoloxidases, ligninases, pullulanases, tannases, pentosanases, lichenases glucanases, arabinosidases, hyaluronidase, chondroitinase, amylases, and mixtures thereof.

The invention is further summarized in the following paragraphs:

1. Use of a polypeptide having hexosaminidase activity preferably comprising one or more of the motif(s) GXDE (SEQ ID NO 18), [EQ][NRSHA][YVFL][AGSTC][IVLF][EAQYN][SN] (SEQ ID NO 19), [VIM][LIV]G[GAV]DE[VI][PSA] (SEQ ID NO: 20), WND[SQR][IVL][TLVM] (SEQ ID NO: 21), QSTL (SEQ ID NO 22), NKFFY (SEQ ID NO: 23) or NLD[DR]S (SEQ ID NO: 24) for deep cleaning of an item, wherein the item is a textile.
2. Use according to paragraph 1 for preventing, reducing or removing stickiness of the item.
3. Use according to any of paragraphs 1 or 2 for pre-treating stains on the item.
4. Use according to any of paragraphs 1-3 for preventing, reducing or removing re-deposition of soil during a wash cycle.
5. Use according to any of paragraphs 1-4 for preventing, reducing or removing adherence of soil to the item.
6. Use according to any of the preceding paragraphs for maintaining or improving the whiteness of the item.
7. Use according to any of the preceding paragraphs, wherein a malodor is reduced or removed from the item.
8. Use according to any of the preceding composition paragraphs, wherein the surface is a textile surface.
9. Use according to any of the preceding composition paragraphs, wherein the textile is made of cotton, Cotton/Polyester, Polyester, Polyamide, Polyacryl and/or silk.
10. Use according to any of the preceding paragraphs, wherein the polypeptide is a polypeptide of paragraphs 47-61
11. A composition comprising a polypeptide having hexosaminidase activity preferably comprising one or more of the motif(s) GXDE (SEQ ID NO 18), [EQ][NRSHA][YVFL][AGSTC][IVLF][EAQYN][SN] (SEQ ID NO 19), [VIM][LIV]G[GAV]DE[VI][PSA] (SEQ ID NO: 20), WND[SQR][IVL][TLVM] (SEQ ID NO: 21), QSTL (SEQ ID NO 22), NKFFY (SEQ ID NO: 23) or NLD[DR]S (SEQ ID NO: 24) and an adjunct ingredient.
12. Composition according to paragraph 11, wherein the polypeptide is the polypeptide of paragraphs 47-61.
13. Composition according to any of the preceding composition paragraphs, wherein the detergent adjunct ingredient is selected from the group consisting of surfactants, builders, flocculating aid, chelating agents, dye transfer inhibitors, enzymes, enzyme stabilizers, enzyme inhibitors, catalytic materials, bleach activators, hydrogen peroxide, sources of hydrogen peroxide, preformed peracids, polymeric dispersing agents, clay soil removal/anti-redeposition agents, brighteners, suds suppressors, dyes, perfumes, structure elasticizing agents, fabric softeners, carriers, hydrotropes, builders and co-builders, fabric huing agents, anti-foaming agents, dispersants, processing aids, and/or pigments.
14. Composition according to any of the preceding composition paragraphs wherein the composition comprises from about 5 wt % to about 50 wt %, from about 5 wt % to about 40 wt %, from about 5 wt % to about 30 wt %, from about 5 wt % to about 20 wt %, from about 5 wt % to about 10 wt % anionic surfactant, preferably selected from linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or salt of fatty acids (soap), and combinations thereof.

15. Composition according to any of the preceding composition paragraphs wherein the composition comprises from about 10 wt % to about 50 wt % of at least one builder, preferably selected from citric acid, methylglycine-N, N-diacetic acid (MGDA) and/or glutamic acid-N, N-diacetic acid (GLDA) and mixtures thereof.

16. Composition according to any of the preceding composition paragraphs wherein the polypeptide having hexosaminidase activity is selected from the group consisting of polypeptides having the amino acid sequence of SEQ ID NO 7, SEQ ID NO 8, SEQ ID NO 9, SEQ ID NO 10, SEQ ID NO 11 and polypeptides having at least 60% e.g. 80%, 85%, 90%, 95%, 98% or 99% sequence identity hereto.

17. Composition according to any of the preceding composition paragraphs wherein the polypeptide having hexosaminidase activity is the amino acid sequence of SEQ ID NO 7 or polypeptides having at least 60% e.g. 80%, 85%, 90%, 95%, 98% or 99% sequence identity hereto.

18. Composition according to any of the paragraphs 11 to 16, wherein the polypeptide having hexosaminidase activity is the amino acid sequence of SEQ ID NO 8 or polypeptides having at least 60% e.g. 80%, 85%, 90%, 95%, 98% or 99% sequence identity hereto.

19. Composition according to any of the paragraphs 11 to 16, wherein the polypeptide having hexosaminidase activity is the amino acid sequence of SEQ ID NO 9 or polypeptides having at least 60% e.g. 80%, 85%, 90%, 95%, 98% or 99% sequence identity hereto.

20. Composition according to any of the paragraphs 11 to 16, wherein the polypeptide having hexosaminidase activity is the amino acid sequence of SEQ ID NO 10 or polypeptides having at least 60% e.g. 80%, 85%, 90%, 95%, 98% or 99% sequence identity hereto.

21. Composition according to any of the paragraphs 11 to 16, wherein the polypeptide having hexosaminidase activity is the amino acid sequence of SEQ ID NO 11 or polypeptides having at least 60% e.g. 80%, 85%, 90%, 95%, 98% or 99% sequence identity hereto 22. Composition according to any of the preceding paragraphs comprising from about 5 wt % to about 40 wt % nonionic surfactants, and from about 0 wt % to about 5 wt % anionic surfactants.

23. Composition according to paragraph 22, wherein the nonionic surfactant is selected from alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxyalkyl fatty acid amides, or N-acyl N-alkyl derivatives of glucosamine (glucamides, GA, or fatty acid glucamides, FAGA) and combinations thereof.

24. Composition according to any of the preceding composition paragraphs, wherein the composition further comprises one or more enzymes selected from the group consisting of proteases, lipases, cutinases, amylases, carbohydrases, cellulases, pectinases, mannanases, arabinases, galactanases, xylanases and oxidases.

25. Composition according to any of the preceding composition paragraphs, wherein the enzyme is a protease, which is of animal, vegetable or microbial origin.

26. Composition according to any of the preceding composition paragraphs, wherein the protease is chemically modified or protein engineered.

27. Composition according to any of the preceding composition paragraphs, wherein the protease is a serine protease or a metalloprotease, preferably an alkaline microbial protease or a trypsin-like protease.

28. Composition according to any of the preceding composition paragraphs, wherein the protease is selected from the group consisting of *Bacillus*, e.g., *Subtilisin Novo*, *Subtilisin Carlsberg*, *Subtilisin* 309, *Subtilisin* 147, *Subtilisin* 168, trypsin of bovine origin, trypsin of porcine origin and *Fusarium* protease.

29. Composition according to any of the preceding composition paragraphs, wherein the composition is capable of reducing adhesion of EPS from bacteria selected from the group consisting of *Acinetobacter* sp., *Aeromicrobium* sp., *Brevundimonas* sp., *Microbacterium* sp., *Micrococcus luteus*, *Pseudomonas* sp., *Staphylococcus epidermidis*, *Staphylococcus aureus* and *Stenotrophomonas* sp. to a surface, or releasing the bacteria from a surface to which they adhere.

30. Composition according to any of the preceding composition paragraphs, wherein the composition is a bar, a homogenous tablet, a tablet having two or more layers, a pouch having one or more compartments, a regular or compact powder, a granule, a paste, a gel, or a regular, compact or concentrated liquid.

31. Composition according to any of the preceding composition paragraphs, wherein the composition is a cleaning composition selected from liquid detergent, powder detergent and granule detergent compositions.

32. A method for laundering an item comprising the steps of:
 a. Exposing an item to a wash liquor comprising a polypeptide of paragraphs 46-56 or a composition according to any of paragraphs 11-31;
 b. Completing at least one wash cycle; and
 c. Optionally rinsing the item,
 wherein the item is a textile.

33. A method for deep cleaning of an item, wherein the item is preferably a textile, said method comprising; exposing an item to a wash liquor comprising a polypeptide, preferably comprising one or more of the motif(s) GXDE (SEQ ID NO 18), [EQ][NRSHA][YVFL][AGSTC][IVLF][EAQYN][SN] (SEQ ID NO 19), [VIM][LIV]G[GAV]DE[VI][PSA] (SEQ ID NO: 20), WND[SQR][IVL][TLVM] (SEQ ID NO: 21), QSTL (SEQ ID NO 22), NKFFY (SEQ ID NO: 23) or NLD[DR]S (SEQ ID NO: 24), wherein the polypeptide is selected from the group consisting of polypeptides having at least 60% e.g. 80%, 85%, 90%, 95%, 98%, 99% or 100% sequence identity to the polypeptide shown in SEQ ID NO 7, SEQ ID NO 8, SEQ ID NO 9, SEQ ID NO 10 and SEQ ID NO 11.

34. Method according to paragraph 32 or 33, wherein the pH of the wash liquor is in the range of 1 to 11.

35. Method according to any of the preceding method paragraphs, wherein the pH of the wash liquor is in the range 5.5 to 11, such as in the range of 7 to 9, in the range of 7 to 8 or in the range of 7 to 8.5.

36. Method according to any of the preceding method paragraphs, wherein the temperature of the wash liquor is in the range of 5° C. to 95° C., or in the range of 10° C. to 80° C., in the range of 10° C. to 70° C., in the range of 10° C. to 60° C., in the range of 10° C. to 50° C., in the range of 15° C. to 40° C., in the range of 20° C. to 40° C., in the range of 15° C. to 30° C. or in the range of 20° C. to 30° C.

37. Method according to any of the preceding method paragraphs, wherein the temperature of the wash liquor is from about 20° C. to about 40° C.

38. Method according to any of the preceding method paragraphs, wherein the temperature of the wash liquor is from about 15° C. to about 30° C.

39. Method according to any of the preceding method paragraphs, wherein stains present on the item is pre-treated with a polypeptide of paragraphs 46-60 or a detergent composition according to any of paragraphs 11-31.

40. Method according to any of the preceding method paragraphs, wherein stickiness of the item is reduced.

41. Method according to any of the preceding method paragraphs, wherein redeposition of soil is reduced.

42. Method according to any of the preceding method paragraphs, wherein adherence of soil to the item is reduced or removed.

43. Method according to any of the preceding method paragraphs, wherein whiteness of the item is maintained or improved.

44. Method according to any of the preceding method paragraphs, wherein malodor is reduced or removed from the item.

45. Method according to any of the preceding method paragraphs, wherein the concentration of the polypeptide having hexosaminidase activity in the wash liquor is at least 0.001 mg of polypeptide, such as at least 0.05 mg of protein, or at least 1.0 mg of protein, or at least 1.5 mg of protein per liter of wash liquor, optionally the concentration of polypeptide in the wash liquor is in the range 0.0002 mg/L to 2 mg/L, such as 0.002 mg/L to 2 mg/L, such as 0.2 mg/L to 2 mg/L or in the range of 0.00001 mg/L to 10 mg/L or in the range of in the range of 0.0001 mg/L to 10 mg/L, or in the range of 0.001 mg/L to 10 mg/L, or in in the range of 0.01 mg/L to 10 mg/L per liter of wash liquor, optionally the concentration of the polypeptide of the invention is 0.00001% to 2 wt %, such as 0.0001 to 0.1 wt %, such as 0.0005 to 0.1 wt %, such as 0.001 to 0.1 wt %, such as 0.001 to 0.5 wt %, such as 0.002 to 0.5 wt % or 0.0002 to 0.09 wt % in the total detergent concentration.

46. A polypeptide having hexosaminidase activity, selected from the group consisting of:
   a. a polypeptide having at least 60% e.g. 80%, 85%, 90%, 95%, 98%, 99% or 100% sequence identity to the mature polypeptide shown in SEQ ID NO 7, 8, 9, 10 or 11;
   b. a polypeptide encoded by a polynucleotide that hybridizes under low stringency conditions with
      i. the mature polypeptide coding sequence of SEQ ID NO 1, 3, 5, 12 or 14,
      ii. the cDNA sequence thereof, or
      iii. the full-length complement of (i) or (ii);
   c. a polypeptide encoded by a polynucleotide having at least 60% e.g. 80%, 85%, 90%, 95%, 98%, 99% or 100% sequence identity to the mature polypeptide coding sequence of SEQ ID NO 1, 3, 5, 12 or 14 or the cDNA sequence thereof;
   d. a variant of the mature polypeptide of SEQ ID NO 7, SEQ ID NO 8, SEQ ID NO 9, SEQ ID NO 10 or SEQ ID NO 11 comprising a substitution, deletion, and/or insertion at one or more positions; and
   e. a fragment of the polypeptide of (a), (b), (c), or (d) that has hexosaminidase activity; and
   f. a polypeptide comprising one or more of the motif(s) GXDE (SEQ ID NO 18), [EQ][NRSHA][YVFL][AG-STC][IVLF][EAQYN][SN] (SEQ ID NO 19), [VIM][LIV]G[GAV]DE[VI][PSA] (SEQ ID NO: 20), WND[SQR][IVL][TLVM] (SEQ ID NO: 21), QSTL (SEQ ID NO 22), NKFFY (SEQ ID NO: 23), NLD[DR]S (SEQ ID NO: 24).

47. The polypeptide of paragraph 46, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO 2, SEQ ID NO 4, SEQ ID NO 6, SEQ ID NO 13 or SEQ ID NO 15, or to the polypeptide shown in SEQ ID NO 7, SEQ ID NO 8, SEQ ID NO 9, SEQ ID NO 10 or SEQ ID NO 11.

48. The polypeptide of paragraph 46 or 47, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO 2 or to the mature polypeptide shown in SEQ ID NO 7.

49. The polypeptide of paragraph 46 or 47, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO 4 or to the mature polypeptide shown in SEQ ID NO 8.

50. The polypeptide of paragraph 46 or 47, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO 6 or to the mature polypeptide shown in SEQ ID NO 9.

51. The polypeptide of paragraph 46 or 47, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO 13 or to the mature polypeptide shown in SEQ ID NO 10.

52. The polypeptide of paragraph 46 or 47, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO 15 or to the mature polypeptide shown in SEQ ID NO 11
53. The polypeptide according to paragraph 46 to 52, which is encoded by a polynucleotide that hybridizes under low stringency conditions, low-medium stringency conditions, medium stringency conditions, medium-high stringency conditions, high stringency conditions, or very high stringency conditions with
   i. the mature polypeptide coding sequence of SEQ ID NO 1, 3, 5, 12 or 14,
   ii. the cDNA sequence thereof, or
   iii. the full-length complement of (i) or (ii).
54. The polypeptide according to any of paragraphs 46-53, which is encoded by a polynucleotide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide coding sequence of SEQ ID NO 1, 3, 5, 12, 14 or the cDNA sequence thereof.
55. The polypeptide according to any of paragraphs 46 to 54, comprising or consisting of the amino acids sequence shown in SEQ ID NO 7, SEQ ID NO 8, SEQ ID NO 9, SEQ ID NO 10 or SEQ ID NO 11 or the mature polypeptide of SEQ ID NO 2, SEQ ID NO 4, SEQ ID NO 6, SEQ ID NO 13 or SEQ ID NO 15.
56. The polypeptide according to any of paragraphs 46 to 55, which is a variant of SEQ ID NO 7, SEQ ID NO 8, SEQ ID NO 9, SEQ ID NO 10 or SEQ ID NO 11 comprising a substitution, deletion, and/or insertion at one or more positions.
57. A polynucleotide encoding the polypeptide according to any of paragraphs 46-56.
58. A nucleic acid construct or expression vector comprising the polynucleotide of paragraph 57 operably linked to one or more control sequences that direct the production of the polypeptide in an expression host.
59. A recombinant host cell comprising the polynucleotide of paragraph 57 operably linked to one or more control sequences that direct the production of the polypeptide.
60. A method of producing the polypeptide of any of paragraphs 46-56, comprising cultivating a cell, which in its wild-type form produces the polypeptide, under conditions conducive for production of the polypeptide.
61. The method of paragraph 60, further comprising recovering the polypeptide.
62. A method of producing a polypeptide according to any of paragraphs 46-56, comprising cultivating the host cell of paragraph 59 under conditions conducive for production of the polypeptide.
63. The method of paragraph 62, further comprising recovering the polypeptide.
64. A nucleic acid construct or expression vector comprising a gene encoding a protein operably linked to the polynucleotide of paragraph 57, wherein the gene is foreign to the polynucleotide encoding the signal peptide.
65. A recombinant host cell comprising a gene encoding a protein operably linked to the polynucleotide of paragraph 57, wherein the gene is foreign to the polynucleotide encoding the signal peptide.
66. A method of producing a protein, comprising cultivating a recombinant host cell comprising a gene encoding a protein operably linked to the polynucleotide of paragraph 62, wherein the gene is foreign to the polynucleotide encoding the signal peptide, under conditions conducive for production of the protein.
67. The method of paragraph 66, further comprising recovering the protein.
68. The recombinant host cell of paragraph 65 further comprising a polynucleotide encoding a second polypeptide of interest; preferably an enzyme of interest; more preferably a secreted enzyme of interest; even more preferably a hydrolase, isomerase, ligase, lyase, oxidoreductase, or a transferase; and most preferably the secreted enzyme is an alpha-galactosidase, alpha-glucosidase, aminopeptidase, amylase, asparaginase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, green fluorescent protein, glucano-transferase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or a xylanase.
69. The recombinant host cell of paragraph 65, wherein the second polypeptide of interest is heterologous or homologous to the host cell.
70. The recombinant host cell of paragraph 65 or 68, which is a fungal host cell; preferably a filamentous fungal host cell; more preferably an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phiebia, Piromyces, Pleurotus, Schizophyllum, Talaromyces, Thermoascus, Thielavia, Tolypocladium, Trametes,* or *Trichoderma* cell; most preferably an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phiebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.
71. The recombinant host cell of paragraph 65 or 68, which is a bacterial host cell; preferably a prokaryotic host cell; more preferably a Gram-positive host cell; even more preferably a *Bacillus, Clostridium, Enterococcus, Geobacillus, Lactobacillus, Lactococcus, Oceanobacillus, Staphylococcus, Streptococcus,* or *Streptomyces* host cell; and most preferably a *Bacillus alkalophilus, Bacillus*

*amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* and *Bacillus thuringiensis* host cell.

72. Item laundered according to the method of any of paragraphs 32-45.

Some preferred embodiments are summarized in the following paragraphs:

1. A composition comprising at least 0.01 mg of active enzyme per gram of composition, wherein the polypeptide having hexosaminidase activity is selected from the group consisting of a polypeptide having at least 60% sequence identity to the mature polypeptide of SEQ ID NO: 2, 4 and 6 and at least one adjunct ingredient.
2. The composition of paragraph 1, wherein the polypeptide has at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO: 2, 4 and 6.
3. The composition of any of paragraphs 1 or 2, comprising or consisting of SEQ ID NO: 7 or the mature polypeptide of SEQ ID NO: 2, SEQ ID NO: 8 or the mature polypeptide of SEQ ID NO: 4 or SEQ ID NO: 9 or the mature polypeptide of SEQ ID NO: 6.
4. The composition according to any of paragraphs 1 to 3 wherein the composition is a cleaning composition such as a laundry or dish wash composition
5. The composition according to paragraph 4, wherein the adjunct ingredient is selected from,
   a. at least one builder,
   b. at least one surfactant, and
   c. at least one bleach component.
6. The composition according to paragraph 5, wherein the composition comprises at least one builder, wherein the builder is added in an amount of about 0-65% by weight, preferably about 40-65% by weight, particularly about 20-65% by weight, particularly from 10% to 50% by weight and wherein the builder is selected among phosphates, sodium citrate builders, sodium carbonate, sodium silicate, sodium and zeolites.
7. The composition according to paragraph 6 wherein the builder is selected from citric acid, methyl glycine-N, N-diacetic acid (MGDA) and/or glutamic-N,N-diacetic acid (GLDA) and mixtures thereof.
8. The composition according to any of the preceding paragraphs comprising 1-40 wt %, preferably from 0.5-30 wt %, of at least one bleaching component, wherein the bleach component includes a percarbonate and bleach catalyst, preferably a manganese compound.
9. The composition according to paragraph 8 wherein at least one bleach component is a peroxide, preferably percabonate and a catalyst preferably a metal-containing bleach catalyst such as 1,4,7-trimethyl-1,4,7-triazacyclononane or manganese (II) acetate tetrahydrate (MnTACN).
10. The composition according to any of the previous paragraphs, wherein the composition comprise at least one surfactant wherein the surfactant is anionic and/or nonionic.
11. The composition according to paragraph 10, wherein the composition comprises from about 5 wt % to about 50 wt %, from about 5 wt % to about 40 wt %, from about 5 wt % to about 30 wt %, from about 5 wt % to about 20 wt %, from about 5 wt % to about 10 wt % anionic surfactant.
12. The composition according to any of paragraphs 10 or 11, wherein the composition comprises from about 5 wt % to about 50 wt %, from about 5 wt % to about 40 wt %, from about 5 wt % to about 30 wt %, from about 5 wt % to about 20 wt %, from about 5 wt % to about 10 wt % nonionic surfactant.
13. The composition according to any of paragraphs 10 to 12, wherein the anionic surfactant is selected from linear alkylbenzenesulfonates (LAS) isomers of LAS, alcohol ether sulfate (AEO, AEOS) and sodium lauryl ether sulfate and sodium laureth sulfate (SLES).
14. The composition according to any of paragraphs 10 to 13, wherein the nonionic surfactant is selected from alcohol ethoxylates (AE or AEO), alcohol propoxylates, alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxyalkyl fatty acid amides, N-acyl N-alkyl derivatives of glucosamine (glucamides, GA, or fatty acid glucamides, FAGA) and combinations thereof.
15. Use of a composition of any of paragraphs 1 to 14 for deep-cleaning of an item, wherein the item is a textile.
16. A laundering method for laundering an item comprising the steps of:
    Exposing an item to a wash liquor comprising a polypeptide selected from the group consisting of a polypeptide having at least 60% sequence identity to the mature polypeptide of SEQ ID NO: 2, 4 and 6 or a detergent composition according to any of paragraphs 1 to 14;
    Completing at least one wash cycle; and
    Optionally rinsing the item,
    wherein the item is a textile.
17. Use of a polypeptide of the *Terribacillus* clade, wherein the polypeptide has hexosaminidase activity in a cleaning process, such as laundry and/or dish wash.
18. Use of a polypeptide of the *Terribacillus* clade, wherein the polypeptide has hexosaminidase activity for deep cleaning of an item, wherein the item is a textile.
19. Use according to paragraph 17 for preventing, reducing or removing stickiness of the item.
20. Use according to any of paragraphs 17 or 18 for preventing, reducing or removing redeposition of soil during a wash cycle.
21. Use according to any of the preceding paragraphs, wherein the polypeptide is selected from the group consisting of a polypeptide having at least 60% sequence identity to the mature polypeptide of SEQ ID NO: 2, 4 and 6 and at least one adjunct ingredient.
22. The use of paragraph 21, wherein the polypeptide has at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO: 2, 4 and 6.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Assays and Detergent Compositions

Detergent Compositions

The below mentioned detergent composition may be used in combination with the enzyme of the invention.

Biotex Black (Liquid)

5-15% Anionic surfactants, <5% Nonionic surfactants, perfume, enzymes, DMDM and hydantoin.

Composition of Ariel Sensitive White & Color, Liquid Detergent Composition

Aqua, Alcohol Ethoxy Sulfate, Alcohol Ethoxylate, Amino Oxide, Citric Acid, C12-18 topped palm kernel fatty acid, Protease, Glycosidase, Amylase, Ethanol, 1,2 Propanediol, Sodium Formate, Calcium Chloride, Sodium hydroxide, Silicone Emulsion, Trans-sulphated EHDQ (the ingredients are listed in descending order).

Composition of WFK IEC-A Model Detergent (Powder)

Ingredients: Linear sodium alkyl benzene sulfonate 8.8%, Ethoxylated fatty alcohol C12-18 (7 EO) 43.7%, Sodium soap 3.2%, Anti foam DC2-42485 3.9%, Sodium aluminium silicate zeolite 4A 28.3%, Sodium carbonate 11.6%, Sodium salt of a copolymer from acrylic and maleic acid (Sokalan CP5) 2.4%, Sodium silicate 3.0%, Carboxymethylcellulose 1.2%, Dequest 2066 2.8%, Optical whitener 0.2%, Sodium sulfate 6.5%, Protease 0.4%.

Composition of Model Detergent A (Liquid)

Ingredients: 12% LAS, 11% AEO Biosoft N25-7 (NI), 5% AEOS (SLES), 6% MPG (monopropylene glycol), 3% ethanol, 3% TEA, 2.75% coco soap, 2.75% soya soap, 2% glycerol, 2% sodium hydroxide, 2% sodium citrate, 1% sodium formate, 0.2% DTMPA and 0.2% PCA (all percentages are w/w)

Composition of Model Detergent N (Liquid)

Ingredients: NaOH 0.87%, MPG (Monopropylenglycol) 6%, Glycerol 2%, Soap 2.75%, Soap-soy 2.75%, Soap-coco 2.75%, PCA (Sokalon CP-5) 0.2%, AEO Biosoft N25-7(NI) 16%, Sodium formate 1%, Sodium Citrate 2%, DTMPA 0.2%, Ethanol (96%) 3%, adjustment of pH with NaOH or Citric acid as water to 100% (all percentages are w/w (weight volume).

Composition of Persil Universal Gel

Ingredients: 15-30% Anionic surfactants, 5-15% Non-ionic surfactant, <5% Phosphonate, soap, Amyl cinnamal, Butylphenyl methylpropional, limonene, Gernaiol, Optical brightener, enzymes.

Composition of Ariel Actilift (Liquid)

Ingredients: 5-15% Anionic surfactants; <5% Non-ionic surfactants, Phosphonates, Soap; Enzymes, Optical brighteners, Benzisothiazolinone, Methylisothiazolinone, Perfumes, Alpha-isomethyl ionone, Citronellol, Geraniol, Linalool.

Composition of Ariel Actilift Colour&Style (liquid)

Ingredients: 5-15% Anionic surfactants; <5% Non-ionic surfactants, Phosphonates, Soap; Enzymes, Perfumes, Benzisothiazolinone, Methylisothiazolinone, Alpha-isomethyl ionone, Butylphenyl methylpropional, Citronellol, Geraniol, Linalool.

Composition of Persil Small & Mighty (liquid)

Ingredients: 15-30% Anionic surfactants, Non-ionic surfactants, 5-15% Soap, <5% Polycarboxylates, Perfume, Phosphates, Optical Brighteners Persil 2 in 1 with Comfort Passion Flower Powder Sodium sulfate, Sodium carbonate, Sodium Dodecylbenzenesulfonate, Bentonite, Sodium Carbonate Peroxide, Sodium Silicate, Zeolite, Aqua, Citric acid, TAED, C12-15 Pareth-7, Stearic Acid, Parfum, Sodium Acrylic Acid/MA Copolymer, Cellulose Gum, Corn Starch Modified, Sodium chloride, Tetrasodium Etidronate, Calcium Sodium EDTMP, Disodium Anilinomorpholinotriazinyl-aminostilbenesulfonate, Sodium bicarbonate, Phenylpropyl Ethyl Methicone, Butylphenyl Methylpropional, Glyceryl Stearates, Calcium carbonate, Sodium Polyacrylate, Alpha-Isomethyl Ionone, Disodium Distyrylbiphenyl Disulfonate, Cellulose, Protease, Limonene, PEG-75, Titanium dioxide, Dextrin, Sucrose, Sodium Polyaryl Sulphonate, CI 12490, CI 45100, CI 42090, Sodium Thiosulfate, CI 61585.

Persil Biological Powder

Sucrose, Sorbitol, Aluminum Silicate, Polyoxymethylene Melamine, Sodium Polyaryl Sulphonate, CI 61585, CI 45100, Lipase, Amylase, Xanthan gum, Hydroxypropyl methyl cellulose, CI 12490, Disodium Distyrylbiphenyl Disulfonate, Sodium Thiosulfate, CI 42090, Mannanase, CI 11680, Etidronic Acid, Tetrasodium EDTA.

Persil Biological Tablets

Sodium carbonate, Sodium Carbonate Peroxide, Sodium bicarbonate, Zeolite, Aqua, Sodium Silicate, Sodium Lauryl Sulfate, Cellulose, TAED, Sodium Dodecylbenzenesulfonate, Hemicellulose, Lignin, Lauryl Glucoside, Sodium Acrylic Acid/MA Copolymer, Bentonite, Sodium chloride, Parfum, Tetrasodium Etidronate, Sodium sulfate, Sodium Polyacrylate, Dimethicone, Disodium Anilinomorpholino-triazinylaminostilbenesulfonate, Dodecylbenzene Sulfonic Acid, Trimethylsiloxysilicate, Calcium carbonate, Cellulose, PEG-75, Titanium dioxide, Dextrin, Protease, Corn Starch Modified, Sucrose, CI 12490, Sodium Polyaryl Sulphonate, Sodium Thiosulfate, Amylase, Kaolin, Persil Colour Care Biological Powder Subtilisin, Imidazolidinone, Hexyl Cinnamal, Sucrose, Sorbitol, Aluminum Silicate, Polyoxymethylene Melamine, CI 61585, CI 45100, Lipase, Amylase, Xanthan gum, Hydroxypropyl methyl cellulose, CI 12490, Disodium Distyrylbiphenyl Disulfonate, Sodium Thiosulfate, CI 42090, Mannanase, CI 11680, Etidronic Acid, Tetrasodium EDTA.

Persil Colour Care Biological Tablets

Sodium bicarbonate, Sodium carbonate, Zeolite, Aqua, Sodium Silicate, Sodium Lauryl Sulfate, Cellulose Gum, Sodium Dodecylbenzenesulfonate, Lauryl Glucoside, Sodium chloride, Sodium Acrylic Acid/MA Copolymer, Parfum, Sodium Thioglycolate, PVP, Sodium sulfate, Tetrasodium Etidronate, Sodium Polyacrylate, Dimethicone, Bentonite, Dodecylbenzene Sulfonic Acid, Trimethylsiloxysilicate, Calcium carbonate, Cellulose, PEG-75, Titanium dioxide, Dextrin, Protease, Corn Starch Modified, Sucrose, Sodium Thiosulfate, Amylase, CI 74160, Kaolin.

Persil Dual Action Capsules Bio

MEA-Dodecylbenzenesulfonate, MEA-Hydrogenated Cocoate, C12-15 Pareth-7, Dipropylene Glycol, Aqua, Tetrasodium Etidronate, Polyvinyl Alcohol, Glycerin, Aziridine, homopolymer ethoxylated, Propylene glycol, Parfum, Sodium Diethylenetriamine Pentamethylene Phosphonate, Sorbitol, MEA-Sulfate, Ethanolamine, Subtilisin, Glycol, Butylphenyl Methylpropional, Boronic acid, (4-formylphenyl), Hexyl Cinnamal, Limonene, Linalool, Disodium Distyrylbiphenyl Disulfonate, Alpha-Isomethyl Ionone, Geraniol, Amylase, Polymeric Blue Colourant, Polymeric Yellow Colourant, Talc, Sodium chloride, Benzisothiazolinone, Mannanase, Denatonium Benzoate.

Persil 2 in 1 with Comfort Sunshiny Days Powder

Sodium sulfate, Sodium carbonate, Sodium Dodecylbenzenesulfonate, Bentonite, Sodium Carbonate Peroxide, Sodium Silicate, Zeolite, Aqua, Citric acid, TAED, C12-15 Pareth-7, Parfum, Stearic Acid, Sodium Acrylic Acid/MA Copolymer, Cellulose Gum, Corn Starch Modified, Sodium chloride, Tetrasodium Etidronate, Calcium Sodium EDTMP, Disodium Anilinomorpholinotriazinyl-aminostilbenesulfonate, Sodium bicarbonate, Phenylpropyl Ethyl Methicone, Butylphenyl Methylpropional, Glyceryl Stearates, Calcium carbonate, Sodium Polyacrylate, Geraniol, Disodium Distyrylbiphenyl Disulfonate, Cellulose, Protease, PEG-75, Titanium dioxide, Dextrin, Sucrose, Sodium Polyaryl Sulphonate, CI 12490, CI 45100, CI 42090, Sodium Thiosulfate, CI 61585.

Persil Small & Mighty 2in1 with Comfort Sunshiny Days

Aqua, C12-15 Pareth-7, Sodium Dodecylbenzenesulfonate, Propylene glycol, Sodium Hydrogenated Cocoate, Triethanolamine, Glycerin, TEA-Hydrogenated Cocoate, Parfum, Sodium chloride, Polyquaternium-10, PVP, Polymeric Pink Colourant, Sodium sulfate, Disodium Distyrylbiphenyl Disulfonate, Butylphenyl Methylpropional, Styrene/Acrylates Copolymer, Hexyl Cinnamal, Citronellol, Eugenol, Polyvinyl Alcohol, Sodium acetate, Isopropyl alcohol, Polymeric Yellow Colourant, Sodium Lauryl Sulfate.

Persil Small & Mighty Bio

Aqua, MEA-Dodecylbenzenesulfonate, Propylene glycol, Sodium Laureth Sulfate, C12-15 Pareth-7, TEA-Hydrogenated Cocoate, MEA-Citrate, Aziridine homopolymer ethoxylated, MEA-Etidronate, Triethanolamine, Parfum, Acrylates Copolymer, Sorbitol, MEA-Sulfate, Sodium Sulfite, Disodium Distyrylbiphenyl Disulfonate, Butylphenyl Methylpropional, Styrene/Acrylates Copolymer, Citronellol, Sodium sulfate, Peptides, salts, sugars from fermentation (process), Subtilisin, Glycerin, Boronic acid, (4-formylphenyl), Geraniol, Pectate Lyase, Amylase, Sodium Lauryl Sulfate, Mannanase, CI 42051.

Persil Small & Mighty Capsules Biological

MEA-Dodecylbenzenesulfonate, MEA-Hydrogenated Cocoate, C12-15 Pareth-7, Dipropylene Glycol, Aqua, Glycerin, Polyvinyl Alcohol, Parfum, Aziridine homopolymer ethoxylated, Sodium Diethylenetriamine Pentamethylene Phosphonate, Propylene glycol, Sorbitol, MEA-Sulfate, Ethanolamine, Subtilisin, Glycol, Butylphenyl Methylpropional, Hexyl Cinnamal, Starch, Boronic acid, (4-formylphenyl), Limonene, Linalool, Disodium Distyrylbiphenyl Disulfonate, Alpha-Isomethyl Ionone, Geraniol, Amylase, Talc, Polymeric Blue Colourant, Sodium chloride, Benzisothiazolinone, Denatonium Benzoate, Polymeric Yellow Colourant, Mannanase.

Persil Small & Mighty Capsules Colour Care

MEA-Dodecylbenzenesulfonate, MEA-Hydrogenated Cocoate, C12-15 Pareth-7, Dipropylene Glycol, Aqua, Glycerin, Polyvinyl Alcohol, Parfum, Aziridine homopolymer ethoxylated, Sodium Diethylenetriamine Pentamethylene Phosphonate, Propylene glycol, MEA-Sulfate, Ethanolamine, PVP, Sorbitol, Butylphenyl Methylpropional, Subtilisin, Hexyl Cinnamal, Starch, Limonene, Linalool, Boronic acid, (4-formylphenyl), Alpha-Isomethyl Ionone, Geraniol, Talc, Polymeric Blue Colourant, Denatonium Benzoate, Polymeric Yellow Colourant.

Persil Small & Mighty Colour Care

Aqua, MEA-Dodecylbenzenesulfonate, Propylene glycol, Sodium Laureth Sulfate, C12-15 Pareth-7, TEA-Hydrogenated Cocoate, MEA-Citrate, Aziridine homopolymer ethoxylated, MEA-Etidronate, Triethanolamine, Parfum, Acrylates Copolymer, Sorbitol, MEA-Sulfate, Sodium Sulfite, Glycerin, Butylphenyl Methylpropional, Citronellol, Sodium sulfate, Peptides, salts, sugars from fermentation (process), Styrene/Acrylates Copolymer, Subtilisin, Boronic acid, (4-formylphenyl), Geraniol, Pectate Lyase, Amylase, Sodium Lauryl Sulfate, Mannanase, CI 61585, CI 45100.

Composition of Fairy Non Bio (Liquid)

Ingredients: 15-30% Anionic Surfactants, 5-15% Non-Ionic Surfactants, Soap, Benzisothiazolinone, Methylisothiazolinone, Perfumes Composition of Model Detergent T (Powder)

Ingredients: 11% LAS, 2% AS/AEOS, 2% soap, 3% AEO, 15.15% sodium carbonate, 3% sodium silcate, 18.75% zeolite, 0.15% chelant, 2% sodium citrate, 1.65% AA/MA copolymer, 2.5% CMC and 0.5% SRP (all percentages are w/w).

Composition of Model Detergent X (Powder)

Ingredients: 16.5% LAS, 15% zeolite, 12% sodium disilicate, 20% sodium carbonate, 1% sokalan, 35.5% sodium sulfate (all percentages are w/w).

Composition of Ariel Actilift Colour&Style (Powder)

Ingredients: 15-30% Anionic surfactants, <5% Non-ionic surfactants, Phosphonates, Polycarboxylates, Zeolites; Enzymes, Perfumes, Hexyl cinnamal.

Composition of Ariel Actilift (Powder)

Ingredients: 5-15% Anionic surfactants, Oxygen-based bleaching agents, <5% Non-ionic surfactants, Phosphonates, Polycarboxylates, Zeolites, Optical brighteners, Enzymes, Perfumes, Butylphenyl Methylpropional, Coumarin, Hexyl Cinnamal Composition of Persil Megaperls (Powder)

Ingredients: 15-30% of the following: anionic surfactants, oxygen-based bleaching agent and zeolites, less than 5% of the following: non-ionic surfactants, phosphonates, polycarboxylates, soap, Further ingredients: Perfumes, Hexyl cinnamal, Benzyl salicylate, Linalool, optical brighteners, Enzymes and Citronellol.

Gain Liquid, Original:

Ingredients: Water, Alcohol Ethoxysulfate, Diethylene Glycol, Alcohol Ethoxylate, Ethanolamine, Linear Alkyl Benzene Sulfonate, Sodium Fatty Acids, Polyethyleneimine Ethoxylate, Citric Acid, Borax, Sodium Cumene Sulfonate, Propylene Glycol, DTPA, Disodium Diaminostilbene Disulfonate, Dipropylethyl Tetramine, Sodium Hydroxide, Sodium Formate, Calcium Formate, Dimethicone, Amylase, Protease, Liquitint™, Hydrogenated Castor Oil, Fragrance.

Tide Liquid, Original:

Ingredients: Linear alkylbenzene sulfonate, propylene glycol, citric acid, sodium hydroxide, borax, ethanolamine, ethanol, alcohol sulfate, polyethyleneimine ethoxylate, sodium fatty acids, diquaternium ethoxysulfate, protease, diethylene glycol, laureth-9, alkyldimethylamine oxide, fragrance, amylase, disodium diaminostilbene disulfonate, DTPA, sodium formate, calcium formate, polyethylene glycol 4000, mannanase, Liquitint™ Blue, dimethicone.

Liquid Tide, Free and Gentle:

Water, sodium alcoholethoxy sulfate, propylene glycol, borax, ethanol, linear alkylbenzene sulfonate sodium, salt, polyethyleneimine ethoxylate, diethylene glycol, trans sulphated & ethoxylated hexamethylene diamine, alcohol ethoxylate, linear alkylbenzene sulfonate, MEA salt, sodium formate, sodium alkyl sulfate, DTPA, amine oxide, calcium formate, disodium diaminostilbene, disulfonate, amylase, protease, dimethicone, benzisothiazolinone Tide Coldwater Liquid, Fresh Scent:

Water, alcoholethoxy sulfate, linear alkylbenzene sulfonate, diethylene glycol, propylene glycol, ethanolamine, citric acid, Borax, alcohol sulfate, sodium hydroxide, polyethyleneimine, ethoxylate, sodium fatty acids, ethanol, protease, Laureth-9, diquaternium ethoxysulfate, lauramine oxide, sodium cumene, sulfonate, fragrance, DTPA, amylase, disodium, diaminostilbene, disulfonate, sodium formate, disodium distyrylbiphenyl disulfonate, calcium formate, polyethylene glycol 4000, mannanase, pectinase, Liquitint™ Blue, dimethicone Tide TOTALCARE™ Liquid, Cool Cotton:

Water, alcoholethoxy sulfate, propylene glycol, sodium fatty acids, laurtrimonium chloride, ethanol, sodium hydroxide, sodium cumene sulfonate, citric acid, ethanolamine, diethylene glycol, silicone polyether, borax, fragrance, polyethyleneimine ethoxylate, protease, Laureth-9, DTPA, polyacrylamide quaternium chloride, disodium diaminostilbene disulfonate, sodium formate, Liquitint™ Orange, dipropylethyl tetraamine, dimethicone, cellulase, Liquid Tide Plus Bleach Alternative™, Vivid White and Bright, Original and Clean Breeze Water, sodium alcoholethoxy sulfate, sodium alkyl sulfate, MEA citrate, linear alkylbenzene sulfonate, MEA salt, propylene glycol, diethylene glycol, polyethyleneimine ethoxylate, ethanol, sodium fatty acids, ethanolamine, lauramine oxide, borax, Laureth-9, DTPA, sodium cumene sulfonate, sodium formate, calcium formate, linear alkylbenzene sulfonate, sodium salt, alcohol sulfate, sodium hydroxide, diquaternium ethoxysulfate, fragrance, amylase, protease, mannanase, pectinase, disodium diaminostilbene disulfonate, benzisothiazolinone, Liquitint™ Blue, dimethicone, dipropylethyl tetraamine.

Liquid Tide HE, Original Scent:

Water, Sodium alcoholethoxy sulfate, MEA citrate, Sodium Alkyl Sulfate, alcohol ethoxylate, linear alkylbenzene sulfonate, MEA salt, sodium fatty acids, polyethyleneimine ethoxylate, diethylene glycol, propylene glycol, diquaternium ethoxysulfate, borax, polyethyleneimine, ethoxylate propoxylate, ethanol, sodium cumene sulfonate, fragrance, DTPA, disodium diaminostilbene disulfonate, Mannanase, cellulase, amylase, sodium formate, calcium formate, Lauramine oxide, Liquitint™ Blue, Dimethicone/polydimethyl silicone.

Tide TOTALCARE HE Liquid, Renewing Rain:

Water, alcoholethoxy sulfate, linear alkylbenzene sulfonate, alcohol ethoxylate, citric acid, Ethanolamine, sodium fatty acids, diethylene glycol, propylene glycol, sodium hydroxide, borax, polyethyleneimine ethoxylate, silicone polyether, ethanol, protease, sodium cumene sulfonate, diquaternium ethoxysulfate, Laureth-9, fragrance, amylase, DTPA, disodium diaminostilbene disulfonate, disodium distyrylbiphenyl disulfonate, sodium formate, calcium formate, mannanase, Liquitint™ Orange, dimethicone, polyacrylamide quaternium chloride, cellulase, dipropylethyl tetraamine.

Tide Liquid HE Free:

Water, alcoholethoxy sulfate, diethylene glycol, monoethanolamine citrate, sodium formate, propylene glycol, linear alkylbenzene sulfonates, ethanolamine, ethanol, polyethyleneimine ethoxylate, amylase, benzisothiazolin, borax, calcium formate, citric acid, diethylenetriamine pentaacetate sodium, dimethicone, diquaternium ethoxysulfate, disodium diaminostilbene disulfonate, Laureth-9, mannanase, protease, sodium cumene sulfonate, sodium fatty acids.

Tide Coldwater HE Liquid, Fresh Scent:

Water, alcoholethoxy sulfate, MEA Citrate, alcohol sulfate, Alcohol ethoxylate, Linear alkylbenzene sulfonate MEA, sodium fatty acids, polyethyleneimine ethoxylate, diethylene glycol, propylene glycol, diquaternium ethoxysulfate, borax, polyethyleneimine ethoxylate propoxylate, ethanol, sodium cumene sulfonate, fragrance, DTPA, disodium diaminostilbene disulfonate, protease, mannanase, cellulase, amylase, sodium formate, calcium formate, lauramine oxide, Liquitint™ Blue, dimethicone.

Tide for Coldwater HE Free Liquid:

Water, sodium alcoholethoxy sulfate, MEA Citrate, Linear alkylbenzene sulfonate: sodium salt, Alcohol ethoxylate, Linear alkylbenzene sulfonate: MEA salt, sodium fatty acids, polyethyleneimine ethoxylate, diethylene glycol, propylene glycol, diquaternium ethoxysulfate, Borax, protease, polyethyleneimine ethoxylate propoxylate, ethanol, sodium cumene sulfonate, Amylase, citric acid, DTPA, disodium diaminostilbene disulfonate, sodium formate, calcium formate, dimethicone.

Tide Simply Clean & Fresh:

Water, alcohol ethoxylate sulfate, linear alkylbenzene sulfonate Sodium/Mea salts, propylene glycol, diethylene glycol, sodium formate, ethanol, borax, sodium fatty acids, fragrance, lauramine oxide, DTPA, Polyethylene amine ethoxylate, calcium formate, disodium diaminostilbene disulfonate, dimethicone, tetramine, Liquitint™ Blue.

Tide Pods, Ocean Mist, Mystic Forest, Spring Meadow:

Linear alkylbenzene sulfonates, C12-16 Pareth-9, propylene glycol, alcoholethoxy sulfate, water, polyethyleneimine ethoxylate, glycerine, fatty acid salts, PEG-136 polyvinyl acetate, ethylene Diamine disuccinic salt, monoethanolamine citrate, sodium bisulfite, diethylenetriamine pentaacetate sodium, disodium distyrylbiphenyl disulfonate, calcium formate, mannanase, exyloglucanase, sodium formate, hydrogenated castor oil, natalase, dyes, termamyl, Subtilisin, benzisothiazolin, perfume.

Tide to Go:

Deionized water, Dipropylene Glycol Butyl Ether, Sodium Alkyl Sulfate, Hydrogen Peroxide, Ethanol, Magnesium Sulfate, Alkyl Dimethyl Amine Oxide, Citric Acid, Sodium Hydroxide, Trimethoxy Benzoic Acid, Fragrance.

Tide Stain Release Liquid:

Water, Alkyl Ethoxylate, Linear Alkylbenzenesulfonate, Hydrogen Peroxide, Diquaternium Ethoxysulfate, Ethanolamine, Disodium Distyrylbiphenyl Disulfonate, tetrabutyl Ethylidinebisphenol, F&DC Yellow 3, Fragrance.

Tide Stain Release Powder:

Sodium percarbonate, sodium sulfate, sodium carbonate, sodium aluminosilicate, nonanoyloxy benzene sulfonate, sodium polyacrylate, water, sodium alkylbenzenesulfonate, DTPA, polyethylene glycol, sodium palmitate, amylase, protease, modified starch, FD&C Blue 1, fragrance.

Tide Stain Release, Pre-Treater Spray:

Water, Alkyl Ethoxylate, MEA Borate, Linear Alkylbenzenesulfonate, Propylene Glycol, Diquaternium Ethoxysulfate, Calcium Chlorideenzyme, Protease, Ethanolamine, Benzoisothiazolinone, Amylase, Sodium Citrate, Sodium Hydroxide, Fragrance.

Tide to Go Stain Eraser:

Water, Alkyl Amine Oxide, Dipropylene Glycol Phenyl Ether, Hydrogen Peroxide, Citric Acid, Ethylene Diamine Disuccinic Acid Sodium salt, Sodium Alkyl Sulfate, Fragrance.

Tide Boost with Oxi:

Sodium bicarbonate, sodium carbonate, sodium percarbonate, alcohol ethoxylate, sodium chloride, maleic/acrylic copolymer, nonanoyloxy benzene sulfonate, sodium sulfate, colorant, diethylenetriamine pentaacetate sodium salt, hydrated aluminosilicate (zeolite), polyethylene glycol, sodium alkylbenzene sulfonate, sodium palmitate, starch, water, fragrance.

Tide Stain Release Boost Duo Pac:

Polyvinyl Alcoholpouch film, wherein there is packed a liquid part and a powder part:

Liquid Ingredients: Dipropylene Glycol, diquaternium Ethoxysulfate, Water, Glycerin, Liquitint™ Orange, Powder Ingredients: sodium percarbonate, nonanoyloxy benzene sulfonate, sodium carbonate, sodium sulfate, sodium aluminosilicate, sodium polyacrylate, sodium alkylbenzenesulfonate, maleic/acrylic copolymer, water, amylase, polyethylene glycol, sodium palmitate, modified starch, protease, glycerine, DTPA, fragrance.

Tide Ultra Stain Release:

Water, sodium alcoholethoxy sulfate, linear alkyl benzene sulfonate, sodium/MEA salts, MEA citrate, propylene glycol, polyethyleneimine ethoxylate, ethanol, diethylene glycol, polyethyleneimine propoxyethoxylate, sodium fatty acids, protease, borax, sodium cumene sulfonate, DTPA, fragrance, amylase, disodium diaminostilbene disulfonate, calcium formate, sodium formate, gluconase, dimethicone, Liquitint™ Blue, mannanase.

Ultra Tide with a Touch of Downy® Powdered Detergent, April Fresh/Clean Breeze/April Essence:

Sodium Carbonate, Sodium Aluminosilicate, Sodium Sulfate, Linear Alkylbenzene Sulfonate, Bentonite, Water, Sodium Percarbonate, Sodium Polyacrylate, Silicate, Alkyl Sulfate, Nonanoyloxybenzenesulfonate, DTPA, Polyethylene Glycol 4000, Silicone, Ethoxylate, fragrance, Polyethylene Oxide, Palmitic Acid, Disodium Diaminostilbene Disulfonate, Protease, Liquitint™ Red, FD&C Blue 1, Cellulase.

Ultra Tide with a Touch of Downy Clean Breeze:

Water, sodium alcoholethoxy sulfate, MEA citrate, linear alkyl benzene sulfonate: sodium/MEA salts, propylene glycol, polyethyleneimine ethoxylate, ethanol, diethylene glycol, polyethyleneimine, propoxyethoxylate, diquaternium ethoxysulfate, alcohol sulfate, dimethicone, fragrance, borax, sodium fatty acids, DTPA, protease, sodium bisulfite, disodium diaminostilbene disulfonate, amylase, gluconase, castor oil, calcium formate, MEA, styrene acrylate copolymer, sodium formate, Liquitint™ Blue.

Ultra Tide with Downy Sun Blossom:

Water, sodium alcoholethoxy sulfate, MEA citrate, linear alkyl benzene sulfonate: sodium/MEA salts, propylene glycol, ethanol, diethylene glycol, polyethyleneimine propoxyethoxylate, polyethyleneimine ethoxylate, alcohol sulfate, dimethicone, fragrance, borax, sodium fatty acids, DTPA, protease, sodium bisulfite, disodium diaminostilbene disulfonate, amylase, castor oil, calcium formate, MEA, styrene acrylate copolymer, propanaminium propanamide, gluconase, sodium formate, Liquitint™ Blue.

Ultra Tide with Downy April Fresh/Sweet Dreams:

Water, sodium alcoholethoxy sulfate, MEA citrate, linear alkyl benzene sulfonate: sodium/MEA salts, propylene glycol, polyethyleneimine ethoxylate, ethanol, diethylene glycol, polyethyleneimin propoxyethoxylate, diquaternium ethoxysulfate, alcohol sulfate, dimethicone, fragrance, borax, sodium fatty acids, DTPA, protease, sodium bisulfite, disodium diaminostilbene disulfonate, amylase, gluconase, castor oil, calcium formate, MEA, styrene acrylate copolymer, propanaminium propanamide, sodium formate, Liquitint™ Blue.

Ultra Tide Free Powdered Detergent:

Sodium Carbonate, Sodium Aluminosilicate, Alkyl Sulfate, Sodium Sulfate, Linear Alkylbenzene Sulfonate, Water, Sodium polyacrylate, Silicate, Ethoxylate, Sodium percarbonate, Polyethylene Glycol 4000, Protease, Disodium Diaminostilbene Disulfonate, Silicone, Cellulase. Ultra Tide Powdered Detergent, Clean Breeze/Spring Lavender/mountain Spring:

Sodium Carbonate, Sodium Aluminosilicate, Sodium Sulfate, Linear Alkylbenzene Sulfonate, Alkyl Sulfate, Sodium Percarbonate, Water, Sodium Polyacrylate, Silicate, Nonanoyloxybenzenesulfonate, Ethoxylate, Polyethylene Glycol 4000, Fragrance, DTPA, Disodium Diaminostilbene Disulfonate, Palmitic Acid, Protease, Silicone, Cellulase.

Ultra Tide HE (high Efficiency) Powdered Detergent, Clean Breeze:

Sodium Carbonate, Sodium Aluminosilicate, Sodium Sulfate, Linear Alkylbenzene Sulfonate, Water, Nonanoyloxybenzenesulfonate, Alkyl Sulfate, Sodium Polyacrylate, Silicate, Sodium Percarbonate, Ethoxylate, Polyethylene Glycol 4000, Fragrance, DTPA, Palmitic Acid, Disodium Diaminostilbene Disulfonate, Protease, Silicone, Cellulase.

Ultra Tide Coldwater Powdered Detergent, Fresh Scent:

Sodium Carbonate, Sodium Aluminosilicate, Sodium Sulfate, Sodium Percarbonate, Alkyl Sulfate, Linear Alkylbenzene Sulfonate, Water, Nonanoyloxybenzenesulfonate, Sodium Polyacrylate, Silicate, Ethoxylate, Polyethylene Glycol 4000, DTPA, Fragrance, Natalase, Palmitic Acid, Protease, Disodium, Diaminostilbene Disulfonate, FD&C Blue 1, Silicone, Cellulase, Alkyl Ether Sulfate.

Ultra Tide with Bleach Powdered Detergent, Clean Breeze:

Sodium Carbonate, Sodium Aluminosilicate, Sodium Sulfate, Linear Alkylbenzene Sulfonate, Sodium Percarbonate, Nonanoyloxybenzenesulfonate, Alkyl Sulfate, Water, Silicate, Sodium Polyacrylate, Ethoxylate, Polyethylene Glycol 4000, Fragrance, DTPA, Palmitic Acid, Protease, Disodium Diaminostilbene Disulfonate, Silicone, FD&C Blue 1, Cellulase, Alkyl Ether Sulfate.

Ultra Tide with Febreeze Freshness™ Powdered Detergent, Spring Renewal:

Sodium Carbonate, Sodium Aluminosilicate, Sodium Sulfate, Linear Alkylbenzene Sulfonate, Sodium Percarbonate, Alkyl Sulfate, Water, Sodium Polyacrylate, Silicate, Nonanoyloxybenzenesulfonate, Ethoxylate, Polyethylene Glycol 4000, DTPA, Fragrance, Cellulase, Protease, Disodium Diaminostilbene Disulfonate, Silicone, FD&C Blue 1.

Liquid Tide Plus with Febreeze Freshness—Sport HE Active Fresh:

Water, Sodium alcoholethoxy sulfate, MEA citrate, linear alkylbenzene sulfonate, sodium salt, linear alkylbenzene sulfonate: MEA salt, alcohol ethoxylate, sodium fatty acids, propylene glycol, diethylene glycol, polyethyleneimine ethoxylate propoxylate, diquaternium ethoxysulfate, Ethanol, sodium cumene sulfonate, borax, fragrance, DTPA, Sodium bisulfate, disodium diaminostilbene disulfonate, Mannanase, cellulase, amylase, sodium formate, calcium formate, Lauramine oxide, Liquitint™ Blue, Dimethicone/polydimethyl silicone.

Tide Plus Febreeze Freshness Spring & Renewal:

Water, sodium alcoholethoxy sulfate, linear alkyl benzene sulfonate: sodium/MEA salts, MEA citrate, propylene glycol, polyethyleneimine ethoxylate, fragrance, ethanol, diethylene glycol, polyethyleneimine propoxyethoxylate, protease, alcohol sulfate, borax, sodium fatty acids, DTPA, disodium diaminostilbene disulfonate, MEA, mannanase, gluconase, sodium formate, dimethicone, Liquitint™ Blue, tetramine.

Liquid Tide Plus with Febreeze Freshness, Sport HE Victory Fresh:

Water, Sodium alcoholethoxy sulfate, MEA citrate, linear alkylbenzene sulfonate, sodium salt, linear alkylbenzene sulfonate: MEA salt, alcohol ethoxylate, sodium fatty acids, propylene glycol, diethylene glycol, polyethyleneimine ethoxylate propoxylate, diquaternium ethoxysulfate, ethanol, sodium cumene sulfonate, borax, fragrance, DTPA, Sodium bisulfate, disodium diaminostilbene disulfonate, Mannanase, cellulase, amylase, sodium formate, calcium formate, Lauramine oxide, Liquitint™ Blue, Dimethicone/polydimethyl silicone.

Tide Vivid White+Bright Powder, Original:

Sodium Carbonate, Sodium Aluminosilicate, Sodium Sulfate, Linear Alkylbenzene Sulfonate, Sodium Percarbonate, Nonanoyloxybenzenesulfonate, Alkyl Sulfate, Water, Silicate, Sodium Polyacrylate Ethoxylate, Polyethylene Glycol 4000, Fragrance, DTPA, Palmitic Acid, Protease, Disodium Diaminostilbene Disulfonate, Silicone, FD&C Blue 1, Cellulase, Alkyl Ether Sulfate.

Wash Assays

Mini Launder-O-Meter (MiniLOM) Model Wash System

MiniLOM is a mini wash system in which washes are performed in 50 ml test tubes placed in a Stuart rotator. Each tube simulates one small washing machine and during an experiment, each will contain a solution of a specific detergent/enzyme system to be tested along with the soiled and unsoiled fabrics it is tested on. Mechanical stress is achieved via rotation (typically 20 rpm), and the temperature is controlled by placement of the rotator in a heating cabinet/room.

Terg-O-toMeter (TOM) Wash Assay

The Terg-O-toMeter (TOM) is a medium scale model wash system that can be applied to test 12 different wash conditions simultaneously. A TOM is basically a large temperature controlled water bath with up to 12 open metal beakers submerged into it. Each beaker constitutes one small top loader style washing machine and during an experiment, each of them will contain a solution of a specific detergent/enzyme system and the soiled and unsoiled fabrics its performance is tested on. Mechanical stress is achieved by a rotating stirring arm, which stirs the liquid within each beaker. Because the TOM beakers have no lid, it is possible to withdraw samples during a TOM experiment and assay for information on-line during wash.

The TOM model wash system is mainly used in medium scale testing of detergents and enzymes at US or LA/AP wash conditions. In a TOM experiment, factors such as the ballast to soil ratio and the fabric to wash liquor ratio can be varied. Therefore, the TOM provides the link between small scale experiments, such as AMSA and mini-wash, and the more time consuming full scale experiments in top loader washing machines. Equipment: The water bath with 12 steel beakers and 1 rotating arm per beaker with capacity of 500 or 1200 mL of detergent solution. Temperature ranges from 5 to 80° C. The water bath must be filled up with deionised water. Rotational speed can be set up to 70 to 120 rpm/min. Set temperature in the Terg-O-toMeter and start the rotation in the water bath. Wait for the temperature to adjust (tolerance is +/−0.5° C.). All beakers shall be clean and without traces of prior test material. The wash solution with desired amount of detergent, temperature and water hardness is prepared in a bucket. The detergent is allowed to dissolve during magnet stirring for 10 min. Wash solution shall be used within 30 to 60 min after preparation. 800 ml wash solution is added into a TOM beaker. The wash solution is agitated at 120 rpm and optionally one or more enzymes are added to the beaker. The swatches are sprinkled into the beaker and then the ballast load. Time measurement starts when the swatches and ballast are added to the beaker. The swatches are washed for 20 minutes after which agitation is terminated. The wash load is subsequently transferred from the TOM beaker to a sieve and rinse with cold tap water. The soiled swatches are separated from the ballast load. The soil swatches are transferred to a 5 L beaker with cold tap water under running water for 5 minutes. The ballast load is kept separately for the coming inactivation. The water is gently pressed out of the swatches by hand and placed on a tray covered with a paper. Another paper is placed on top of the swatches. The swatches are allowed to dry overnight before subjecting the swatches to analysis, such as measuring the color intensity using a Color Eye as described herein.

The present invention is further described by the following examples that should not be construed as limiting the scope of the invention.

Assays

Assay 1: Hexosaminidase Activity

The hexosaminidase activity of the mature polypeptides with SEQ ID NO 7, SEQ ID NO 8, and SEQ ID NO 9, was determined using 4-nitrophenyl N-acetyl-β-D-glucosaminide (Sigma-Aldrich) as substrate. The enzymatic reaction was performed in triplicates in a 96 well flat bottom polystyrene microtiter plate (Thermo Scientific) with the following conditions: 50 mM 2-(N-morpholino) ethanesulfonic acid pH 6 buffer, 1.5 mg/ml 4-nitrophenyl N-acetyl-β-D-glucosaminide and 20 μg/ml purified enzyme sample in a total reaction volume of 100 μl. Blank samples without enzyme were run in parallel. The reactions were carried out at 37° C. in a Thermomixer comfort (Eppendorf). After 10 minutes of incubation, 5 μl 1 M NaOH was added to each reaction mixture to stop the enzymatic reaction. The absorbance was read at 405 nm using a POLARstar Omega plate reader (BMG LABTECH) to estimate the formation of 4-nitrophenolate ion released because of enzymatic hydrolysis of the 4-nitrophenyl N-acetyl-β-D-glucosaminide substrate. The results are summarized in the table below. The table shows the average absorbance measured at 405 nm for each reaction performed in triplicates. It is seen that the absorbance is higher for the reaction carried out with SEQ ID NO 7, SEQ ID NO 8, SEQ ID NO 9, compared to blank without enzyme which demonstrates that SEQ ID NO 7, SEQ ID NO 8, SEQ ID NO 9 exhibit hexosaminidase activity.

TABLE 2

Hexosaminidase activity of SEQ ID NO 7, SEQ ID NO 8 and SEQ ID NO 9.

| Enzyme | Enzyme concentration | A405 nm | ΔA405 nm (A405 nm$_{sample}$ − A405 nm$_{blank}$) |
|---|---|---|---|
| Blank | 0 μg/ml | 0.158 | — |
| SEQ ID NO 7 | 50 μg/ml | 1.978 | 1.820 |
| SEQ ID NO 8 | 50 μg/ml | 1.715 | 1.557 |
| SEQ ID NO 9 | 50 μg/ml | 2.455 | 2.297 |

Assay 2: Hexosaminidase Activity

The hexosaminidase activity of the mature polypeptides with SEQ ID NO 7, SEQ ID NO 8, SEQ ID NO 9, and SEQ ID NO 10, was determined using 4-Methylumbeliferyl N-acetyl-β-D-glucosaminide (Sigma-Aldrich) as substrate. The enzymatic reaction was performed in triplicates in a 96 well flat bottom polystyrene microtiter plate (Thermo Scientific) with the following conditions: 20 mM 3-morpholinopropane-1-sulfonic add pH 7 buffer, 5 mM 4-Methylumbeliferyl N-acetyl-β-D-glucosaminide and 20 nM purified enzyme sample in a total reaction volume of 200 μl. Blank samples without enzyme were run in parallel. The reactions were carried out at ambient temperature 20-25° C. The reaction kinetics was followed immediately after mixing of enzyme and substrate using a SpectraMax M2e plate reader. Excitation wavelength was set to 368 nm and fluorescence emission reading was done at 448 nm. The reaction was followed for 30 min with 60 second intervals. Increase in fluorescence signal was used to estimate the formation of 4-Methylumbeliferyl ion released because of enzymatic hydrolysis of the 4-Methylumbeliferyl N-acetyl-β-D-glucosaminide substrate. The results are summarized in the table below. The table shows the average initial rate of reaction measured as relative fluorescence units per minute (RFU/min) using excitation at 368 nm and fluorescence emission at 448 nm for each reaction performed in triplicates. It is seen that the reaction initial rate is higher for the reaction carried out with SEQ ID NO 7, SEQ ID NO 8, SEQ ID NO 9, and SEQ ID NO 10 compared to blank without enzyme which demonstrates that SEQ ID NO 7, SEQ ID NO 8, SEQ ID NO 9, and SEQ ID NO 10 exhibit hexosaminidase activity.

TABLE 3

Hexosaminidase activity of SEQ ID NO 7, SEQ ID NO 8, SEQ ID NO 9, and SEQ ID NO 10.

| Enzyme | Enzyme concentration | Reaction initial rate (RFU/min) | Δ Reaction initial rate (RFU/min) |
| --- | --- | --- | --- |
| Blank | 0 nM | 0.6 | — |
| SEQ ID NO 7 | 20 nM | 18.5 | 17.9 |
| SEQ ID NO 8 | 20 nM | 10.1 | 9.5 |
| SEQ ID NO 9 | 20 nM | 13.1 | 12.5 |
| SEQ ID NO 10 | 20 nM | 82.6 | 82.1 |

Δ Reaction initial rate (RFU/min) = (Reaction initial rate$_{sample}$ − Reaction initial rate$_{blank}$)

EXAMPLES

Example 1 Expression and Cloning of Hexosaminidases

The DNA encoding the hexosaminidase having the polypeptide comprised in SEQ ID NO 2 was isolated from a Terribacillus saccharophilus strain obtained from ATCC in 1969 (ATCC12327). The DNA encoding the hexosaminidase having the polypeptide comprised in SEQ ID NOS 4 and 6 were isolated from a Terribacillus goriensis and a Terribacillus saccharophilus bacterial strains respectively, isolated from an environmental soil sample collected in USA. The DNA encoding the hexosaminidase having the polypeptide comprised in SEQ ID NOS 13 and 15 were isolated later from two Terribacillus saccharophilus strains, isolated from environmental samples collected in USA. Chromosomal DNA from the four Terribacillus saccharophilus strains and the Terribacillus goriensis strain was isolated by QIAamp DNA Blood Mini Kit (Qiagen, Hilden, Germany) and subjected to full genome sequencing using Illumina technology. The genome sequence was analyzed for protein sequences that have glycosyl hydrolase domains (GH20, www.cazy.org). Three GH20 genes and corresponding sequences SEQ ID NOS: 1, 3, 5, 12 and 14 were identified from Terribacillus saccharophilus and Terribacillus goriensis strains. The codon optimized synthetic DNA encoding the mature peptide sequences of the hexosaminidases were ordered from the company Geneart. The mature polypeptides are shown in SEQ ID NO 7, 8, 9 10 and 11.

TABLE 4

| enzyme | Donor |
| --- | --- |
| SEQ ID NO 7 | Terribacillus saccharophilus |
| SEQ ID NO 8 | Terribacillus goriensis |
| SEQ ID NO 9 | Terribacillus saccharophilus |
| SEQ ID NO 10 | Terribacillus saccharophilus |
| SEQ ID NO 11 | Terribacillus saccharophilus |

Example 2: Cloning and Expression of the Hexosaminidases

The codon optimized synthetic genes encoding the mature peptide sequences of the hexosaminidases or the polypeptides having hexosaminidase activity is shown in SEQ ID NO 7, 8, 9, 10 and 11. The sequences were inserted into a Bacillus expression vector as described in WO 12/025577. Briefly, the DNA encoding the mature peptide of the hexosaminidase gene was cloned in frame to a Bacillus clausii secretion signal (BcSP; with the following amino acid sequence: MKKPLGKIVASTALLISVAFSSSIASA (SEQ ID NO 16). BcSP replaced the native secretion signal in the gene. Downstream of the BcSP sequence, an affinity tag sequence was introduced to ease the purification process (His-tag; with the following amino acid sequence: HHHHHHPR (SEQ ID NO 17) The gene that was expressed therefore comprised the BcSP sequence followed by the His-tag sequence followed by the mature wild type GH20 sequence i.e. the polypeptides with SEQ ID NO 7, SEQ ID NO 8, SEQ ID NO 9, SEQ ID NO 10 and SEQ ID NO 11. The final expression plasmid (BcSP-His-tag-GH20) was transformed into a Bacillus subtilis expression host. The GH20 BcSP-fusion gene was integrated by homologous recombination into the Bacillus subtilis host cell genome upon transformation.

The gene construct was expressed under the control of a triple promoter system (as described in WO 99/43835). The gene coding for chloramphenicol acetyltransferase was used as maker (as described in (Diderichsen et al., 1993, Plasmid 30: 312-315)). Transformants were selected on LB media agar supplemented with 6 micrograms of chloramphenicol per ml. One recombinant Bacillus subtilis clone containing the GH20 expression construct was selected and was cultivated on a rotary shaking table in 500 ml baffled Erlenmeyer flasks each containing 100 ml yeast extract-based media. After 3-5 days' cultivation time at 30° C. to 37° C., the enzyme containing supernatant was harvested by centrifugation and the enzymes was purified by His-tag purification.

Example 3: His Tag Purification Method

The His-tagged GH20 hexosaminidase enzymes were purified by immobilized metal chromatography (IMAC) using Ni$^{2+}$ as the metal ion on 5 mL HisTrap Excel columns (GE Healthcare Life Sciences). The purification took place at pH 7 and the bound proteins were eluted with imidazole. The purity of the purified enzyme was checked by SDS-PAGE and the concentration of the enzyme determined by Absorbance 280 nm after a buffer exchange in 50 mM HEPES, 100 mM NaCl pH7.0

Example 4: Biofilm Assay

Staphylococcus aureus was kindly provided by Iñigo Lasa (Valle et al., Mol Microbiol. 2003 May; 48 (4):1075-87).

The strain was grown on trypticase soy agar (TSA) at 37° C. overnight. Next day, a single colony was transferred to 15 ml tripticase soy broth (TSB) and incubated 5 hours at 37° C. under shaking. The culture was diluted 1:100 in TSB+1% glucose and 100 µL of the bacterial suspension was transferred to each well of a 96-well microtiter plates (Thermo Scientific, Nunclon Delta Surface, cat #167008) and incubated 24 hours at 37° C. without shaking. Supernatant was aspirated and wells were washed with 100 µL of 0.9% sodium chloride and filled with 100 µL of either hard water or 3.3 gr/L Model detergent A containing 0 (control) or 20, 10, 5, 2.5, 1.25, 0.62, 0.31, 0.16, 0.08, 0.04, 0.02 and 0.01 µg/mL of enzyme (the mature polypeptides having SEQ ID NO 7, SEQ ID NO 8, SEQ ID NO 9, SEQ ID NO 10 and SEQ ID NO 11). After incubation at 37° C. for 1 hour, wells were washed with water and stained for 15 min with 100 µL of 0.095% crystal violet solution (SIGMA V5265). Wells were then rinsed twice with 100 µL water, dried and the plates were scanned.

The lowest concentration of each enzyme that could reduce the visible formation of S. aureus biofilm after 1 hour incubation, in the presence and absence of detergent was determined (see Table 5). All enzymes were assayed per duplicate with similar results.

TABLE 5

Minimal concentration of enzyme that can reduce the visible formation of S. aureus after 1 hour incubation in either hard water or Model detergent A.

| Enzyme | Minimal concentration for biofilm reduction in Model A µg/mL | Minimal concentration for biofilm reduction in Hard water µg/mL |
| --- | --- | --- |
| SEQ ID NO 7 | 2.5 | 0.08 |
| SEQ ID NO 8 | 2.5 | 0.16 |
| SEQ ID NO 9 | 2.5 | 0.16 |
| SEQ ID NO 10 | 0.31 | <0.01 |
| SEQ ID NO 11 | 10 | 0.02 |

Example 5: Deep-Cleaning of Hexosaminidases in Liquid Model Detergent

*Staphylococcus aureus* 15981 (kind gift from Iñigo Lasa (Valle et al., *Mol Microbiol.* 2003 May; 48 (4):1075-87) was used as model microorganism in the present example. *S. aureus* was restreaked on Tryptone Soya Agar (TSA) (pH 7.3) (CM0131; Oxoid Ltd, Basingstoke, UK) and incubated for 1 day at 37° C. A single colony was inoculated into 10 mL of TSB and the culture was incubated for 16 hours at 37° C. with shaking (200 rpm). After propagation, the *S. aureus* culture was diluted (1:100) in fresh TSB+1% glucose (24563; Roquette Freres) and 2 mL aliquots were added to the wells of 12-well polystyrene flat-bottom microplates (3512; Costar, Corning Incorporated, Corning, N.Y., USA), in which round swatches (diameter 2 cm) of sterile polyester (WFK30A) had been placed. Sterile TSB+1% glucose was added to control wells. After 48 h at 37° C. (static incubation), the swatches were rinsed twice with 15°dH water. Five rinsed swatches (sterile or with *S. aureus*) were placed in 50 mL test tubes and 10 mL of wash liquor (15°dH water with 0.2 g/L iron(III) oxide nanopowder (544884; Sigma-Aldrich) with 3.33 g/L liquid model A detergent) and 0.2 ppm enzyme (mature polypeptide with SEQ ID NO 7, 8 and 9) were added to each tube. Washes without enzyme were included as controls. The test tubes were placed in a Stuart rotator and incubated for 1 hour at 37° C. at 20 rpm. The wash liquor was then removed, and the swatches were rinsed twice with 15°dH water and dried on filter paper over night.

The color difference (L) values were measured using a Handheld Minolta CR-300, and are displayed in table 6. Delta values ($L_{(swatch\ washed\ with\ enzyme)} - L_{(swatch\ washed\ without\ enzyme)}$) are also indicated.

TABLE 6

Deep-cleaning effects of hexosaminidases in model detergent A

| Enzyme | Enzyme concentration (ppm) | L values | ΔL (Lwith enzyme − Lwithout enzyme) |
| --- | --- | --- | --- |
| No enzyme | 0 | 102.9 | |
| SEQ ID NO 7 | 0.2 | 115.1 | 12.3 |
| SEQ ID NO 8 | 0.2 | 115.5 | 12.7 |
| SEQ ID NO 9 | 0.2 | 115.2 | 12.3 |

The results show that the hexosaminidases display deep-cleaning properties in model detergent A.

Example 6: Deep-Cleaning Effects of Hexosaminidases in Liquid Model Detergent

*Staphylococcus aureus* biofilms were grown on textile swatches (wfk30A) as described in example 5. Swatches incubated with sterile medium were included as controls. For testing the deep-cleaning properties of the hexosaminidases, five rinsed swatches (sterile or with *S. aureus*) were placed in 50 mL conical centrifuge tubes and 10 mL of wash liquor (15°dH water with 0.2 g/L iron(III) oxide nanopowder (544884; Sigma-Aldrich) with 3.33 g/L liquid model A detergent) and 0.2 ppm (or 2 ppm) enzyme was added to each tube. No enzymes were added to the controls. The test tubes were placed on a Stuart rotator and incubated for 1 hour at 37° C. at 20 rpm. The wash liquor was then removed, and the swatches were rinsed twice with 15°dH water and dried on filter paper over night.

The color difference (L) values were measured using a Handheld Minolta CR-300, and the relative wash efficiencies were calculated (($L_{With\ enzyme} - L_{No\ enzyme}$)/($L_{Sterile\ swatch} - L_{No\ enzyme}$)*100) and are indicated in table 7.

TABLE 7

Percentage wash efficiency in liquid model detergent on *S. aureus* biofilm swatches

| Swatch | Enzyme | Enzyme concentration (ppm) | % Wash efficiency |
| --- | --- | --- | --- |
| S. aureus biofilm | | 0 | 0.0 |
| S. aureus biofilm | SEQ ID NO 9 | 0.2 | 83.7 |
| S. aureus biofilm | SEQ ID NO 10 | 0.2 | 82.1 |
| S. aureus biofilm | SEQ ID NO 11 | 0.2 | 62.5 |
| S. aureus biofilm | SEQ ID NO 11 | 2 | 89.1 |

Combined with the previous examples, the results show that all the polypeptides of the invention have deep cleaning properties when compared to samples comprising no enzyme.

Example 7: Deep-Cleaning Effects of Hexosaminidases on *Pseudomonas fluorescens* Biofilm Swatches A *Pseudomonas fluorescens* isolate from Iceland, was used as model microorganism in the present example.

Pseudomonas fluorescens was restreaked on Tryptone Soya Agar (TSA) (pH 7.3) (CM0131; Oxoid Ltd, Basingstoke, UK) and incubated for 3 days at ambient temperature. A single colony was inoculated into 10 mL of TSB and the culture was incubated for 16 hours at ambient temperature with shaking (Tetramax 1000, 460 rpm). After propagation, the culture was diluted (1:100) in fresh TSB and 1.65 mL aliquots were added to the wells of 12-well polystyrene flat-bottom microplates (3512; Costar, Corning Incorporated, Corning, N.Y., USA), in which round swatches (diameter 2 cm) of sterile textile (WFK20A) had been placed. Sterile TSB was added to control wells. After 48 h incubation at ambient temperature (statically), the swatches were rinsed twice with 0.9% (w/v) NaCl. Five rinsed swatches (sterile or with P. fluourescens biofilm) were placed in 50 mL test tubes and 10 mL of wash liquor (15°dH water with 0.2 g/L iron(III) oxide nanopowder (544884; Sigma-Aldrich) with 3.33 g/L liquid model A detergent) and 0.2 ppm or 2 ppm enzyme(s) was added to each tube. Washes without enzyme were included as controls. The test tubes were placed in a Stuart rotator and incubated for 1 hour at 30° C. at 20 rpm. The wash liquor was then removed, and the swatches were rinsed twice with 15°dH water and dried on filter paper over night.

The tristimulus light intensity (Y) values were measured using a DigiEYE colour measurement and imaging system (VeriVide) equipped with a Nikon D90 digital camera, and are displayed in table 8. Delta values ($Y_{(swatches\ washed\ with\ enzyme)} - Y_{(swatches\ washed\ without\ enzyme)}$) are also indicated.

TABLE 8

Deep-cleaning effects of the hexosaminidases on P. fluorescens biofilms on textile

| Swatch | Enzyme | Enzyme concentration (ppm) | Average Y values | ΔY |
| --- | --- | --- | --- | --- |
| P. fluorescens biofilm |  | 0 | 58.3 |  |
| P. fluorescens biofilm | SEQ ID NO 7 | 0.2 | 66.1 | 7.8 |
| P. fluorescens biofilm | SEQ ID NO 7 | 2 | 66.2 | 7.8 |
| P. fluorescens biofilm | SEQ ID NO 8 | 0.2 | 66.7 | 8.4 |
| P. fluorescens biofilm | SEQ ID NO 8 | 2 | 66.7 | 8.4 |
| P. fluorescens biofilm | SEQ ID NO 9 | 0.2 | 67.0 | 8.6 |
| P. fluorescens biofilm | SEQ ID NO 9 | 2 | 67.2 | 8.9 |
| P. fluorescens biofilm | SEQ ID NO 10 | 0.2 | 67.7 | 9.4 |
| P. fluorescens biofilm | SEQ ID NO 10 | 2 | 67.6 | 9.3 |
| P. fluorescens biofilm | SEQ ID NO 11 | 0.2 | 63.0 | 4.6 |
| P. fluorescens biofilm | SEQ ID NO 11 | 2 | 66.9 | 8.6 |

Example 8 Deep-Cleaning Effects of Hexosaminidases in Liquid Model Detergent Against EPS from Different Microorganisms Crude extracts of biofilm extracellular polymeric substances (EPS) were prepared from Staphylococcus aureus 15981 (kind gift from Iñigo Lasa (Valle, J., A. Toledo-Arana, C. Berasain, J. M. Ghigo, B. Amorena, J. R. Penades, and I. Lasa. 2003, Mol. Microbiol. 48:1075-1087), Staphylococcus cohnii (textile isolate, Denmark, 0437F4), Pseudomonas fluorescens (Isolate from Iceland) and Acinetobacter iwoffi (textile isolate from Denmark. For S. aureus, the extract was made as follows: The strain was restreaked on Tryptone Soya Agar (TSA) (pH 7.3) (CM0131; Oxoid Ltd, Basingstoke, UK) and incubated for 3 days at 37° C. 500 mL of TSB+1% glucose (24563; Roquette Freres) was then inoculated, aliquoted into 50 ml conical centrifuge tubes (339652; Thermo Scientific Nunc) (33 ml in each), and incubated for 24 hours at 37° C. with shaking (200 rpm). The cells were subsequently pelleted by centrifugation (10 min, 6000 g, 25° C.), pooled and resuspended in a total of 5 ml 3M NaCl. The suspension was vortexed vigorously and incubated for 15 min at ambient temperature to extract the surface-associated EPS. The cells were then re-pelleted (10 min, 5000 g, 25° C.) and the EPS-containing supernatant was retrieved. The supernatant was sterile filtered twice (0.45 μm followed by 0.2 μm), tested for sterility and stored at −20° C. until further use.

The S. cohnii isolate was restreaked on TSA, incubated for 3 days at 37° C., and used to inoculate an overnight culture (10 ml TSB+1% glucose, incubated at 37° C., 200 rpm). This culture was then diluted (1:100) into 250 ml fresh medium (TSB+1% glucose) in a Corning® CellBIND® 225 cm² Angled Neck Cell Culture Flasks with Vent Cap (Product #3293), and the flask was incubated at 37° C. for 2 days. The biofilm culture was pelleted by centrifugation (10 min, 8000 g, 25° C.), resuspended in 2.5 ml 3M NaCl and incubated for 30 min at room temperature. The cells were then re-pelleted (10 min, 5000 g, 25° C.), and the EPS-containing supernatant was retrieved, sterile filtered (0.20 μm, 16534-K, Minisart, Sartorius Stedim) and stored at −20° C. until use.

P. fluorescens was restreaked on TSA and incubated for 1 day at 20° C. The strain was inoculated into 10 mL of TSB and the culture was incubated statically for 16 hours at 20° C. After propagation, the culture was diluted (1:100) in 400 ml M63 supplemented medium (15 mM $(NH_4)_2SO_4$, 100 mM $KH_2PO_4$, 1.8 μM $FeSO_4$, 1 mM $MgSO_4 \cdot 7H_2O$, 0.4% (w/v) glycerol, 0.2% (w/v) Casamino acids and 0.0001% (w/v) Thiamine), added to a Corning® CellBIND® 225 cm² Angled Neck Cell Culture Flasks with Vent Cap and incubated statically for 3 days at 20° C. The biofilm culture was subsequently pelleted by centrifugation (10 min, 8000 g, 25° C.), and the cells resuspended in 4 ml 3M NaCl and incubated for 30 min at 30° C. to extract the surface-associated EPS. The EPS-containing supernatant obtained after centrifugation (10 min, 5000 g, 25° C.) was then sterile filtered and stored at −20° C. until further.

A crude EPS extract from A. iwoffi was prepared as follows: The strain was restreaked on a TSA plate and incubated for 3 days at 30° C. 10 ml LB medium (L3152, Fluka) was then inoculated with a single colony, and incubated at 30° C., 200 rpm for 48 h. The culture was diluted (1:100) in 300 ml fresh LB, added to Corning® CellBIND® 225 cm² Angled Neck Cell Culture Flasks with Vent Cap and incubated statically for 4 days at 30° C. The biofilm culture was subsequently pelleted by centrifugation (10 min, 8000 g, 25° C.), and the pellet was resuspended in a total of 3 ml 3M NaCl and incubated for 30 min at room temperature. The EPS-containing supernatant obtained after centrifugation (10 min, 5000 g, 25° C.) was sterile filtered (0.20 μm, 16534-K, Minisart, Sartorius Stedim) and stored at −20° C. until use.

For wash performance testing, 50 ul aliquots of the different crude EPS extracts were spotted on sterile textile swatches (WFK20A) and incubated for 15 min at ambient temperature. The swatches (sterile or with EPS) were placed in 50 mL test tubes and 10 mL of wash liquor (15°dH water with 0.2 g/L iron(III) oxide nano-powder (544884; Sigma-Aldrich) with 3.33 g/L liquid model A detergent) and 0.2 μg/ml or 2 μg/ml enzyme was added to each tube. Washes without enzyme were included as controls. The test tubes were placed in a Stuart rotator and incubated for 1 hour at 37° C. at 20 rpm. The wash liquor was then removed, and the swatches were rinsed twice with 15°dH water and dried on filter paper over night. The tristimulus light intensity (Y) values were measured using a DigiEYE colour measurement and imaging system (VeriVide) equipped with a Nikon D90 digital camera, and are displayed in table 9.

Delta values ($Y_{(swatches\ washed\ with\ enzyme)} - Y_{(swatches\ washed\ without\ enzyme)}$) and relative wash efficiency values (($L_{With\ enzyme} - L_{No\ enzyme}$)/($L_{Sterile\ swatch} - L_{No\ enzyme}$)*100)) are also indicated.

TABLE 9

Deep-cleaning effects of the hexosaminidase shown in SEQ ID NO 9 in liquid model detergent on EPS from different microorganisms

| Origin of EPS | Enzyme concentration (ppm) | Average Y values | ΔY | Wash efficiency (%) |
|---|---|---|---|---|
| Clean textile, no EPS | 0 | 85.4 | | |
| S. aureus | 0 | 41.7 | | |
| S. aureus | 0.2 | 82.7 | 41.1 | 93.8 |
| S. aureus | 2 | 84.3 | 42.6 | 97.4 |
| S. cohnii | 0 | 73.3 | | |
| S. cohnii | 0.2 | 84.6 | 11.3 | 93.0 |
| S. cohnii | 2 | 84.7 | 11.4 | 93.8 |
| P. fluorescens | 0 | 54.4 | | |
| P. fluorescens | 0.2 | 86.0 | 31.6 | 101.8 |
| P. fluorescens | 2 | 85.5 | 31.1 | 100.1 |
| A. lwoffii | 0 | 76.3 | | |
| A. lwoffii | 0.2 | 84.9 | 8.6 | 94.0 |
| A. lwoffii | 2 | 84.7 | 8.4 | 91.8 |

The data clearly shows that the hexosaminidases show deep-cleaning properties against biofilm EPS from various microorganisms, including both gram-positive and gram-negative bacteria.

Example 9: Malodor Reduction of Hexosaminidase in Liquid Model Detergent

EPS were purified as described in e.g. example 8. After purification, 50 µL aliquots of EPS were added to the wells of 12-well polystyrene flat-bottom microplates (3512; Costar, Corning Incorporated, Corning, N.Y., USA), in which round swatches (diameter 2 cm) of sterile polyester (WFK30A) had been placed. The swatches were incubated for 15 min (static incubation) before proceeding. Six swatches were placed in 50 mL test tubes and 10 mL of wash liquor (15°dH water with 3.33 g/L liquid model A detergent) and 0.2 ppm, 2.0 ppm or 20.0 ppm enzyme (SEQ ID NO 9) were added to each tube. Washes without enzyme were included as controls. The test tubes were placed in a Stuart rotator and incubated for 1 hour at 37° C. at 20 rpm. The wash liquor was then removed, and the swatches were rinsed twice with 20 mL 15°dH water and dried on filter paper over night.

Odor Chamber Setup and Analysis of Volatiles on Textile Using an Electronic Nose To test for the binding of gaseous volatiles, all dried swatches were randomly distributed in a square plastic box (30.7 cm×21.9 cm×6.0 cm—inside measurements). In a 10 mL glass beaker position in the center, 5 mL of a mixture of various aldehydes (Pentanal 160 mM, Hexanal 40 mM, Heptanal 80 mM, (E)-2-Heptenal 20 mM, Octanal 30 mM, Nonanal 10 mM, Decanal 8 mM, (E)-2-Decenal 10 mM and (E,E)-2-Decadienal 12 mM—all chemical purchased from Sigma-Aldrich) were added. The odor chamber was closed with a lid and wrapped in Parafilm®. The swatches were incubated at room temperature for 16 h, before individually being placed in the bottom of 20 mL GC-MS vials (Mikrolab Aarhus A/S, Aarhus, Denmark) and capped with silicone screw top lids (Mikrolab Aarhus A/S, Aarhus, Denmark). From each sample 5 mL headspace was analyzed in a:

Heracles II Electronic nose from Alpha M.O.S., France (double column gas chromatograph with 2 FIDs, column 1: Restek MXT-5 10 m×0.18 mm×0.2 µm and column 2: Restek MXT-1701 10 m×0.18 mm×0.2 µm) after 20 minutes incubation at 40° C. Samples were run in a randomized order.

TABLE 10

Malodor removal by hexosaminidase in Model A model detergent.

| Volatile compound | 0.2 ppm hexosaminidase (SEQ ID NO 9) (Relative intensity) | Without enzyme (Relative intensity) | Odor reduction with 0.2 ppm hexosaminidase (SEQ ID NO 9) Reduction in % |
|---|---|---|---|
| Pentanal | 917323 | 1128853 | 19 |
| Hexanal | 207470 | 280177 | 26 |
| Heptanal | 398361 | 621542 | 33 |
| (E)-2-Heptenal | 59477 | 91362 | 35 |
| Octanal | 103164 | 172130 | 37 |
| Nonanal | 88695 | 130790 | 32 |
| Decanal | 26768 | 44650 | 40 |
| (E)-2-Decenal | 18097 | 36608 | 51 |
| (E,E)-2-Decadienal | 49063 | 101721 | 52 |

The results show that hexosaminidase display malodor reduction properties in model detergent A.

Example 10: Deep-Cleaning of Hexosaminidases in Different Detergents

A crude EPS (extracellular polymeric substances) extract was prepared from *Pseudomonas fluorescens* (Isolate from Iceland) as described in example 8. For wash performance testing, 50 ul aliquots of this extract were spotted on sterile textile swatches (WFK20A) and left to soak for 15 min at ambient temperature. The swatches (sterile or with EPS) were placed in 50 mL conical centrifuge tubes and 10 mL of wash liquor (15°dH water with 0.2 g/L iron(III) oxide nano-powder (544884; Sigma-Aldrich) and with detergent (3.33 g/L liquid model A detergent, 2.0 g/L model N or 4.6 g/L Persil Universal Gel®) was added. The enzyme was added to a final concentration of 0.2 µg/ml. Tubes without enzymes were included as controls. The test tubes were placed in a Stuart rotator and incubated for 1 hour at 37° C. at 20 rpm. The wash liquor was then removed, and the swatches were rinsed twice with 15°dH water and dried on filter paper over night. The tristimulus light intensity (Y) values were measured using a DigiEYE colour measurement and imaging system (VeriVide) equipped with a Nikon D90 digital camera, and are displayed in table 11.

Delta values ($Y_{(swatch\ washed\ with\ enzyme)} - Y_{(swatch\ washed\ without\ enzyme)}$) are also indicated.

TABLE 11

Deep-cleaning of hexosaminidases in different detergents on P. fluorescens EPS swatches

| Swatch | Enzyme | Enzyme conc. (ppm) | Model A Y values | ΔY | Model N Y values | ΔY | Persil Universal Gel (commercial detergent) Y values | ΔY |
|---|---|---|---|---|---|---|---|---|
| No EPS | — | 0 | 85.6 | | 61.7 | | 84.4 | |
| EPS | — | 0 | 49.7 | | 51.9 | | 55.2 | |
| EPS | Seq ID NO. 7 | 0.2 | 85.1 | 35.5 | 74.1 | 22.2 | 82.8 | 27.6 |
| EPS | Seq ID NO. 8 | 0.2 | 83.5 | 33.8 | 75.3 | 23.4 | 83.5 | 28.3 |
| EPS | Seq ID NO. 9 | 0.2 | 85.0 | 35.3 | 73.4 | 21.5 | 81.8 | 26.5 |
| EPS | Seq ID NO. 10 | 0.2 | 86.0 | 36.3 | 74.8 | 22.9 | 84.7 | 29.5 |
| EPS | Seq ID NO. 11 | 0.2 | 81.5 | 31.8 | 72.4 | 20.5 | 77.5 | 22.2 |

Example 11: Wash Performance in TOM

A crude EPS extract was prepared from *Pseudomonas fluorescens* (Isolate from Iceland) as described in example 8. The extract was sterile filtered prior to use, and 100 µl aliquots were spotted on textile swatches (wfk20A (Polyester/Cotton mix (65%/35%)), 50 mm×50 mm), and incubated at room temperature for 10 min. The Terg-o-tometer wash was performed at follows; 0.4 g/L iron(III) oxide nanopowder (544884; Sigma-Aldrich) and 3.33 g/L liquid model detergent A was weighed out and left to soak for 1 h prior to the wash. The dirty detergent was then added to 1000 ml pre-warmed water hardness (15°dH) in the TOM beakers, and allowed to dissolve for 10 min (maximum agitation). The agitation level was then reduced to 90 rpm, and the textile swatches (two EPS swatches as well as ballast material (wfk10A, wfk30A) to reach a total of 10 g textile/beaker) were added and washed with or without enzyme (0.2 ppm) for 35 min at 30° C. After wash, all swatches were rinsed twice in tap water and dried on filter paper over night. The remisssion ($REM^{460\ nm}$) values were measured using a Macbeth Color-Eye 7000 (CE7000), and are displayed in table 12.

Delta values ($REM^{460\ nm}_{(swatches\ washed\ with\ enzyme)} - REM^{460\ nm}_{(swatches\ washed\ without\ enzyme)}$) are also indicated.

TABLE 12

Deep-cleaning properties of hexosamidases on EPS swatches, washed in TOM

| Swatch | Enzyme | Enzyme concentration (ppm) | Average Remission (460 nm) values | ΔRem(460 nm) |
|---|---|---|---|---|
| Clean textile, no EPS | | | 60.4 | |
| P. fluorescens EPS | SEQ ID NO 9 | 0 | 47.1 | |
| P. fluorescens EPS | SEQ ID NO 9 | 0.2 | 65.3 | 18.2 |

Example 12: Wash Performance in Full-Scale Wash

A crude EPS extract was prepared from *Pseudomonas fluorescens* (Isolate from Iceland) as described in example 8. The extract was spotted (200 µl aliquots) on a prewashed T-shirt (Anvil sustainable t-shirt (50% polyester/50% cotton)) that had been cut down the middle, and the spots were left to dry at room temperature for 30 min prior to the wash. The two halves of the T-shirt were washed independently in a Miele Laundry Washing Machine (Miele Softtronic, W2245) using tap water and 0.16 g/L iron(III) oxide nanopowder (544884; Sigma-Aldrich) in 3.33 g/L liquid model A detergent. The 40° C. Color program was used (run time 1 h, 26 min). After wash, the two halves of the T-shirt were hang-dried at room temperature overnight. The remisssion ($REM^{460\ nm}$) values were measured using a Macbeth Color-Eye 7000 (CE7000), and are displayed in table 13. Delta values ($REM^{460\ nm}_{(swatches\ washed\ with\ enzyme)} - REM^{460\ nm}_{(swatches\ washed\ without\ enzyme)}$) are also indicated.

TABLE 13

Deep-cleaning of hexosaminidases in full-scale washing machine

| EPS spotted on T-shirt | Enzyme | Enzyme concentration (ppm) | Average $Rem^{460\ nm}$ values | $\Delta Rem^{460\ nm}$ |
|---|---|---|---|---|
| P. fluorescens EPS | SEQ ID NO 9 | 0 | 22.4 | |
| P. fluorescens EPS | SEQ ID NO 9 | 0.2 | 45.7 | 23.3 |

Example 13: EPS Hydrolysis Measurements Using Fluorescent WGA-Alexafluor488 Assay The *Pseudomonas fluorescens* strain isolated from Iceland was used as model microorganisms in the present example. The *Pseudomonas fluorescens* strain was restreaked on Tryptone Soya Agar (TSA) (pH 7.3) (CM0131; Oxoid Ltd, Basingstoke, UK) and incubated for 1 day at 23° C. The strain was inoculated into 10 mL of TSB and the culture was incubated with shaking for 16 hours at 23° C. The overnight culture was diluted (1:100) in 200 ml M63 supplemented medium (15 mM (NH4)2SO4, 100 mM KH2PO4, 1.8 µM FeSO4, 1 mM MgSO4.7H2O, 0.4% (w/v) glycerol, 0.2% (w/v) Casamino acids and 0.0001% (w/v) Thiamine) added to a Corning® CellBIND® 225 cm² Angled Neck Cell Culture Flask with Vent Cap (Product #3293) and incubated statically for 5 days at 23° C. Each biofilm culture was subsequently transferred to four 50 ml falcon tubes (Corning #430820) and pelleted by centrifugation (10 min, 8000 g, 25° C.), and the supernatants were discarded completely. The residual pellets from each of the four falcons were resuspended in 0.450 ml 3M NaCl to extract the surface-associated EPS (extracellular polymeric substances) and pooled in one test tube (5 ml, Eppendorf #0030119401). The suspension was centrifuged at 5000 g for 10 min at 25° C. and the 1.8 ml supernatant was transferred to a new test tube as EPS fraction and stored at −20° C. until further use (termed crude EPS). 150 ul aliquots of the crude EPS were dispensed in three Eppendorf tubes and mixed with 150 ul of an enzyme solution containing 80 ppm of either SEQ ID NO 9 or 50 mM Hepes100 mM NaCl buffer alone and incubated 1 hr at room temperature. 50 ul aliquot samples were retrieved from each tube and then added to the wells of a nunc Maxisorp black microtiter plate (ThermoScientific #437111) in which round swatches of sterile prewashed swatches (wfk 20A, polyester/cotton 65%/35%) had been placed. The plate was incubated at room temperature for 15 minutes. Supernatants were then removed from each well and swatches were washed with 100 ul water. Next, 50 ul of WGA-Alexa fluor488 dye (10 ug/ml; excitation/emission maxima ~495/519 nm; Thermo Fischer Scientific, #W11261) was added to each well. Alexa Fluor® 488 WGA binds to sialic acid and N-acetylglucosaminyl residues. The plate was incubated at room temperature for 15 min. Samples were finally washed with 100 ul water and measured in the SpectraMax M3 instrument. Each of the three samples corresponding to the crude EPS mixed with the enzyme solutions and buffer control, were tested on 8 swatches placed in 8 wells. The measurements obtained including the standard deviations are listed below in table 14.

TABLE 14

Fluorescent measurements with WGA-Alexa Fluor488 dye of crude EPS from P. fluorescens strain treated with either buffer or SEQ ID NO 9.

| sample | average measurement |
|---|---|
| Buffer control | 416 |
| SEQ ID NO 9 | 121 |

Results from the fluorescent measurements show that the EPS extract from the P. fluorescens strain is labelled with WGA-Alexa Fluor488 suggesting that the EPS contains N-acetylglucosaminyl residues and is sensitive to hexosaminidase (SEQ ID NO 9) hydrolysis.

Example 14: Wheat-Germ Agglutinin (WGA)-Staining of Washed EPS Swatches

A crude EPS extract was prepared from Staphylococcus aureus 15981 (kind gift from Iñigo Lasa (Valle, J., A. Toledo-Arana, C. Berasain, J. M. Ghigo, B. Amorena, J. R. Penades, and I. Lasa. 2003, Mol. Microbiol. 48:1075-1087) as described in example 8 with minor modifications: The culture was incubated for 24 h at 37° C. in TSB+1% glucose prior to EPS extraction. For washing, 100 ul aliquots of the EPS were spotted on sterile textile swatches (prewashed wfk20A textile, 65% Polyester/35% Cotton) and incubated for 20 min at ambient temperature. The swatches (sterile or with EPS) were placed in 50 mL test tubes and 10 mL of wash liquor (15°dH water with 3.33 g/L liquid model A detergent) and 20 µg/ml enzyme was added to each tube. Washes without enzyme were included as controls. The test tubes were placed in a Stuart rotator and incubated for 1 hour at 37° C. at 20 rpm. The wash liquor was then removed, and the swatches were rinsed twice with 15°dH water and placed in a 12-well polystyrene flat-bottom microplate (3512; Costar, Corning Incorporated, Corning, N.Y., USA). The swatches were then stained with Alexa Fluor® 488 Conjugated Wheat Germ Agglutinin (WGA) (10 µg/ml in 1×PBS) for 30 min at room temperature, rinsed twice with 1×PBS and measured by well-scanning in a BMG CLARIOstar microplate reader (Excitation at 488 nm, emission at 525 nm). The fluorescence intensity values are shown in table 15.

The relative substrate removal compared to the control (FIU$_{with\ enzyme}$–FIU$_{without\ enzyme}$) is also shown.

TABLE 15

Wheat-germ agglutinin (WGA)-staining of EPS swatches washed with or without hexosaminidase (SEQ ID NO 9).

| Swatch | Enzyme concentration (ppm) | Fluorescent signal intensity (488 nm(Ex), 525 nm(Em), background subtracted) | % remaining substrate |
|---|---|---|---|
| S. aureus EPS | 0 | 49082 | 100 |
| S. aureus EPS | 20 | 3258 | 6.6 |

When WGA lectin has affinity for N-acetylglucosaminyl residues, the results shows that the hexosaminidase treatment improves substrate removal from the textile during the wash.

Example 15: Construction of Clades and Phylogenetic Trees

The Glyco_hydro_20 domain includes the polypeptides of the invention having hexosaminidase e.g. PNAG activity and comprises the WND domain as well as the clusters such as the clades. A phylogenetic tree was constructed, of polypeptide sequences containing a Glyco_hydro_20 domain, as defined in PFAM (PF00728, Pfam version 31.0 Finn (2016). Nucleic Acids Research, Database Issue 44:D279-D285). The phylogenetic tree was constructed from a multiple alignment of mature polypeptide sequences containing at least one Glyco_hydro_20 domain. The sequences were aligned using the MUSCLE algorithm version 3.8.31 (Edgar, 2004. Nucleic Acids Research 32(5): 1792-1797), and the trees were constructed using FastTree version 2.1.8 (Price et al., 2010, PloS one 5(3)) and visualized using iTOL (Letunic & Bork, 2007. Bioinformatics 23(1): 127-128). The polypeptide sequences containing a Glyco_hydro_20 domain comprises several motifs; one example is GXDE (SEQ ID NO 18), situated in positions 158 to 161 in Terribacillus saccharophilus (SEQ ID NO 9). Residues D and E are the key catalytic residues of Glyco_hydro_20 enzymes (position 160 to 161 in SEQ ID NO 9).

The polypeptides in Glyco_hydro_20 can be separated into multiple distinct sub-clusters, or clades as listed below. The distinct motifs for each clade are described in details below.

Generation of IAS Domain

A domain, preferably shared by the polypeptides of the invention, was identified. This domain has not been described previously. The domain is termed IES and polypeptides of this domain comprises Glyco_hydro_20 domain polypeptides of bacterial origin and are in addition to having PNAG activity, characterized by comprising certain motifs. The polypeptides of the domain comprise the motif example [EQ][NRSHA][YVFL][AGSTC][IVLF][EAQYN][SN] (SEQ ID NO 19), corresponding to ESYAIAS at position 44 to 50 of SEQ ID NO 9.

Generation of WND Domain

A domain, preferably shared by the polypeptides of the invention, was identified. This domain has not been described previously. The domain is termed WND and polypeptides of this domain comprise Glyco_hydro_20 domain polypeptides of bacterial origin and are in addition to having PNAG activity, characterized by comprising certain motifs. The polypeptides of the domain comprise the motif example [VIM][LIV]G[GAV]DE[VI][PSA] (SEQ ID NO 20), corresponding to pos 156 to 163 of SEQ ID NO 9, where G and DE (corresponding to positions 158 and 160-161 of SEQ ID NO 9) are fully conserved in DSP3 clade and part of the active site. Residues D and E are the key catalytic residues of Glyco_hydro_20 enzymes (position 160 to 161 in SEQ ID NO 9). Another motif which may be comprised by the polypeptides of the WND domain is WND[SQR][IVL][TLVM] (SEQ ID NO 21), 193 to 198 in SEQ ID NO 9, where W (pos 193 in SEQ ID NO 9) is part of the active site pocket and putatively involved in binding of the N-acetyl group of the PNAG substrate.

Generation of QSTL Clade

The QSTL clade comprises WND domain polypeptides of bacterial origin, having hexosaminidase e.g. PNAG activity. The polypeptides of the clade comprise the motif example QSTL (SEQ ID NO 22), corresponding to pos 216 to 219 of SEQ ID NO 9, where all four amino are fully conserved in QSTL clade. The motif is part of a putative "lid" of the enzymes' TIM barrel structure and putatively involved in substrate binding. Another motif which may be comprised by the polypeptides of the QSTL clade is NKFFY (SEQ ID NO 23), 273 to 277 in SEQ ID NO 9. A further motif which may be comprised by the polypeptides of the QSTL clade is NLD[DR]S (SEQ ID NO 24), corresponding to amino acids 204 to 208 in SEQ ID NO 9.

Figure 3:
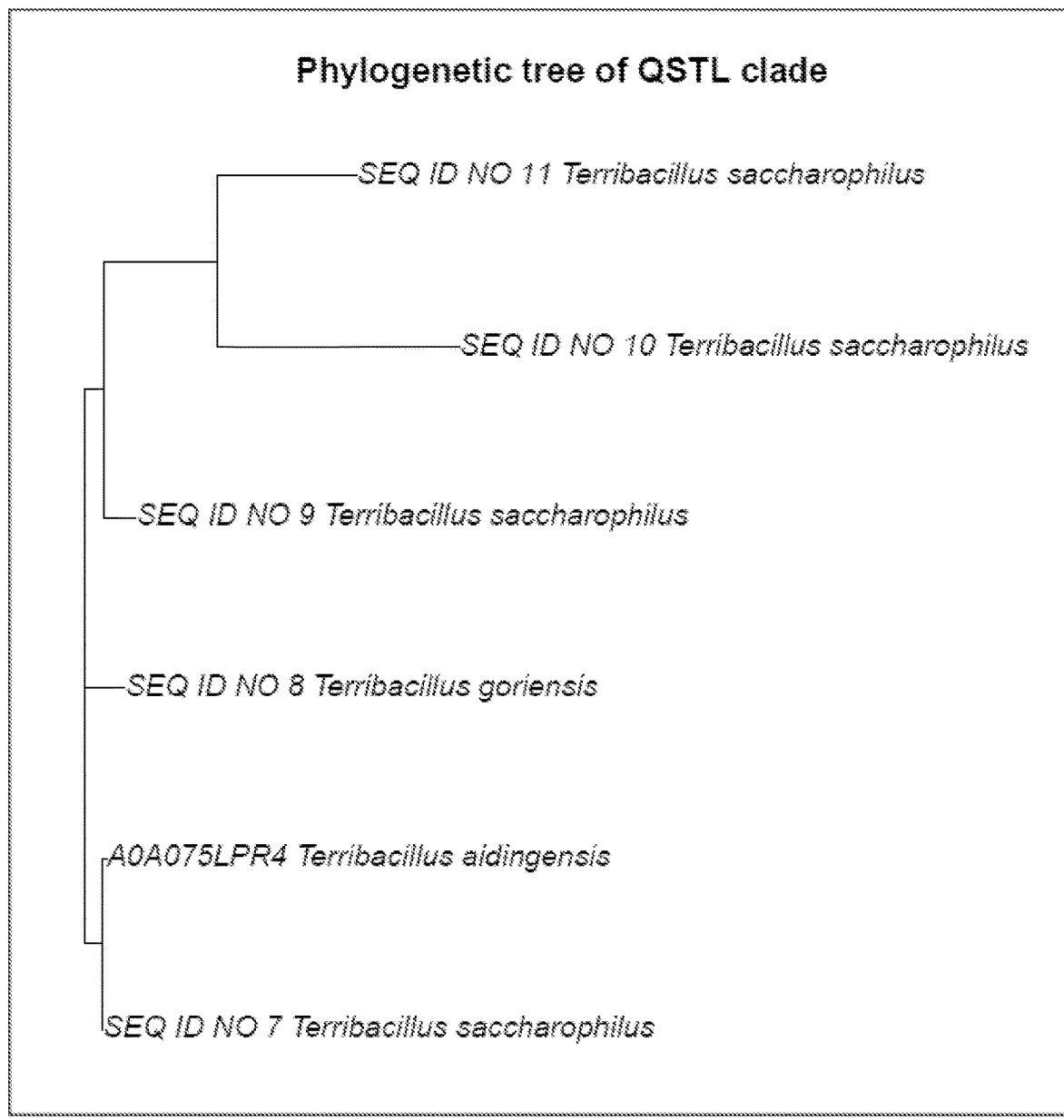

An alignment of the polypeptides of the invention is shown in FIG. 2. A phylogenetic tree of the polypeptides of the invention is shown in FIG. 3.

The invention claimed is:

1. A recombinant microbial host cell transformed with multiple copies of a polynucleotide encoding a polypeptide having hexosaminidase activity, wherein
   (a) the polynucleotide is operably linked to one or more control sequences that direct the production of the polypeptide in the recombinant host cell, and
   (b) the polypeptide is selected from the group consisting of:
      (i) a polypeptide comprising the amino acid sequence of SEQ ID NO: 7;
      (ii) a polypeptide having at least 97% sequence identity to SEQ ID NO: 8;
      (iii) a polypeptide having at least 97% sequence identity to SEQ ID NO: 9;
      (iv) a polypeptide having at least 80% sequence identity to SEQ ID NO: 10; and
      (v) a polypeptide having at least 85% sequence identity to SEQ ID NO: 11.

2. A method of producing a polypeptide having hexosaminidase activity, comprising cultivating the recombinant host cell of claim 1 under conditions conducive for production of the polypeptide.

3. The method of claim 2, wherein the polypeptide has at least 90% sequence identity to SEQ ID NO: 10.

4. The method of claim 2, wherein the polypeptide has at least 93% sequence identity to SEQ ID NO: 10.

5. The method of claim 2, wherein the polypeptide has at least 95% sequence identity to SEQ ID NO: 10.

6. The method of claim 2, wherein the recombinant host cell is a Gram-positive bacterium selected from the group consisting of *Bacillus, Clostridium, Enterococcus, Geobacillus, Lactobacillus, Lactococcus, Oceanobacillus, Staphylococcus, Streptococcus*, and *Streptomyces*.

7. The method of claim 2, wherein the recombinant host cell is a *Bacillus* host cell.

8. A recombinant microbial host cell comprising a polynucleotide encoding a polypeptide having hexosaminidase activity, wherein
   (a) the polynucleotide is operably linked to one or more control sequences that direct the production of the polypeptide in the recombinant host cell, wherein at least one of the one or more control sequences is heterologous to the polynucleotide, and
   (b) the polypeptide is selected from the group consisting of:
      (i) a polypeptide comprising the amino acid sequence of SEQ ID NO: 7;
      (ii) a polypeptide having at least 97% sequence identity to SEQ ID NO: 8;

(iii) a polypeptide having at least 97% sequence identity to SEQ ID NO: 9;
(iv) a polypeptide having at least 80% sequence identity to SEQ ID NO: 10; and
(v) a polypeptide having at least 85% sequence identity to SEQ ID NO: 11.

9. A method of producing a polypeptide having hexosaminidase activity, comprising cultivating the recombinant host cell of claim 8 under conditions conducive for production of the polypeptide.

10. The method of claim 9, wherein the polypeptide has at least 90% sequence identity to SEQ ID NO: 10.

11. The method of claim 9, wherein the polypeptide has at least 93% sequence identity to SEQ ID NO: 10.

12. The method of claim 9, wherein the polypeptide has at least 95% sequence identity to SEQ ID NO: 10.

13. The method of claim 9, wherein the recombinant host cell is a Gram-positive bacterium selected from the group consisting of *Bacillus, Clostridium, Enterococcus, Geobacillus, Lactobacillus, Lactococcus, Oceanobacillus, Staphylococcus, Streptococcus*, and *Streptomyces*.

14. The method of claim 9, wherein the recombinant host cell is a *Bacillus* host cell.

15. A recombinant microbial host cell comprising a polynucleotide encoding a polypeptide having hexosaminidase activity, wherein
(a) the polynucleotide is operably linked to one or more control sequences that direct the production of the polypeptide in the recombinant host cell, wherein the polynucleotide is heterologous to the recombinant host cell, and
(b) the polypeptide is selected from the group consisting of:
(i) a polypeptide comprising the amino acid sequence of SEQ ID NO: 7;
(ii) a polypeptide having at least 97% sequence identity to SEQ ID NO: 8;
(iii) a polypeptide having at least 97% sequence identity to SEQ ID NO: 9;
(iv) a polypeptide having at least 80% sequence identity to SEQ ID NO: 10; and
(v) a polypeptide having at least 85% sequence identity to SEQ ID NO: 11.

16. A method of producing a polypeptide having hexosaminidase activity, comprising cultivating the recombinant host cell of claim 15 under conditions conducive for production of the polypeptide.

17. The method of claim 16, wherein the polypeptide has at least 90% sequence identity to SEQ ID NO: 10.

18. The method of claim 16, wherein the polypeptide has at least 93% sequence identity to SEQ ID NO: 10.

19. The method of claim 16, wherein the polypeptide has at least 95% sequence identity to SEQ ID NO: 10.

20. The method of claim 16, wherein the recombinant host cell is a Gram-positive bacterium selected from the group consisting of *Bacillus, Clostridium, Enterococcus, Geobacillus, Lactobacillus, Lactococcus, Oceanobacillus, Staphylococcus, Streptococcus*, and *Streptomyces*.

21. The method of claim 16, wherein the recombinant host cell is a *Bacillus* host cell.

* * * * *